United States Patent
Khaldi et al.

(10) Patent No.: US 10,729,636 B2
(45) Date of Patent: Aug. 4, 2020

(54) COMPOSITIONS COMPRISING PEPTIDE WKDEAGKPLVK

(71) Applicant: NURITAS LIMITED, Dublin (IE)

(72) Inventors: Nora Khaldi, Dublin (IE); Cyril Lopez, Dublin (IE)

(73) Assignee: NURITAS LIMITED, Dublin (IE)

( * ) Notice: Subject to any disclaimer, the term of this patent is extended or adjusted under 35 U.S.C. 154(b) by 0 days.

(21) Appl. No.: 16/466,124

(22) PCT Filed: Dec. 5, 2017

(86) PCT No.: PCT/EP2017/081589
§ 371 (c)(1),
(2) Date: Jun. 3, 2019

(87) PCT Pub. No.: WO2018/104346
PCT Pub. Date: Jun. 14, 2018

(65) Prior Publication Data
US 2019/0358144 A1    Nov. 28, 2019

(30) Foreign Application Priority Data

Dec. 5, 2016 (EP) .................................... 16202305
Dec. 5, 2016 (EP) .................................... 16202306

(51) Int. Cl.
| | | |
|---|---|---|
| *C07K 7/06* | (2006.01) |
| *C07K 7/08* | (2006.01) |
| *A61K 8/64* | (2006.01) |
| *A61K 9/00* | (2006.01) |
| *A61K 38/06* | (2006.01) |
| *A61K 38/07* | (2006.01) |
| *A61K 38/08* | (2019.01) |
| *A61K 38/10* | (2006.01) |
| *A61K 38/16* | (2006.01) |
| *A61Q 19/08* | (2006.01) |

(52) U.S. Cl.
CPC .............. *A61K 8/64* (2013.01); *A61K 9/0014* (2013.01); *A61K 38/06* (2013.01); *A61K 38/07* (2013.01); *A61K 38/08* (2013.01); *A61K 38/10* (2013.01); *A61K 38/16* (2013.01); *A61Q 19/08* (2013.01); *C07K 7/06* (2013.01); *C07K 7/08* (2013.01); *A61K 2800/10* (2013.01)

(58) Field of Classification Search
None
See application file for complete search history.

(56) References Cited

U.S. PATENT DOCUMENTS

2004/0132667 A1    7/2004    Lintner

FOREIGN PATENT DOCUMENTS

| EP | 3118215 A1 | 1/2017 |
| WO | 2012130771 A1 | 10/2012 |
| WO | 2013040142 A2 | 3/2013 |
| WO | 2016172722 A1 | 10/2016 |

OTHER PUBLICATIONS

Huang et al., "Resolving the Conundrum of Islet Transplantation by Linking Metabolic Dysregulation, Inflammation, and Immune Regulation", Endocrine Reviews, 2008; pp. 603-630 (Year: 2008).*
Hancock, "Preventing and managing diabetes: an exemplar for NCDs", C3 Collaborating for Health, www.c3health.org, 2012, pp. 1-8 (Year: 2012).*
EMedicine Health, Gestational Diabetes—Prevention: Healthwise Medical Information on eMedicineHealth; http://www.emedicinehealth.com/script/main/art.asp?Articlekey=128918&pf=3&page=9; pp. 1-9 (Year: 2015).*
Finan et al., "A rationally designed monomeric peptide triagonist corrects obesity and diabetes in rodents", Nature Medicine, 2015; pp. 27-39 (Year: 2015).*
Rahnamaeian et al., "Short antimicrobial peptides as cosmetic ingredients to deter dermatological pathogens", Appl Microbiol Biotechnol, Aug. 2015, pp. 8847-8855 (Year: 2015).*

* cited by examiner

*Primary Examiner* — Lianko G Garyu
(74) *Attorney, Agent, or Firm* — Nixon Peabody LLP; David S. Resnick; Nicole D. Kling

(57) ABSTRACT

A composition comprising a cosmetically or pharmaceutically or therapeutically effective amount of a peptide comprising an amino acid sequence of SEQUENCE ID NO. 1. Modified peptides, and therapeutic and cosmetic uses of the peptide are also disclosed.

12 Claims, 9 Drawing Sheets
Specification includes a Sequence Listing.

Figure 5 (HACAT)

COMPOSITIONS COMPRISING PEPTIDE WKDEAGKPLVK

CROSS-REFERENCE TO RELATED APPLICATIONS

This application is a 35 U.S.C. § 371 National Phase Entry Application of International Application No. PCT/EP2017/081589 filed Dec. 5, 2017, which designates the U.S. and claims benefit under 35 U.S.C. § 119(a) of EP Provisional Applications 16202306.3 filed Dec. 5, 2016 and 16202305.5 filed Dec. 5, 2016, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jun. 3, 2019, is named 2019-06-03-Sequence-Listing-048262-095480USPX.TXT and is 15,075 bytes in size.

FIELD OF THE INVENTION

The present invention relates to cosmetic and pharmaceutical compositions.

BACKGROUND TO THE INVENTION

Many compositions have been described. Improvement is always desirable.

Currently, there are different approaches for improving muscle health or muscle-glucose-absorption. However, finding an alternative that helps muscle recovery, maintenance and/or muscle growth is desirable.

Indeed, the growing will of maintaining a youthful appearance is leading to more and more research of new cosmetic and dermatological procedures for treatment of skin aging, particularly as people are now living longer and healthier lives. Recently, there has been an increasing enthusiasm for minimally invasive treatments and techniques designed to deal with problems like wrinkles, volume loss and other skin damages. The most common topical anti-ageing solutions are creams and serums.

US2004/0132667 discloses compositions comprising peptides, optionally in combination with one or more additional ingredients. The compositions disclosed provide relief from one or more skin conditions, including those caused by various sources of stress, pollution and general aging.

US2014/0120141 discloses cosmetic and pharmaceutical compositions containing peptides for use in the treatment and/or care of conditions, disorders and/or diseases of the skin and/or mucous membranes.

It is an object of the invention to overcome at least one of the above-referenced problems and provide a composition.

SUMMARY OF THE INVENTION

A first aspect of the invention provides a peptide comprising an amino acid sequence of SEQUENCE ID NO. 1 (hereafter "peptide of the invention").

A second aspect of the invention provides a composition (hereinafter "composition of the invention") comprising an effective amount of a peptide of the invention.

Preferably, the composition is topical.

Typically, the composition may be a cosmetic composition comprising a cosmetically effective amount of a peptide comprising an amino acid sequence of SEQUENCE ID NO. 1 or a variant thereof.

Suitably, the composition may be a pharmaceutical composition comprising a pharmaceutically effective amount of a peptide comprising an amino acid sequence of SEQUENCE ID NO. 1 or a variant thereof.

Preferably, said peptide is a bioactive peptide.

Suitably, the composition comprises a plurality of peptides.

Typically, the composition further comprises at least one cosmetically or pharmaceutically acceptable excipient or additive.

Typically, the composition further comprises at least one cosmetically or pharmaceutically acceptable active.

Suitably, the peptide comprises an amino acid sequence consisting of SEQUENCE ID NO. 1.

Typically, said peptide comprises from about 3 to 50 amino acids in length. Preferably from about 5 to about 20 amino acids in length, preferably about 11 amino acids in length.

The invention also relates to a fragment of SEQ ID NO. 1 comprising at least three amino acids in length. Typically, said fragment is bioactive.

Preferably, said fragment has at least 4, 5, 6, 7, 8, 9, 10, or 11, amino acids in length.

Preferably, said peptide or fragment has an activity selected from one or more of anti-aging activity, glucose transport-promoting activity, cellular growth promoting activity or anabolic activity. The activity may be cosmetic, i.e. non-therapeutic, therapeutic or both.

Suitably, the peptide or fragment has anti-ageing activity.

Suitably, the peptide or fragment has glucose transport-promoting activity.

Suitably, the peptide or fragment has cellular growth promoting activity.

Suitably, the peptide or fragment has anabolic activity. Typically, the anabolic activity is muscle growth. The peptide or fragment stimulates anabolic metabolism in a mammal.

Preferably, said peptide or fragment exhibits GLUT4 translocation promotion activity. Preferably, said peptide or fragment exhibits increased protein synthesis (stimulation of anabolic metabolism activity).

Still preferred, the peptide comprises (or consists of) an amino acid sequence of any one of SEQUENCE ID NO.1 to 85, wherein the peptide typically has anti-aging activity.

Still preferred, the peptide comprises (or consists of) an amino acid sequence of any one of SEQUENCE ID NO.1 to 85, wherein the peptide typically has glucose transport-promoting activity.

Still preferred, the peptide comprises (or consists of) an amino acid sequence of any one of SEQUENCE ID NO.1 to 85, wherein the peptide typically has cellular growth promoting activity.

Still preferred, the peptide comprises (or consists of) an amino acid sequence of any one of SEQUENCE ID NO.1 to 85, wherein the peptide typically has anabolic activity.

Still preferred, the peptide comprises (or consists essentially of) an amino acid sequence of any one of SEQUENCE ID NO.1 to 85, wherein the peptide typically exhibits GLUT4 translocation promotion activity.

Still preferred, the peptide comprises (or consists essentially of) an amino acid sequence of any one of SEQUENCE ID NO.1 to 85, wherein the peptide typically exhibits increased protein synthesis (stimulation of anabolic metabolism activity).

Still preferred, the peptide comprises (or consists essentially of) an amino acid sequence of any one of SEQUENCE ID NO.1 to 85, wherein the peptide typically exhibits cellular growth promoting activity.

A further aspect of the current invention provides a non-therapeutic use of the composition of the invention as a cosmetic.

A further aspect of the current invention provides a composition of the invention as a medicament.

The following aspects may be cosmetic, i.e. non-therapeutic, or therapeutic.

An aspect of the current invention provides a composition for use in a method for anti-ageing.

A further aspect of the current invention provides a composition of the invention for use as a medicament.

The invention also provides a peptide or composition of the invention for use in a method for slowing or inhibiting, or preventing ageing of human skin. Typically, administration may be by means of a plaster or patch or a formulation suitable for topical application.

A further aspect of the invention provides a peptide or composition of the invention for use in a method of promoting growth of tissue.

The invention also provides a peptide or composition of the invention for use in a method for promoting growth of epithelial tissue.

The invention also provides a peptide or composition of the invention for use in a method for promoting growth of skin.

The invention also provides a peptide or composition of the invention for use in a method for promoting growth of an organ.

The invention also provides a peptide or composition of the invention for use in a method for promoting growth of an organism.

Preferably, the cell, tissue or organism has a normal pathology (for example ageing skin). Typically, the cell, tissue or skin has abnormal pathology (for example tissue damaged due to trauma, drug use, or epithelial tissue in the GI tract damaged due to an inflammatory disorder).

The growth promoting uses may be in-vivo or in-vitro uses. The growth promoting uses may involve administration to mammal externally (i.e. to the skin) or internally (i.e. to the GI tract).

A further aspect of the current invention provides a peptide or composition of the invention for use in a method for improving muscle status in a mammal.

A further aspect of the current invention provides a peptide or composition of the invention for use in a method for promoting recovery of muscle, typically following exercise.

A further aspect of the current invention provides a peptide or composition of the invention for use in method for maintaining or restoring muscle health (for example lean tissue mass) in a mammal.

A further aspect of the current invention provides a peptide or composition of the invention for use in a method for enhancing physical performance by topical administration.

A further aspect of the current invention provides a peptide or composition of the invention for use in a method for the treatment or prevention of a disease or condition characterised by lethargy or low energy levels.

A further aspect of the current invention provides a peptide or composition of the invention for use in a method for muscle growth or muscle building. The composition of the invention may be used in a method for increasing lean muscle mass in beef cattle and other farm animals.

A further aspect of the current invention provides a peptide or composition of the invention for use in a method for increasing protein synthesis.

A further aspect of the current invention provides a peptide or composition of the invention for use in a method for the treatment of muscle loss.

Another aspect of the invention provides the peptide or composition of the invention for use in a method for the treatment of a wound in a mammal.

A still further aspect of the invention provides a peptide or composition of the invention for use in a method for the treatment or prevention of pain in a mammal.

Another aspect of the invention provides the peptide or composition for use in a method for the treatment or prevention of a disease or condition characterised by damaged epithelial cells or tissue, and/or damaged dermal or epithelial cells or tissue. Preferably, the disease or condition is characterised by damaged dermal or epithelial cells or tissue is selected from cancer, trauma A further aspect of the invention relates to a method of treating, preventing or caring for any one of the aforementioned and described herein diseases, conditions and/or disorders comprising a step of administering the peptide or composition of the invention. The composition may be administered topically.

The uses of the invention may be therapeutic or cosmetic, i.e. non-therapeutic.

A further aspect of the invention provides a peptide or composition of the invention for use in a method of treating or preventing a metabolic disorder in a patient. In one embodiment, the metabolic disorder is a disease or syndrome characterized by a decreased response or production of insulin in the patient. In one embodiment, the metabolic disorder is selected from diabetes and pre-diabetes. The invention also provides a peptide or composition of the invention for use in treating or preventing a disease or condition selected from hyperlipidemia, obesity, hypertension, appetite-related syndromes, diabetes-related syndromes or diabetes-associated conditions (e.g., reducing the rate of glucose level-related and/or diabetes-related stroke, heart disease, kidney disease, blindness, and/or loss of sensation in the limbs), and Syndrome X.

A further aspect of the invention provides a peptide or composition of the invention for use in a method of treating a disease or condition characterized by muscle wasting, loss of lean muscle mass, reduced anabolic metabolism, catabolic wasting, or reduced protein synthesis. In one embodiment, the disease or condition is selected from sarcopaenia or cachexia. In one embodiment, the patient being treated is elderly (i.e. greater than 60 years old), and the disease is age-related sarcopaenia or cachexia. In one embodiment, the patient has cancer. In one embodiment, the patient has lethargy.

A further aspect of the invention provides a peptide or composition of the invention for use in a method of treating or preventing a disease or condition characterised by damaged epithelial cells or tissue, and/or damaged dermal or epithelial cells or tissue. Preferably, the disease or condition characterised by damaged epithelial cells or tissue is selected from cancer, tissue damaged due to trauma, drug use, or epithelial tissue in the GI tract damaged due to an inflammatory disorder.

A further aspect of the current invention provides a peptide or composition of the invention for use in a method of maintaining or restoring muscle health (for example lean tissue mass) in a mammal.

A further aspect of the current invention provides a peptide or composition of the invention for use in a method of treatment or prevention of a disease or condition characterised by lethargy or low energy levels.

Another aspect of the invention provides the peptide or composition of the invention for use in a method of treatment of a wound in a mammal.

A still further aspect of the invention provides a peptide or composition of the invention for use in a method of treatment or prevention of pain in a mammal.

Another aspect relates to a topical composition of the invention for use in treatment or prevention of a metabolic disorder in a mammal. The metabolic disorder may be diabetes.

In one embodiment, the uses of the invention include a step of administering a therapeutically effective amount of the peptide of the invention.

In one embodiment, the composition of the invention is administered systemically.

In one embodiment, the composition of the invention (especially a pharmaceutical composition) is formulated for oral or parenteral administration. Other methods of administration are described herein.

A further aspect of the invention relates to a composition comprising one or more of the peptides selected from SEQUENCE ID NO. 1 to 85.

In one embodiment, the composition of the invention comprises substantially all of the peptides of SEQUENCE ID NO. 1 to 85.

A further aspect of the current invention relates to a man-made treatment composition comprising the composition of the invention. Preferably, the treatment composition is an anti-aging composition. Preferably, the treatment is a muscle treatment composition. In an embodiment, the composition is topical. In one embodiment, the composition comprises a cream, gel, lotion, rub, powder. Preferably, the treatment is a wound treatment composition.

The invention also relates to a plaster, bandage or dressing suitable for application to the keratinous tissue or a wound and comprising the peptide or composition of the invention.

Preferably the composition or product is man-made.

Definitions

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

In this specification, the term "composition" should be understood to mean something made by the hand of man, and not including naturally occurring compositions.

The term "bioactive" when used herein refers to a peptide or fragment that has biological activity. For example, the biological activity may be one or more of glucose transport promoting activity, growth promoting activity, anti-ageing activity, anabolic activity, anabolic metabolism promoting activity, GLUT4 translocation promotion activity and protein synthesis promotion activity. The activity may be anti-inflammatory activity or anti-bacterial activity. The activity may be antioxidation.

"Glucose transport promoting" or "glucose transport promoting activity" as applied to a peptide or fragment means a peptide, variant or fragment that is capable of increasing cellular glucose uptake in the glucose uptake assay described below.

"GLUT4 translocation promoting" or "GLUT4 translocation promotion activity" as applied to a peptide or fragment means a peptide fragment that is capable of increasing GLUT4 translocation into skeletal muscle compared with an untreated control in the in vitro assay described below.

"Anti-ageing" means inhibiting or slowing the appearance of ageing of a human's skin and/or reversing the appearance of ageing. "Slowing or inhibiting ageing of the skin" means slowing or inhibiting the ageing process in the skin, and/or reversing the appearance of ageing. In one embodiment, "anti-ageing" or "anti-ageing activity" as applied to a peptide or fragment means one that is capable of increasing collagen production or elastin production in Human Dermal Fibroblasts compared with an untreated control when tested in an in-vitro assay as described below and/or capable of increasing cell proliferation in the cell proliferation assay described below.

"Cellular growth promoting" as applied to a peptide or fragment means a peptide, variant or fragment that is capable of increasing elastin production or collagen production or cellular proliferation in an assay as described below. Peptides which increase cell proliferation or have "cellular growth promoting activity" are anti-ageing peptides or variants.

"Increasing protein synthesis" as applied to a peptide of the invention means a peptide that is capable of significantly increasing the degree of phosphorylation of MTOR in the Phospho-MTOR assay described below or significantly increasing the degree of protein synthesis in the puromycin assay described below. Peptides and compositions that increase protein synthesis may be employed to stimulate anabolic metabolism in a mammal, and/or treat diseases or conditions characterised by catabolic wasting.

"Anti-inflammatory" as applied to a peptide or fragment means a peptide or fragment that is capable of significantly reducing the secretion of TNFα by LPS-stimulated J774.2 macrophages (compared with untreated LPS-stimulated J774.2 macrophages) when the macrophages are treated with 100 μM of the peptide, variant or fragment. J774.2 macrophages were treated with 100 μM of synthetic peptide for 24 hours and then stimulated with (A) LPS (10 ng/ml) for five hours or (B) LPS (10 ng/ml) for 5 hours followed by ATP (5 mM) for one hour. Supernatant was collected and levels of TNFα were determined by ELISA.

"Antibacterial" or "antibacterial activity" as applied to a peptide or fragment means a peptide, variant or fragment that is capable of visibly inhibiting the growth of a bacteria in the following agar-plate based growth inhibition assay: Peptide stock=5 mg/mL dissolved in DMSO. Bacterial inoculums were adjusted to McFarland 0.5 standard and MHA plates swabbed. Blank disks were placed in the plates and 10 μL of each compound (at 64 μg/mL—maximum concentration tested) added. Plates were incubated at 37° C. for 16-18 hours. Appropriate controls (DMSO; Mueller-Hinton media alone; and two antibiotic discs—ciprofloxacin and tetracycline) were also performed.

Anti-oxidation activity" as applied to a peptide of the invention means a peptide that exhibits anti-oxidation activity as determined by the DPPH radical scavenging assay described below. The invention relates to the use of peptides or compositions of the invention as an anti-oxidant, and in the treatment or prevention or slowing progression of diseases or conditions characterised by oxidative stress (or imbalances between pro-oxidant and anti-oxidant factors). Examples include cardiovascular disease (especially atherosclerosis), cancer, neurodegenerative disease (i.e. Parkinsons disease, Alzheimers disease, and ALS), cataract formation, diabetes, rheumatoid arthritis. Oxidation, the same chemical reaction that causes iron to rust, plays a similarly corrosive role in our bodies. The process is called oxidative stress. There are numerous studies that prove that since these diseases are mediated by oxidative stress and disbalance between pro-oxidant and antioxidant factors, antioxidants may play a pivotal role in preventing or slowing the progression of these conditions. Several studies show an association between low intakes of dietary antioxidants to an increased frequency of heart disease. On the other hand, those with high blood levels of antioxidants have lower risk of heart disease. For examples, humans who took more vitamin E on a regular basis had a 41% lower incidence of heart disease than those who took less amounts as seen in a study on nurses. Dietary increases in antioxidant vitamins may reduce the risk of heart disease by 20-30%.

Cancer kills millions worldwide. Diet may be the cause for cancer in as much as 35% of all human cancers. Low antioxidant intake in diet may also be responsible.

Pro-oxidants, or those who generate free radicals, stimulate cell division and these form the beginnings of mutagenesis and tumor formation. When a cell with a damaged DNA strand divides, it gives rise to disturbed and deformed clusters of cells that form the cancer.

Antioxidants exert their protective effect by:
decreasing oxidative damage to DNA and
decreasing abnormal increases in cell division In addition, cigarette smoking and chronic inflammation lead to strong free radical generation that seems to be the reason for many cancers. Some research has indicated that people who smoke tend to have lower antioxidant levels than non-smokers and this makes smokers more at risk of cancers.

The respiratory system is a well known target for free radical insult. This comes from endogenous factors as well as exposure to air pollutants and toxins, cigarette smoke etc.

Recent studies suggest that free radicals may be involved in the development of pulmonary disorders such as asthma. Antioxidants have been seen to reduce the development of asthmatic symptoms. Vitamin C, vitamin E, and beta carotene supplementation has been associated with improved lung function.

Free radicals can also damage nerves and the brain. Neural tissue may be particularly susceptible to oxidative damage. This is because the brain receives a disproportionately large percentage of oxygen and has large amounts of polyunsaturated fatty acids which are highly prone to oxidation and oxidative damage.

Diseases implicated to oxidative stress include:
Alzheimer's disease
Parkinson's disease
dementia etc.

Formation of cataracts is believed to involve damage to lens protein by free radicals. This leads to opacity of the lens. Cataract formation may be slowed with the regular consumption of supplemental antioxidants like vitamin E, vitamin C, and the carotenoids. Other diseases like Diabetes, Rheumatoid arthritis etc. are also associated with low antioxidant levels in blood.

The term "topical composition" refers to a composition that is formulation for topical administration. "Topical administration" refers to the application to the keratinous tissue, such as the skin, hair and nails. Topical delivery generally means delivery to the skin, but can also mean delivery to a body lumen lined with epithelial cells, for example the lungs or airways, the gastrointestinal tract, the buccal cavity. In particular, formulations for topical delivery are described in Topical drug delivery formulations edited by David Osborne and Antonio Aman, Taylor & Francis, the complete contents of which are incorporated herein by reference. Compositions or formulations for delivery to the airways are described in O'Riordan et al (Respir Care, 2002, November 47), EP2050437, WO2005023290, US2010098660, and US20070053845. Composition and formulations for delivering active agents to the iluem, especially the proximal iluem, include microparticles and microencapsulates where the active agent is encapsulated within a protecting matrix formed of polymer or dairy protein that is acid resistant but prone to dissolution in the more alkaline environment of the ileum. Examples of such delivery systems are described in EP1072600.2 and EP13171757.1. An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required. Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose.

The term "cosmetic composition" when used herein relates to a composition that can be used for cosmetic purposes, personal care and/or hygiene purposes. It will be appreciated that the composition may have more than one cosmetic purpose and may be used for more than one of these purposes at the same time. A "cosmetic" when used herein can include but are not limited to, lipstick, mascara, rouge, foundation, blush, eyeliner, facial and body powder, sunscreen, sunblock, nail polish, compacts, solids, pencils.

"Pharmaceutical compositions": A further aspect of the invention relates to a pharmaceutical composition comprising a peptide of the invention or a composition of peptides of the invention, admixed with one or more pharmaceutically acceptable diluents, excipients or carriers. Even though the peptides and compositions of the present invention can be administered alone, they will generally be administered in admixture with a pharmaceutical carrier, excipient or diluent, particularly for human therapy. The pharmaceutical compositions may be for human or animal usage in human and veterinary medicine. Examples of such suitable excipients for the various different forms of pharmaceutical compositions described herein may be found in the "Handbook of Pharmaceutical Excipients, $2^{nd}$ Edition, (1994), Edited by A Wade and P J Weller. In particular, formulations for topical delivery are described in Topical drug delivery formulations edited by David Osborne and Antonio Aman, Taylor & Francis, the complete contents of which are incorporated herein by reference. Acceptable carriers or diluents for therapeutic use are well known in the pharmaceutical art, and are described, for example, in Remington's Pharmaceutical Sciences, Mack Publishing Co. (A. R. Gennaro edit. 1985). Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid and esters of phydroxybenzoic acid. Antioxidants and suspending agents may be also used.

The term "mammal" should be understood to mean a higher mammal, especially a human. However, the term also includes non-mammalian animals such as fish. The human may be an infant, toddler, child, adolescent, adult, or elderly human. In one embodiment of the invention, the human is an elderly person, for example aged 55 or more. In one embodiment, the human is an elderly person experiencing deterioration of lean tissue mass. In one embodiment, the human is a sportsperson. In one embodiment, the human is pregnant woman. In one embodiment, the human is suffering from lethargy or perceived lack of energy.

The term "dermatologically acceptable," as used herein, means that the topical composition(s) or component(s) of the composition(s) are suitable for use in contact with human skin or keratinous tissue without risk of toxicity, incompatibility, instability and/or allergic response, and similar.

The term "sustained release" is used in a conventional sense relating to a delivery system of a compound or active, which provides the gradual release of this compound or active during a period of time and preferably, although not necessarily, with relatively constant compound release levels over a period of time.

The term "peptide" used herein refers to a polymer composed of up to 50 amino acids, for example 5 to 50 amino acid monomers typically linked via peptide bond linkage. Peptides (including fragments and variants thereof) of and for use in the invention may be generated wholly or partly by chemical synthesis or by expression from nucleic acid. For example, the peptides of and for use in the present invention can be readily prepared according to well-established, standard liquid or, preferably, solid-phase peptide synthesis methods known in the art (see, for example, J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984). When necessary, any of the peptides employed in the invention can be chemically modified to increase their stability. A chemically modified peptide or a peptide analog includes any functional chemical equivalent of the peptide characterized by its increased stability and/or efficacy in vivo or in vitro in respect of the practice of the invention. The term peptide analog also refers to any amino acid derivative of a peptide as described herein. A peptide analog can be produced by procedures that include, but are not limited to, modifications to side chains, incorporation of unnatural amino acids and/or their derivatives during peptide synthesis and the use of cross-linkers and other methods that impose conformational constraint on the peptides or their analogs. Examples of side chain modifications include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2,4,6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal. The carboxyl group may be modified by carbodiimide activation via o-acylisourea formation followed by subsequent derivatization, for example, to a corresponding amide. Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH. Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate. Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. Peptide structure modification includes the generation of retro-inverso peptides comprising the reversed sequence encoded by D-amino acids. Changes may be those that reduce susceptibility to proteolysis, reduce susceptibility to oxidation, alter binding affinity of the variant sequence (typically desirably increasing affinity), and/or confer or modify other physicochemical or functional properties on the associated variant/analog peptide.

The term "peptide comprising an amino acid sequence of SEQUENCE ID NO: 1" used herein refers to a polymer composed of up to 50 amino acids, for example 5 to 50 amino acid monomers typically linked via peptide bond linkage, that includes SEQUENCE ID NO: 1 or an amino acid sequences consisting essentially of SEQUENCE ID NO: 1, that are substantially identical to SEQUENCE ID NO.1, but altered in respect of one or more amino acid residues, for example alteration of 1, 2 or 3 residues (hereafter "variants" or "peptide variants"). Preferably such alterations involve the insertion, addition, deletion and/or substitution of 11 or fewer amino acids, more preferably of 10 or fewer, 9 or fewer, 8 or fewer, 7 or fewer, 6 or fewer, preferably 5 or fewer, 4 or fewer, even more preferably of 3 or fewer, most preferably of 1 or 2 amino acids only. Insertion, addition and substitution with natural and modified amino acids is envisaged. The peptide may have conservative amino acid changes, wherein the amino acid being introduced is similar structurally, chemically, or functionally to that being substituted. Generally, the peptide will have at least 70% amino acid sequence identity, preferably at least 80% sequence identity, more preferably at least 90% sequence identity, and ideally at least 95%, 96%, 97%, 98% or 99% sequence identity with the parent sequence.

The term "fragment" should be understood to mean a segment of amino acid SEQUENCE ID NO. 1. Typically, the fragment has between 3 and 10 contiguous amino acids in length. Generally, the fragment has a charge of −5 to +3. The charge of a peptide, fragment or region is determined using the method of Cameselle, J. C., Ribeiro, J. M., and Sillero, A. (1986). Derivation and use of a formula to calculate the net charge of acid-base compounds. Its application to amino acids, proteins and nucleotides. Biochem. Educ. 14, 131-136.

In this specification, the term "sequence identity" should be understand to comprise both sequence identity and similarity, i.e. a variant (or homo log) that shares 70% sequence identity with a reference sequence is one in which any 70% of aligned residues of the variant (or homolog) are identical to, or conservative substitutions of, the corresponding residues in the reference sequence across the entire length of the sequence. Sequence identity is the amount of characters which match exactly between two different sequences. Hereby, gaps are not counted and the measurement is relational to the shorter of the two sequences.

In terms of "sequence homology", the term should be understood to mean that a variant (or homo log) which shares a defined percent similarity or identity with a reference sequence when the percentage of aligned residues of the variant (or homolog) are either identical to, or conservative substitutions of, the corresponding residues in the reference sequence and where the variant (or homolog) shares the same function as the reference sequence.

This alignment and the percent homology or sequence identity can be determined using software programs known in the art, for example, one alignment program is BLAST, using default parameters. Details of these programs can be found at the following Internet address: http://www.ncbi.nlm.nih.gov/blast/Blast.cgi.

"Inflammatory disorder" means an immune-mediated inflammatory condition that affects humans and is generally characterised by dysregulated expression of one or more cytokines. Examples of inflammatory disorders include skin inflammatory disorders and inflammatory disorders of the joints, inflammatory disorders of the cardiovascular system, certain autoimmune diseases, lung and airway inflammatory disorders, intestinal inflammatory disorders. Examples of skin inflammatory disorders include dermatitis, for example atopic dermatitis and contact dermatitis, acne vulgaris, and psoriasis. Examples of inflammatory disorders of the joints include rheumatoid arthritis. Examples of inflammatory disorders of the cardiovascular system are cardiovascular disease and atherosclerosis. Examples of autoimmune diseases include Type 1 diabetes, Graves disease, Guillain Bane disease, Lupus, Psoriatic arthritis, and Ulcerative colitis. Examples of lung and airway inflammatory disorders include asthma, cystic fibrosis, COPD, emphysema, and acute respiratory distress syndrome. Examples of intestinal inflammatory disorders include colitis and inflammatory bowel disease. Other inflammatory disorders include cancer, hay fever, periodontitis, allergies, hypersensitivity, ischemia, depression, systemic diseases, post infection inflammation and bronchitis. The peptides and compositions of the invention may also be employed in the non-therapeutic treatment of inflammation. Examples of non-therapeutic treatment of inflammation include use to relieve normal, non-pathological, inflammation, for example inflammation in the muscles and joints following exercise.

"Disease or condition characterised by damaged dermal or epithelial cells or tissue" means any condition or disease that results in damaged dermal or epithelial tissue or cells or organs. One example is trauma which often results in damaged skin. Another example is an inflammatory skin condition such as psoriasis or eczema which often results in damaged skin. Another example is an inflammatory disorder of the lower intestines which can result in damaged epithelial cells/tissue lining the lower intestines. Another example is damaged epithelial cells/tissue lining the lower intestines caused by ingestion of a toxic or damaging substance, for example toxic chemicals or drugs. Another example is cancer, for example bowel cancer, which can result in damaged epithelial tissue in the bowel. Another condition is a peripheral inflammatory disorder such as atopic dermatitis which can result in damage to the skin in humans.

In this specification, the term "Metabolic disorder" should be understood to include pre-diabetes, diabetes; Type-1 diabetes; Type-2 diabetes; metabolic syndrome; obesity; diabetic dyslipidemia; hyperlipidemia; hypertension; hypertriglyceridemia; hyperfattyacidemia; hypercholerterolemia; hyperinsulinemia, and MODY.

"Disease or condition characterised by bacterial infection" means any condition or disease characterised by having a pathology caused by growth of bacteria or by bacterial infection, including for example MRSA, salmonella, listeria bacterial pneumonia, Staphylococcal food poisoning, bacterial meningitis. Specific examples are provided in https://en.wikipedia.org/wiki/List_of_infectious_diseases.

"Man-made" as applied to comestible products should be understood to mean made by a human being and not existing in nature.

"Improving muscle status" means improving the muscle health, for example promoting skeletal muscle protein synthesis, skeletal glucose absorption, improving lean tissue mass in therapeutic or non-therapeutic context, promoting muscle recovery generally after activity exercise, or improving muscle performance. The methods or uses may be therapeutic or non-therapeutic. The term "improving lean tissue mass status" should be understood to mean increasing lean tissue mass, or inhibiting or preventing the rate of lean tissue mass degradation.

"Promoting muscle recovery" means causing an increase in absorption of glucose in skeletal muscle compared with untreated skeletal muscle.

"Disease or condition characterised by lethargy or low energy levels" means any condition or disease characterised by a feeling or tiredness or low energy. Examples include allergies, asthma, anemia, cancer and its treatments, chronic pain, heart disease, infection, depression, eating disorders, grief, sleeping disorders, thyroid problems, medication side effects, alcohol use, or drug use.

The term "catabolic wasting" encompasses both sarcopenia and cachexia. ("Catabolic" refers to the breakdown of tissue; it is the opposite of "anabolic," which means tissue-building.)

Loss of muscle and fat tissue due to chronic illness is called cachexia. The general loss of weight and muscle mass that occurs with advancing age is called sarcopenia. In both cachexia and sarcopenia, muscle loss can lead to frailty and adversely affect a variety of clinical outcomes (Rolland 2011; Fearon 2013; Muscaritoli 2013). Individuals with cachexia and/or sarcopenia have an increased risk of death, infection, and falls; slower wound healing; significantly lower exercise and breathing capacity; and overall diminished quality of life Cachexia usually causes more rapid and pronounced weight reduction than sarcopenia and is generally characterized as loss of muscle and fat tissue totaling more than 5% of body weight, but losses of more than 20% of body weight are common. In many cases, a person with cachexia continues losing weight even if they are getting enough calories. Severe, chronic illnesses such as cancer, AIDS, and chronic obstructive pulmonary disease (COPD) are known causes of cachexia Between 50% and 80% of all cancer patients experience cachexia, and it is estimated that cachexia is the main cause of over 20% of all cancer-related deaths. Cachexia in HIV/AIDS patients is common and occurred almost universally before the advent of antiviral HIV drugs. Sarcopenia (from the Greek meaning "poverty of flesh") generally refers to age-related loss of muscle mass and function. Approximately 50% of people over age 80 experience sarcopenia. Sarcopenia can also occur as a result of physical inactivity, poor nutrition, or illness. Some researchers refer to age-related muscle loss not associated with an underlying cause as "primary sarcopenia," and that which occurs as a consequence of one or more other causes as "secondary sarcopenia". Sarcopenia is associated with increased risk of insulin resistance and type 2 diabetes in non-obese adults over age 60 years. The conventional medical establishment often fails to provide early, aggressive intervention for cachexia, resulting in poor clinical outcomes, including premature death and disability. Standard medical treatments for cachexia include encouraging consumption of liquids and food and use of certain drugs. However, many standard medical therapies to treat sarcopenia and cachexia present the risk of adverse effects such as nausea, edema, and fatigue, and some of them have not been adequately tested in clinical trials. A number of nutritional, lifestyle, and innovative pharmacological interventions may be useful to prevent and treat catabolic wasting. Whey protein, creatine, and the amino acids glutamine, arginine, leucine, and hydoxy-methylbutyrate or HMB (a leucine derivative) are especially important for building and maintaining lean muscle mass. Omega-3 fatty acids, conjugated linoleic acid, and vitamin D also fight lean tissue loss. Research on novel and emerging strategies for the prevention of muscle wasting are really much needed.

(Ribeiro S, Keheyias, J. Sarcopenia and the analysis of body composition. Adv Nutr 2014:5:260-267.

Muscaritoli A, Lucia S, Molfino A, Cederholm M T, Rossi Fanelli F, *Muscle atrophy in aging and chronic diseases: is it sarcopenia or cachexia*? Intern Emerg Med 2013; 8: 553-560.

Rolland Y, VanKan G A, Gillette-Guyonnet S, Vellas B. *Cachexia versus sarcopenia*. Curr Opin Clin Nutr Metab Care. 2010; 14(1):15-21.

Evans W J, Morley J E, Argiles J M, et al. *Cachexia: a new definition*. Clin Nutr 2008; 27:793-799.

Fearon K, Arends J, Baracos V. *Understanding the mechanisms and treatment options in cancer cachexia*. Nat Rev Clin Oncol 2013; 10(2):90-99

"Maintaining or restoring muscle health" means helping retain or restore mammalian muscle health resulting from damage incurred during exercise. By promoting glucose transport in skeletal muscle the peptides promote recovery from exercise, and relieve muscle soreness/pain and injury connected with exercise. They can also be used to decrease and prevent muscle cramping, and to allow a faster recovery from muscle cramping. Cramping can result from physical stress, mental stress, and or Repetitive Strain Injury stress. By promoting glucose transport the peptides help reduce Myopathy of the muscle, and help prevent Sarcopenia in mammals, promote recovery from injuries during exercise, and relieve muscle soreness/pain and injury connected with exercise. The invention also relates to a peptide or composition of the invention for use in maintaining or restoring muscle health in a mammal.

In this specification, the term "personal care product" should be understood to mean a composition formulated for use by humans in cleaning or treating the human body, particularly the skin, teeth, nails, feet and hair. Examples include shampoo, conditioner, skin creams and lotions, powders, dentifrice, shower gel or creams, bath or shower gel, hair dye, soap, body scrub, exfoliant, anti-dandruff solutions body lotion, shaving solutions, moisturisers, cleaners, masks, oils, serums, and rinses, deodorant, and antiperspirant.

The term "skin aging" is used in the sense in which it is generally and widely used in the art of cosmetic and personal care products. Signs of skin aging include wrinkles, lines, crevices, bumps, red spots, large pores, roughness, dullness, loss of elasticity, sagging, loss of tightness, discoloration, blotching, hyperpigmentation, freckles, keratosis, inflammation, collagen breakdown and other histological changes in the skin layers including underlying tissue.

The term "cosmetically or pharmaceutically acceptable salts" means a salt recognized for its use in animals and more specifically in human beings, and includes salts used to form base addition salts, either they are inorganic, such as and not restricted to, lithium, sodium, potassium, calcium, magnesium, manganese, copper, zinc or aluminium among others, either they are organic, such as and not restricted to, ethylamine, diethylamine, ethylenediamine, ethanolamine, diethanolamine, arginine, lysine, histidine or piperazine among others, or acid addition salts, either they are organic, such as and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, such as and not restricted to, chloride, sulfate, borate or carbonate, among others. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al., "Pharmaceutical Salts", J. Pharm. Sci., (1977), 66, 1-19].

"C-terminal domain" as applied to a fragment means the first three amino acids at the c-terminus of the fragment.

"N-terminal domain" as applied to a fragment means the last three amino acids at the n-terminus of the fragment.

"Homolog" of a reference protein should be understood to mean a protein from a different species of plant having at least 60%, 70%, 80%, 90%, 91%, 92%, 93%, 94%, 95%, 96%, 97%, 98%, 99% sequence homology with the reference protein.

In the specification, the terms "comprise, comprises, comprised and comprising" or any variation thereof and the terms "include, includes, included and including" or any variation thereof are considered to be totally interchangeable and they should all be afforded the widest possible interpretation and vice versa.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE DRAWINGS

Figure 1:
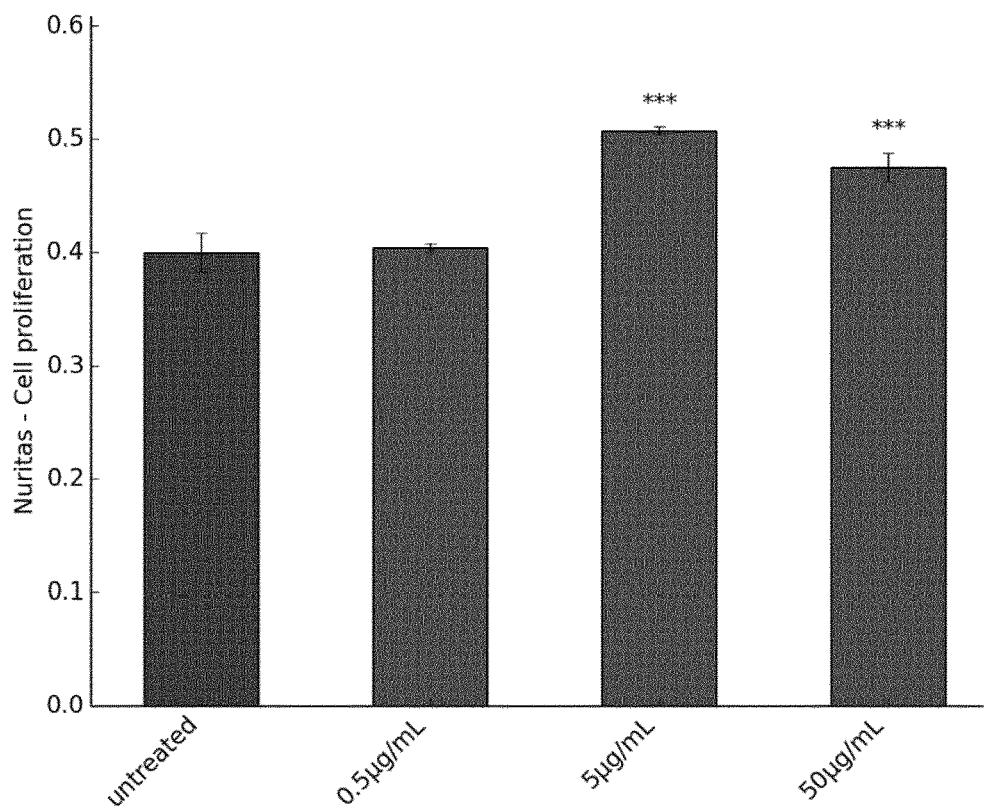
FIG. 1 illustrates results of a cell proliferation assay using untreated and peptide-treated Human Dermal Fibroblasts (HDF).

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

In the broadest sense, the first aspect of the invention provides a peptide comprising an amino acid sequence of SEQUENCE ID NO. 1 (hereafter "peptide of the invention").

In a second aspect, the invention provides a composition comprising an effective amount of a peptide of the invention.

The composition may be topical.

The composition may be a cosmetic composition comprising a cosmetically effective amount of a peptide comprising an amino acid sequence of SEQUENCE ID NO. 1 or a variant thereof.

The composition may be a pharmaceutical composition comprising a pharmaceutically effective amount of a peptide comprising an amino acid sequence of SEQUENCE ID NO. 1 or a variant thereof.

It will be understood that the composition may have a cosmetic effect, i.e. non-therapeutic or a therapeutic effect. The composition may have a cosmetic and a therapeutic effect.

Examples of cosmetic applications include, but are not limited to, anti-ageing, slowing or inhibiting, or preventing ageing of human skin, promoting growth of tissue, promoting growth of epithelial tissue, promoting growth of skin, promoting growth of an organ, promoting growth of an organism, improving muscle status in a mammal, promoting recovery of muscle, typically following exercise, maintaining or restoring muscle health in a mammal, enhancing physical performance, muscle growth or muscle building and treatment of muscle loss.

The invention also provides therapeutic uses/applications, especially non-topical therapeutic applications, of the composition or peptide of the invention.

Examples of therapeutic applications include, but are not limited to, promoting growth of tissue, promoting growth of epithelial tissue, promoting growth of skin, promoting growth of an organ, promoting growth of an organism, improving muscle status in a mammal, promoting recovery of muscle, maintaining or restoring muscle health in a mammal, muscle growth or muscle building, treatment of muscle loss, treatment or prevention of a disease or condition characterised by by muscle wasting or reduced anabolic activity or reduced protein synthesis (catabolic wasting), treatment or prevention of a disease or condition characterised or mediated by oxidative stress, treatment or prevention of a metabolic disease especially diabetes or pre-diabetes, treatment or prevention of a disease or condition characterised by lethargy or low energy levels, treatment of a wound in a mammal, treatment or prevention of pain in a mammal, treatment or prevention of a disease or condition characterised by damaged epithelial cells or tissue, and/or damaged dermal or epithelial cells or tissue tissue and treatment or prevention of a metabolic disorder in a mammal, such as diabetes.

SEQUENCE ID NO.1 has the following sequence:

WKDEAGKPLVK

In an embodiment of the invention, the peptide is bioactive.

In an embodiment, the peptide has glucose transport promoting activity. In one embodiment, the peptide has cellular growth promoting activity. In one embodiment, the peptide has anti-aging activity. In an embodiment, the peptide has anabolic activity. It will be appreciated that the peptide may have two or three of glucose transport promoting activity, cellular growth promoting activity, anti-aging activity and anabolic activity. The peptide may have glucose transport promoting activity, cellular growth promoting activity, anti-aging activity and anabolic activity.

In an embodiment of the invention the peptide comprises from about 3 to 50 amino acids in length, about 14 to about 50 amino acids in length, preferably about, 15, 20, 25, 30, 35, 40, 45, or 49 amino acids in length, preferably about 14, 15, 16, 17, 18, 19, or 20 amino acids in length.

In an embodiment of the invention the peptide comprises from about 3 to about 11 amino acids in length, preferably about, 4, 5, 6, 7, 8, 9, or 10, amino acids in length.

In one embodiment, the peptide has 1 to 5 amino acid changes compared to SEQUENCE ID NO: 1. In one embodiment, the peptide has 1 to 4 amino acid changes compared to SEQUENCE ID NO: 1. In one embodiment, the peptide has 1 to 3 amino acid changes compared to SEQUENCE ID NO: 1. In one embodiment, the peptide has 1 to 2 amino acid changes compared to SEQUENCE ID NO: 1. In one embodiment, the amino acid change is a conservative amino acid change. In one embodiment, the amino acid change is an amino acid substitution. In one embodiment, the amino acid substitution is a conservative substitution. In one embodiment, the amino acid change is an amino acid addition. In one embodiment, the amino acid change is an amino acid deletion.

The peptide of the invention includes the following variant peptides:—
Variants of SEQUENCE ID NO: 1

Variants of SEQUENCE ID NO: 1 (WKDEAGKPLVK) including variants having 1, 2 or 3 conservative amino acid substitutions, 1, 2 to 3 non-conservative amino acid substitutions, 1, 2 or 3 amino acid additions, 1, 2 or 3 amino acid deletions, are provided below:

One Conservative Amino Acid Substitution:

```
WKEEAGKPLVK;        (SEQ ID NO. 2)

FKDEAGKPLVK;        (SEQ ID NO. 3)

WKDEAGKPMVK;        (SEQ ID NO. 4)

WKDEAGRPLVK;        (SEQ ID NO. 5)

WRDEAGKPLVK;        (SEQ ID NO. 6)

WKDEAGKPLMK;        (SEQ ID NO. 7)

WKDQAGKPLVK;        (SEQ ID NO. 8)

WKDEATKPLVK         (SEQ ID NO. 9)
```

Two Conservative Amino Acid Substitutions:

```
YKNEAGKPLVK;        (SEQ ID NO. 10)

WKNESGKPLVK;        (SEQ ID NO. 11)

WKDEAGKTLVR;        (SEQ ID NO. 12)

FKDEATKPLVK;        (SEQ ID NO. 13)

FKDEAGKPLIK;        (SEQ ID NO. 14)

WKDEAGKTLLK;        (SEQ ID NO. 15)

WKNEAGKPVVK;        (SEQ ID NO. 16)

WKDEAGRTLVK         (SEQ ID NO. 17)
```

Three Conservative Amino Acid Substitutions:

```
WEDESGKPLLK;        (SEQ ID NO. 18)

WKEEAGKPIVQ;        (SEQ ID NO. 19)
```

YKNEAGKPLVR; (SEQ ID NO. 20)

WKDQATRPLVK; (SEQ ID NO. 21)

WKDESGKPVLK; (SEQ ID NO. 22)

WQDDSGKPLVK; (SEQ ID NO. 23)

WKNEAGKTLLK; (SEQ ID NO. 24)

WKDKAGEPLVR (SEQ ID NO. 25)

One Non-Conservative Amino Acid Substitution:

WKDEAGNPLVK; (SEQ ID NO. 26)

CKDEAGKPLVK; (SEQ ID NO. 27)

WKDEAGKPLGK; (SEQ ID NO. 28)

WKDENGKPLVK; (SEQ ID NO. 29)

WKDEARKPLVK; (SEQ ID NO. 30)

WKDEAGKPLVT; (SEQ ID NO. 31)

WKDEAGKRLVK; (SEQ ID NO. 32)

WKWEAGKPLVK (SEQ ID NO. 33)

Two Non-Conservative Amino Acid Substitution:

WKDEAGFPTVK; (SEQ ID NO. 34)

WYDMAGKPLVK; (SEQ ID NO. 35)

WKDYEGKPLVK; (SEQ ID NO. 36)

WKREAGKPGVK; (SEQ ID NO. 37)

WKLEKGKPLVK; (SEQ ID NO. 38)

WKDEAGKPCVK; (SEQ ID NO. 39)

WKKEAPKPLVK; (SEQ ID NO. 40)

SKDEAGPPLVK (SEQ ID NO. 41)

Three Non-Conservative Amino Acid Substitution:

WKHEPGKPLAK; (SEQ ID NO. 42)

WKDEREKPFVK; (SEQ ID NO. 43)

WKQEAGKPWRK; (SEQ ID NO. 44)

VKDEAKKPLVH; (SEQ ID NO. 45)

NWDEAGKMLVK; (SEQ ID NO. 46)

IKDEDGPPLVK; (SEQ ID NO. 47)

LKDEYGKPLVN; (SEQ ID NO. 48)

WKDRAGKELTK (SEQ ID NO. 49)

Amino Acid Additions

WKDEAGKPLPVK; (SEQ ID NO. 50)

WKGDENYAGKPLVK; (SEQ ID NO. 51)

LWKDEAGRKYPLVK; (SEQ ID NO. 52)

WKDCEGAGKPLVK; (SEQ ID NO. 53)

WKQEPAGKPLVVK; (SEQ ID NO. 54)

WKDEAGPKPLVK; (SEQ ID NO. 55)

WKDEAGWADKPLVK; (SEQ ID NO. 56)

WKNDEAGKPLVK (SEQ ID NO. 57)

Amino Acid Deletions

WKDAKPLVK; (SEQ ID NO. 58)

WKEAGKPVK; (SEQ ID NO. 59)

WKDEAKPLVK; (SEQ ID NO. 60)

WDEAGKPV; (SEQ ID NO. 61)

WKDEAGKPVK; (SEQ ID NO. 62)

WDAGKPLVK; (SEQ ID NO. 63)

WKDEAGKPLV; (SEQ ID NO. 64)

WEAGKPLV (SEQ ID NO. 65)

The variant peptide may be a bioactive variant.

The invention also provides fragments of SEQ ID NO. 1, and peptides comprising one or more of these fragments.

The fragment may be a bioactive fragment. In one embodiment, the fragment is an anti-aging fragment. In one embodiment, the fragment is a cellular growth promoting fragment. In one embodiment, the fragment is a glucose transport promoting fragment. In one embodiment, the fragment is an anabolic fragment. It will be appreciated that in one embodiment the bioactive fragment is two or more of an anti-aging fragment, glucose transport promoting fragment, cellular growth promoting fragment and an anabolic fragment. In one embodiment, the bioactive fragment is an anti-aging fragment, glucose transport promoting fragment, cellular growth fragment and an anabolic fragment.

The fragment may be a bioactive fragment. In one embodiment, the fragment is a cellular growth promoting fragment. In one embodiment, the fragment is a GLUT4 translocation promoting fragment. In one embodiment, the fragment exhibits anabolic metabolism stimulating activity. In one embodiment, the fragment exhibits anti-oxidation or anti-inflammatory activity.

Examples of fragments of SEQ ID NO: 1 are provided below:

WKDEAG; (SEQ ID NO. 66)

WKDEA; (SEQ ID NO. 67)

KDEAGKPL; (SEQ ID NO. 68)

KDEAG; (SEQ ID NO. 69)

DEAGKPL; (SEQ ID NO. 70)

GKPLV; (SEQ ID NO. 71)

DEAGK; (SEQ ID NO. 72)

WKDEAGKPL; (SEQ ID NO. 73)

WKD; (SEQ ID NO. 74)

KDE; (SEQ ID NO. 75)

KPLVK; (SEQ ID NO. 76)

WKDE; (SEQ ID NO. 77)

AGKPL; (SEQ ID NO. 78)

EAG; (SEQ ID NO. 79)

AGK; (SEQ ID NO. 80)

KPL; (SEQ ID NO. 81)

LVK; (SEQ ID NO. 82)

GKP; (SEQ ID NO. 83)

DEA; (SEQ ID NO. 84)

PLV (SEQ ID NO. 85)

It will be appreciated that the composition may comprise a plurality of peptides or fragments. Preferably, the composition comprises at least two peptides of the invention.

Preferably, the composition comprises at least three peptides of the invention. Preferably, the composition comprises at least four peptides of the invention. Preferably, the composition comprises at least five peptides of the invention. Preferably, the composition comprises at least six peptides of the invention. Preferably, the composition comprises at least seven peptides of the invention. Preferably, the composition comprises at least eight peptides of the invention. Preferably, the composition comprises at least nine peptides of the invention. Preferably, the composition comprises at least ten peptides of the invention. In one embodiment, the composition comprises substantially all the peptides. In one embodiment, the composition comprises substantially all the variants. In one embodiment, the composition is substantially free of other peptides.

In an embodiment, the peptide or composition of the invention has an activity selected from one or more of anti-bacterial activity, anti-inflammatory activity and anti-oxidant activity. The activity may be cosmetic, i.e. non-therapeutic, therapeutic or both. The invention also provides a composition of the invention for use in a method of maintaining or restoring gut health in a mammal. The invention also provides a composition of the invention for use in a method for the treatment of a bacterial infection. A further aspect of the invention provides a composition of the invention for use in a method for the treatment or prevention of an inflammatory disorder and/or inflammation in a mammal. Preferably, the inflammation is symptomatic inflammation. This use may be in addition to the above discussed uses of the invention or as an alternative.

In an embodiment, the peptide or fragment or composition of the invention has an activity selected from one or more of anti-bacterial activity, anti-inflammatory activity and anti-oxidant activity The composition may be a topical composition. The topical composition may be presented in a formulation selected from the group comprising creams, multiple emulsions, anhydrous compositions, aqueous dispersions, oils, milks, balsams, foams, lotions, gels, cream gels, hydro-alcoholic solutions, hydro-glycolic solutions, cosmetic, personal care product, hydrogels, liniments, sera, soaps, dusting powder, paste, semi solid formulations, liniments, serums, shampoo, conditioner, ointments, any rinse off formulation, talc, mousses, powders, sprays, aerosols, solutions, suspensions, emulsions, syrups, elixirs, polysaccharide films, patches, gel patches, bandages, an adhesive system, water-in-oil emulsions, oil-in-water emulsions, and silicone emulsions.

In an embodiment of the current invention, the emulsion contains a lipid or oil. The emulsion may be, but is not limited to, oil-in-water, water-in-oil, water-in-oil-in-water and oil-in-water-in-silicone emulsions. The emulsion may contain a humectant. The emulsion may contain an anti-foaming agent, such as silicone. The emulsion may have any suitable viscosity. Emulsions may further contain an emulsifier and/or an anti-foaming agent. Methods of preparing an emulsion are known to a person skilled in the art.

The composition of the invention may be presented, prepared and/or administered in a variety of suitable forms. Such forms include, for example, but are not limited to, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles, microparticles, and suppositories. It will be appreciated that the form may depend on the intended mode of administration, the nature of the composition or combination, and therapeutic application or other intended use. Formulations also can include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions, carbowax (polyethylene glycols of various molecular weights), semi-solid gels, and semi-solid mixtures containing carbowax.

It is to be understood that an ingredient that is considered to be an "active" ingredient in one product may be a "functional" or "excipient" ingredient in another and vice versa. It will also be appreciated that some ingredients play a dual role as both an active ingredient and as a functional or excipient ingredient.

In a particularly preferred embodiment, the methods and uses of the invention involve administration of a peptide or composition of the invention in combination with one or more other active agents, for example, existing growth promoting drugs or pharmacological enhancers available on the market. In such cases, the compounds of the invention may be administered consecutively, simultaneously or sequentially with the one or more other active agents.

In preferred embodiments, repeated use of the composition is provided.

The composition of the invention may be incorporated into a medical device for administration. Such a device can include but is not limited to a fabric, patch, bandage, gauze, sock, tight, underwear, dressing, glove, mask, adhesive patches, non-adhesive patches, occlusive patches and microelectric patches or suitable adhesive system. In such an embodiment, the device is in direct contact with the keratinous layer such as the skin, thus releasing the peptides of the invention. It will be understood that the topical composition may be incorporated in any suitable form as detailed herein. For example, the topical composition or peptides of the invention can be incorporated into the device or be present on the surface of the device or can be in a cream, gel or wax formulation or any suitable formulation defined herein and incorporated into the device or on the surface of the device.

The device may be adapted for adhesion or attachment to the skin. In one embodiment, the device is adapted to release a constant quantity of the composition or the peptides of the invention. It will be understood that the amount of the composition contained in the sustained release system will depend, for example, on where the composition is to be administered, the kinetics and duration of the release of the composition of the invention, as well as the nature of the condition, disorder and/or disease to be treated and/or cared for. The device may be such that the composition is released by biodegradation of the device, or by friction between the device and the body, due to bodily moisture, the skin's pH or body temperature.

In an embodiment of the invention the composition may further comprise at least one cosmetically or pharmaceutically acceptable excipient. Excipient may be used interchangeably with functional ingredient or additive. It will be understood that although the topical compositions of the current invention can be administered alone, they will generally be administered in admixture with a cosmetic or pharmaceutical excipient. Cosmetically or pharmaceutically acceptable excipient are well known in the art and any known excipient, may be used provided that it is suitable for topical administration and is dermatologically acceptable without undue toxicity, incompatibility and/or allergic reaction.

Preferably any excipient included is present in trace amounts. The amount of excipient included will depend on numerous factors, including the type of excipient used, the nature of the excipient, the component(s) of the topical composition, the amount of active or peptide in the topical composition and/or the intended use of the topical composition. The nature and amount of any excipient should not unacceptably alter the benefits of the peptides of this invention.

In an embodiment of the invention the excipient may be a suitable diluent, carrier, binder, lubricant, suspending agent, coating agent, preservative, stabilisers, dyes, vehicle, solubilising agent, base, emollient, emulsifying agent, fragrance, humectant, and/or surfactants.

Examples of suitable diluents include, but are not limited to, any diluent disclosed in disclosed in US2014120131 or US2004132667. Examples include ethanol, glycerol and water. Examples of suitable carriers include, but are not limited to, lactose, starch, glucose, methyl cellulose, magnesium stearate, mannitol, sorbitol and any suitable carrier disclosed in US2014120131 or US2004132667.

Examples of suitable binders include, but are not limited to, starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol and any suitable binder disclosed in US2014120131 or US2004132667.

Examples of suitable lubricants include, but are not limited to, sodium oleate, sodium stearate, magnesium stearate, sodium benzoate, sodium acetate, and sodium chloride and any suitable lubricant disclosed in US2014120131 or US2004132667.

The carrier may be any suitable carried known in the art or disclosed in US2014120131 or US2004132667. In some embodiments, the carrier may include, but is not limited to, a liquid, such as water, oils or surfactants, including those of petroleum, animal, plant or synthetic origin, polymer, oil, such as peanut oil, mineral oil, castor oil, soybean oil, alcohol, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, or digitonin. It will be understood that the carrier will be dermatologically acceptable. Preferred carriers contain an emulsion such as oil-in-water, water-in-oil, water-in-oil-in-water and oil-in-water-in-silicone emulsions. Emulsions may further contain an emulsifier and/or an anti-foaming agent.

In an embodiment of the invention, the composition may further comprise one or more additional ingredients. The composition of the invention may be administered consecutively, simultaneously or sequentially with the one or more other additional agents. Such additional ingredients may be those of benefit to include in a topical composition, or of benefit depending on the intended use of the topical composition. The additional ingredient may be active or functional or both.

Examples of such additional ingredients include, but are not limited to, one or more of cleaning agents, conditioning agents, sunscreen, pigment, moisturiser, thickening agents, gelling agents, essential oil, astringents, pigments, anti-caking agent, anti-foaming agent, binders, additives, buffers, chelating agents, external analgesics, film formers or materials, bulking agents, polymers, opacifying agents, pH adjusters, propellants, reducing agents, sequestrants, skin bleaching and lightening agents, skin conditioning agents, aloe vera, healing agents, soothing agents, smoothing agents, pantothenic acid, treating agents, thickeners, vitamins. colourants, pharmaceuticals, antiseptic agents, anti-foaming agents, buffering agents, astringents, polymers, pH adjuster, deodorant or any other dermatologically acceptable carrier or surfactant.

It is to be understood that additional ingredients listed may provide more than one benefit. The classification given herein is for clarity and convenience only and not intended to limit the additional ingredient to that particular application or category listed.

Any additional ingredients should be suitable for application to the skin without undue toxicity, incompatibility and/or allergic reaction.

In some embodiments, the additional ingredient has glucose transport activity or aids glucose transport activity. In some embodiments, the additional ingredient has anabolic activity. In some embodiments, the additional ingredient has anti-inflammatory activity or aids anti-inflammatory activity. In some embodiments, the additional ingredient has anti-aging activity or aids anti-aging activity. In some embodiments, the additional ingredient is for keratinous layer health and/or development, skin health and/or development, and/or muscle health, recovery and/or development. The active agent may be a pharmacological enhancer. Such active agents are known and available on the market. In such cases, the topical composition of the invention may be administered consecutively, simultaneously or sequentially with the one or more other active agents.

In some embodiments, the additional ingredient may be farnesol ([2E,6E],-3,7,11,-trimethyl-2,6,10, dodecatrien-1-ol), phytantriol (3,7,11,15, tetramethylhexadecane-1,2,3,-triol), desquamation actives, enzymes, enzyme inhibitors, enzyme activators, botanical extracts and marine extracts, anti-acne actives, anti-wrinkle or anti atrophy actives, antioxidant/radical scavengers, chelators, flavonoids, anti-inflammatory agents, anti-cellulite agents, topical anaesthetics, tanning actives, skin lightening agents, skin healing agents, bisabolol, antimicrobial or antifungal active, sunscreen actives, particulate material, conditioning agents, structuring agents, thickening agent. The desquamation active may be any suitable agent that enhances the skin appearance or texture of the skin and is as disclosed in US2014120131 or US2004132667.

Examples of anti-acne actives are as disclosed in US2014120131 or US2004132667 and include, resorcinol, salicylic acid, erythromycin, zine, sulfur, benzoyl peroxides.

Examples of thickening agents are as disclosed in US2014120131 or US2004132667 and include carboxylic acid polymers, crosslinked polyacrylate polymers, polyacrylamide polymers, polysaccharides.

Examples of conditioning agents are as disclosed in US2014120131 or US2004132667 and include humectants, moisturiser or skin conditioner.

Examples of structuring agents are as disclosed in US2014120131 or US2004132667 and include any agent that provide rheological characteristics to the composition and contributes to the stability of the composition.

Any suitable antimicrobial or antifungal active may be used and examples are as disclosed in US2014120131 or US2004132667. Such actives are capable of destroying microbes, preventing growth or action of microbes. Examples include but are not limited to β-lactam drugs, quinolone drugs, tetracycline, erythromycin, streptomycin sulfate, salicylic acid, benzoyl peroxide.

Examples of a particulate material include metallic oxide.

Examples of anti-cellulite agents include xanthine agents.

Examples of tanning actives includes 1,3-dihydroxy-2-propanone and those disclosed in US2014120131 or US2004132667.

Examples of topical anaesthetics include benzocaine, lidocaine and bupivacaine and those disclosed in US2014120131 or US2004132667.

Examples of skin lightening agents include any agent known in the art such as kojic acid, ascorbic acid and those disclosed in US2014120131 or US2004132667.

Examples of sunscreen actives include any suitable organic or inorganic sunscreen active. Examples include metallic oxides, 2-ethylhexyl-p-methoxycinnamate and those disclosed in US2014120131 or US2004132667.

Examples of skin healing agents includes panthenoic acid as disclosed in US2014120131 or US2004132667.

Examples of anti-inflammatory agents include any agent that enhances the skin appearance, tone or colour and include but are not limited to corticosteroids, hydrocortisone, non-steroidal agents such as ibuprofen and aspirin and those disclosed in US2014120131 or US2004132667.

Examples of flavonoids includes flavanones, methoxy flavonones, unsubstituted chalcone and mixtures thereof and those disclosed in US2014120131 or US2004132667.

Examples of enzymes include lipases, proteases, catalase, super oxide-dismutase, amylase, peroxidase, glucuronidase, ceramidases, hyaluronidases. Examples of enzyme inhibitors include trypsine inhibitors, Bowmann Birk inhibitors, chymotrypsin inhibitors, botanical extracts, flavonoids, quercetin chalcone and those disclosed in US2014120131 or US2004132667 and mixtures thereof. Examples of enzyme activators include coenzyme A, Q10 (ubiquinone), glycyrrhizin, berberine, chrysin and those disclosed in US2014120131 or US2004132667 and mixtures thereof.

Examples of anti-wrinkle or anti atrophy actives include sulfur containing D and L amino acids, particular, N-acyl derivatives such as N-acetyl-L-cysteine, hydroxyl acids, phytic acid, lipoic acid, lysophosphatidic acid, skin peel agents, vitamin B3, retinoids and those disclosed in US2014120131 or US2004132667 and mixtures thereof.

The anti-oxidant/radical scavenger agent may be any agent that is useful for providing protection against UV radiation or other environmental agents which may cause skin damage such as those disclosed in US2014120131 or US2004132667. Examples of anti-oxidant/radical scavengers include ascorbic acid, its salts and derivatives (vitamin C), tocopherol its salts and derivatives (vitamin E), butylated hydroxyl benzoic acids and their salts, peroxides, gallic acids and alkyl esters, sorbic acid, lipoic acid, amines, lycine pidolate, arginine pilolate, nordihydroguaiaretic acid, bioflavonoids, curcumin, lysine, methionine, proline, superoxide dismutase, silymarin, tea extracts and mixtures thereof.

Examples of chelators include EDTA, NTA, hydoxamic acids, phytic acid, lactoferrin and those disclosed in US2014120131 or US2004132667 and mixtures thereof. A chelator means an agent capable of removing a metal ion by forming a complex so that the metal ion cannot participate in or catalyse chemical reactions. A chelator is useful for protection against UV radiation or other environmental agents that can cause skin damage.

It will be appreciated that a plurality of additional ingredients may be added. The amount of the additional ingredient may be from about 0.001% to about 50% weight of the composition, preferably, about 0.01% to about 20%, preferably about 0.1% to about 10%, about 0.5% to about 10%, about 1% to about 5%, preferably 2% weight of the composition. The amount of additional ingredient included will depend on numerous factors, including the type of additional ingredient used, the nature of the additional ingredient, the component(s) of the topical composition, the amount of active or peptide in the topical composition and/or the intended use of the topical composition. The nature and amount of any additional ingredient should not unacceptably alter the benefits of the peptides of this invention.

The topical composition may be alcohol free.

In some embodiments of the invention, the composition further comprises one or more additional active agents, in addition to the peptide of the invention (also known as the active of the composition). In addition, or alternatively, the composition may be administered with one or more other additional active agents. Typical said additional active agent is present in trace amounts only. In some embodiments, there may be no additional active agent present in the composition. The amount of additional active agent included will depend on numerous factors, including the type of additional active agent used, the nature of the additional active agent, the component(s) of the topical composition, the amount of active or peptide in the topical composition and/or the intended use of the topical composition. The nature and amount of any additional active agent should not unacceptably alter the benefits of the peptides of this invention.

It is to be understood that an ingredient that is considered to be an "active" ingredient in one product may be a "functional" or "excipient" ingredient in another and vice versa. It will also be appreciated that some ingredients play a dual role as both an active ingredient and as a functional or excipient ingredient.

Examples of the additional active agents include glucose transport promoting drugs, skin supplement, agent for treatment and/or care of the skin, anti-inflammatory agent, an anti-aging agent, anabolic agents, a cellular growth promoting agent and pharmacological enhancers. Such agents are well known in the art and it will be appreciated that any suitable additional active agent may be used. Additional active agents for treatment and/or care of the skin may include collagen synthesis agents, retinoids, exfoliating agents, anti-cellulite agents, elastase inhibiting agents, melanin synthesis stimulating or inhibiting agents, self-tanning agents, antiaging agents, antimicrobial agents, antifungal agents, fungistatic agents, bactericidal agents, and healing agents. Active agents also include anti-inflammatory agents.

Any additional active agent should be suitable for application to the skin without undue toxicity, incompatibility and/or allergic reaction. It will be understood that the classification given herein is for clarity and convenience only and not intended to limit the additional ingredient, excipient, or active to that particular application or category listed.

In a particularly preferred embodiment, the methods and uses of the invention involve administration of a peptide or composition of the invention in combination with one or more other active agents, for example, existing growth promoting drugs or pharmacological enhancers available on the market. In such cases, the compounds of the invention may be administered consecutively, simultaneously or sequentially with the one or more other active agents.

In an embodiment, the effect of the current invention is accomplished by topical application or administration of the topical composition of the invention described herein to a person, animal or a patient in need of treatment or care. Topical delivery preferably means delivery to a keratinous layer such as the skin, hair and/or nails, but can also mean delivery to a body lumen lined with epithelial cells, for example the lungs or airways, the gastrointestinal tract, the buccal cavity. The effect may be confined to the surface of the skin or may be within the skin or a combination of both.

The topical composition of the invention is administered in a cosmetically or pharmaceutically effective amount. In other words, in an amount that is non-toxic but sufficient amount to provide the desired effect. It will be appreciated that a person skilled in the art would be capable of determining an appropriate dose of the topical compositions of the invention to administer without undue experimentation. Alternatively, a physician will determine the actual dose that is most suitable for a patient depending on the particular condition, disease or disorder to be treated or cared for and the age, body weight and/or health of the person. It will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. There can, of course, be individual instances where higher or lower dosage ranges are merited, and such are within the scope of this invention. For example, the composition may be administered at a dose of from 0.01 to 50 mg/kg body weight, such as from 0.1 to 30 mg/kg, more preferably from 0.1 to 20 mg/kg body weight, more preferably from 0.1 to 10 mg/kg body weight, preferably 0.1 to 5 mg/kg body weight. In an exemplary embodiment, one or more doses of 10 to 300 mg/day or more preferably, 10 to 150 mg/day, will be administered to the patient. The amount and the frequency is as best suited to the purpose. The frequency of application or administration can vary greatly, depending on the needs of each subject, with a recommendation of an application or administration range from once a month to ten times a day, preferably from once a week to four times a day, more preferably from three times a week to three times a day, even more preferably once or twice a day.

In preferred embodiments, repeated use of the composition is provided.

The topical composition may be applied by, but not limited to, rubbing, or massaging into the keratinous tissue, skin or area of the body to be treated or cared for. In some embodiments, the composition is left on or not removed from the area of the body. In other embodiments, the composition is removed after a period of time, such as, but not limited to, from about 2 minutes to 60 minutes, from about 5 minutes to about 30 minutes, preferably from about 10 minutes to about 20 minutes. The composition may be removed immediately after application. In some embodiments of the current invention, the composition of the invention may be applied to an area to be treated by means to achieve a greater penetration of the composition and/or peptide of the invention, such as, but not limited to, iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof.

The peptides or fragments of the invention are used in the topical cosmetic or pharmaceutical composition of this invention at cosmetically or pharmaceutically or therapeutically effective concentrations to achieve the desired effect; in a preferred form with regards to the total weight of the composition, between 0.00000001% (in weight) and 20% (in weight); preferably between 0.000001% (in weight) and 15% (in weight), more preferably between 0.0001% (in weight) and 10% (in weight) and even more preferably between 0.0001% (in weight) and 5% (in weight). Ideally, the peptides of the present invention are preferably used from about 0.00001% w/w to about 0.5% w/w, and more preferably from 0.00005 w/w to about 0.05 w/w, and most preferably from about 0.0001 w/w to about 0.01 w/w of the composition. Ideally, the peptides of the present invention are preferably used from about 0.0001% w/w to about 0.004% w/w of the composition.

The composition of the invention may be administered individually or in combination with other pharmacologically active agents. It will be understood that such combination therapy encompasses different therapeutic regimens, including, without limitation, administration of multiple agents together in a single dosage form or in distinct, individual dosage forms. If the agents are present in different dosage forms, administration may be simultaneous or near-simultaneous or may follow any predetermined regimen that encompasses administration of the different agents. The suitable active agents may be as described herein.

In some embodiments of the current invention, the composition may be delivered via any one of liposomes, mixed liposomes, oleosomes, niosomes, ethosomes, millicapsules, capsules, macrocapsules, nanocapsules, nanostructured lipid carriers, sponges, cyclodextrins, vesicles, micelles, mixed micelles of surfactants, surfactant-phospholipid mixed micelles, millispheres, spheres, liposcheres, particles, nanospheres, nanoparticles, milliparticles, solid nanopartciles as well as microemulsions including water-in-oil microemulsions with an internal structure of reverse micelle and nanoemulsions microspheres, microparticles.

A variety of methods are available for preparing liposomes. See, e.g., Szoka et al., Ann. Rev. Biophys. Bioeng. 9:467 (1980), U.S. Pat. Nos. 4,186,183, 4,217,344, 4,235, 871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91/17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858:161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vehicles and ether fusion methods, all of which are well known in the art.

These delivery systems may be adapted to achieve a greater penetration of the compound and/or peptides of the invention. This may improve pharmacokinetic and pharmacodynamics properties. The delivery system may be a sustained release system wherein the compound or peptide of the invention is gradually released during a period of time and preferably with a constant release rate over a period of time. The delivery systems are prepared by methods known in the art. The amount of peptide contained in the sustained release system will depend on where the composition is to be delivered and the duration of the release as well as the type of the condition, disease and/or disorder to be treated or cared for.

The compound of the invention may be administered by oral administration. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. The compound may be coated, or co-administer the compound with, a material to prevent its inactivation.

The composition of the invention may be a food product or a beverage product. In one embodiment, the man-made comestible product is a sports nutrition product, for example a beverage, snack or supplement. In one embodiment, the man-made comestible product is a beverage. In one embodiment, the man-made comestible product is a bakery product. In one embodiment, the man-made comestible product is a dairy product. In one embodiment, the man-made comestible product is a snack product. In one embodiment, the man-made comestible product is a baked extruded food product. In one embodiment, the man-made comestible product is powdered milk. In one embodiment, the man-made comestible product is an infant formula product. In one embodiment, the man-made comestible product is a confectionary product. In one embodiment, the man-made comestible product is a yoghurt. In one embodiment, the man-made comestible product is a yoghurt drink. In one embodiment, the man-made comestible product is an ice cream product. In one embodiment, the man-made comestible product is a frozen food product. In one embodiment, the man-made comestible product is a breakfast cereal. In one embodiment, the man-made comestible product is a bread. In one embodiment, the man-made comestible product is a flavoured milk drink. In one embodiment, the man-made comestible product is a confectionary bar. In one embodiment, the man-made comestible product is a tea or tea product. In one embodiment, the man-made comestible product is a based extruded snack product. In one embodiment, the man-made comestible product is a fried snack product. In one embodiment, the man-made comestible product is a nutritional supplement. In one embodiment, the man-made comestible product is a sports nutritional product. In one embodiment, the man-made comestible product is a baby food product. In one embodiment, the man-made comestible product is a speciality food product for immunocompromised individuals. In one embodiment, the man-made comestible product is a food for geriatric patients.

In one embodiment, the composition is a plant food product. In one embodiment, the composition is a cell culture media. In one embodiment, the composition is an animal feed. In one embodiment, the composition is an animal feed supplement. In one embodiment, the composition is a medical food.

In an embodiment, the composition of the invention may be administered by parenteral administration (e.g., intravenous, subcutaneous, intraperitoneal, and/or intramuscular administration). For example, it may be administered by intravenous infusion or injection or by intramuscular or subcutaneous injection.

The composition of the invention may be for human or animal usage in human and veterinary medicine.

The composition of the invention may be used for pharmaceutical, personal care and/or cosmetic uses.

The composition can be used to treat or care for any disease, disorder or condition of the skin, including but not limited to, psoriasis, dermatitis, allergic dermatitis, eczema, spongiosis, edema, skin cancer, ulcers, acne, scars, cellulitis, elastosis, keratosis, rosacea, varicose veins, inflammatory disorders.

The composition can be used for non-topical treatment of any disease, disorder or condition of the skin, including but not limited to, psoriasis, dermatitis, allergic dermatitis, eczema, spongiosis, edema, skin cancer, ulcers, acne, scars, cellulitis, elastosis, keratosis, rosacea, varicose veins, inflammatory disorders.

The composition may be used for non-topical treatment of a wound in a mammal. In another embodiment, the composition is for use in the non-topical treatment or prevention of a disease or condition characterised by damaged epithelial cells or tissue, and/or damaged dermal or epithelial cells or tissue. The disease may be but is not limited to cancer and trauma.

The composition may be used to for treating or caring for visible signs of aging including but not limited to wrinkles, stretch marks and dark circles, dryness, fine lines, age spots, red blotches, sagging skin, and conditions caused by sun exposure including sunburn, stress, pollution and/or diet. The topical composition may also be used for delaying, slowing or inhibiting the skins or the onset of aging. The composition may be administered by a medical device, such as a plaster or a patch as described herein.

The composition may be used to treat or care for a wound in a mammal. In another embodiment, the topical composition is for use in the treatment or prevention of a disease or condition characterised by damaged epithelial cells or tissue, and/or damaged dermal or epithelial cells or tissue. The disease may be but is not limited to cancer and trauma.

The composition may be used to treat or care for any muscle condition, to improve, muscle status in a mammal, to promote recovery of muscle, typically following exercise, to maintain or restore muscle health (for example lean tissue mass) in a mammal, to enhance physical performance, in treatment or prevention of a disease or condition characterised by lethargy or low energy levels.

The composition may be used to increase or stimulate muscle growth.

The composition may be used to promote growth of a tissue, promote growth of epithelial tissue, promote growth of skin, promote growth of an organ, promote growth of an organism. The skin can have a normal pathology and/or an abnormal pathology.

The composition may also be used to treat or care for any inflammatory disorder. In one embodiment, the inflammatory disorder is an inflammatory disorder of the joints. In one embodiment, the inflammatory disorder is an inflammatory disorder of the cardiovascular system. In one embodiment, the inflammatory disorder is an autoimmune disease. In one embodiment, the inflammatory disorder is a lung and airway inflammatory disorder. In one embodiment, the inflammatory disorder is an intestinal inflammatory disorder. In one embodiment, the inflammatory disorder is dermatitis. In one embodiment, the inflammatory disorder is acne vulgaris. In one embodiment, the inflammatory disorder is psoriasis. In one embodiment, the inflammatory disorder is rheumatoid arthritis. In one embodiment, the inflammatory disorder is cardiovascular disease. In one embodiment, the inflammatory disorder is atherosclerosis. In one embodiment, the inflammatory disorder is Type I diabetes.

In one embodiment, the inflammatory disorder is Graves disease. In one embodiment, the inflammatory disorder is Guillain-Barre disease. In one embodiment, the inflammatory disorder is Lupus. In one embodiment, the inflammatory disorder is Psoriatic arthritis. In one embodiment, the inflammatory disorder is Ulcerative colitis. In one embodiment, the inflammatory disorder is asthma. In one embodiment, the inflammatory disorder is cystic fibrosis. In one embodiment, the inflammatory disorder is COPD. In one embodiment, the inflammatory disorder is emphysema. In one embodiment, the inflammatory disorder is acute respiratory distress syndrome. In one embodiment, the inflammatory disorder is colitis. In one embodiment, the inflammatory disorder is inflammatory bowel disease.

The composition may also be used to treat or care for a metabolic disorder. In one embodiment, the metabolic disorder is pre-diabetes. In one embodiment, the metabolic disorder is diabetes. In one embodiment, the metabolic disorder is Type-1 diabetes. In one embodiment, the metabolic disorder is Type-2 diabetes. In one embodiment, the metabolic disorder is metabolic syndrome. In one embodiment, the metabolic disorder is obesity. In one embodiment, the metabolic disorder is diabetic dyslipidemia. In one embodiment, the metabolic disorder is hyperlipidemia. In one embodiment, the metabolic disorder is hypertension. In one embodiment, the metabolic disorder is hypertriglyceridemia. In one embodiment, the metabolic disorder is hyperfattyacidemia. In one embodiment, the metabolic disorder is hypercholerterolemia. In one embodiment, the metabolic disorder is hyperinsulinemia. In one embodiment, the metabolic disorder is MODY. The composition of the invention may also be used in a method for treating a patient suffering from a disease condition associated with or caused by hyperinsulinaemia, hypoglycaemia, hypokalaemia, and/or hypophosphataemia. The present invention further relates to method for treating glycaemic-related diseases or disorders, comprising the administration of insulin derivatives or insulin conjugates. Glycaemic-related diseases or disorders include diabetes of Type I and II, and gestational diabetes. Also, cystic fibrosis, polycystic ovary syndrome, pancreatitis and other pancreas-related diseases may also be treated.

In an embodiment of the invention the composition is for use in maintaining or restoring gut health.

In an embodiment of the invention the composition is for use in a method for the treatment or prevention of local pain.

The composition has a use as a personal care product, a supplement, a cosmetic, a pharmaceutical product.

A method of treating, preventing or caring for any one of the diseases, disorders or conditions described herein is also provided, said method comprising a step of administering the composition or topical composition of the invention. The composition may be administered to the skin, hair, the nails. The composition may be administered in any dose or frequency as disclosed herein by any method of administration or of any method of topical application.

In one embodiment, the composition is a cosmetic composition. In one embodiment, the composition is a pharmaceutical composition. It will be appreciated that the composition may have a dual function and be both a cosmetic and pharmaceutical composition.

It will be appreciated that the composition may be a therapeutic composition or may be a non-therapeutic composition. The composition may have a dual role.

Compositions may be formulated in unit dosage form, i.e., in the form of discrete portions containing a unit dose, or a multiple or sub-unit of a unit dose.

In a particularly preferred embodiment, the methods and uses of the invention involve administration of a peptide or composition of the invention in combination with one or more other active agents available on the market. In such cases, the compounds of the invention may be administered consecutively, simultaneously or sequentially with the one or more other active agents.

Modified Peptides

In one embodiment, the peptide of the invention (including peptide fragments and variants) may be a modified peptide. The term "modified peptide" is used interchangeably with the term derivative of the peptide. In one embodiment, the term "modified peptide" means a peptide that is modified to exhibit one or more of the following properties compared with the unmodified peptide: increase plasma half-life; increase the lipophilicity of the peptide; increase the renal clearance of the modified peptide; increase the activity of the modified peptide, and increase the resistance of the modified peptide to proteolytic degradation (i.e. by mammalian and especially human gastrointestinal proteases). Various methods of modifying a peptide of the invention to exhibit these properties are disclosed herein, including conjugating the peptide with a binding partner (for example an albumin binding small molecule, large polymer, long life plasma protein, or antibody or antibody-fragment), cyclisation, addition of N- or C-terminal, or side chain, protecting groups, replacing one or more L-amino acids with D-isomers, amino acid modification, increased plasma protein binding, increased albumin binding The modified peptide includes but is not limited to a peptide which has been substituted with one or more groups as defined herein, or conjugated with a binding partner, or cyclized. Generally, the peptide is modified to increase it half-life in-vivo in an animal. Various methods of modification are provided below.

In one embodiment, the modification may be any modification that provides the peptides and or the composition of the invention with an increased ability to penetrate a cell. In one embodiment, the modification may be any modification that increases the half-life of the composition or peptides of the invention. In one embodiment, the modification may be any modification that increases activity of the composition or peptides of the invention. In one embodiment, the modification may be any modification that increases selectivity of the composition or peptides of the invention.

In one embodiment, the group is a protecting group. The protecting group may be an N-terminal protecting group, a C-terminal protecting group or a side-chain protecting group. The peptide may have one or more of these protecting groups.

The person skilled in the art is aware of suitable techniques to react amino acids with these protecting groups. These groups can be added by preparation methods known in the art, for example the methods as outlined in paragraphs [0104] to [0107] of US2014120141. The groups may remain on the peptide or may be removed. The protecting group may be added during synthesis.

In an embodiment of the invention the peptides may be substituted with a group selected from one or more straight chain or branched chain, long or short chain, saturated, or unsaturated, substituted with a hydroxyl, amino, amino acyl, sulfate or sulphide group or unsubstituted having from 1 to 29 carbon atoms. N-acyl derivatives include acyl groups derived from acetic acid, capric acid, lauric acid, myristic acid, octanoic acid, palmitic acid, stearic acid, behenic acid, linoleic acid, linolenic acid, lipoic acid, oleic acid, isosteric acid, elaidoic acid, 2-ethylhexaneic acid, coconut oil fatty acid, tallow fatty acid, hardened tallow fatty acid, palm kernel fatty acid, lanolin fatty acid or similar acids. These may be substituted or unsubstituted. When substituted they are preferably substituted with hydroxyl, or sulphur containing groups such as but not limited to $SO_3H$, SH, or S—S.

In an embodiment of the current invention, the peptide is $R_1$—X—$R_2$.

$R_1$ and/or $R_2$ groups respectively bound to the amino-terminal (N-terminal) and carboxyl-terminal (C-terminal) of the peptide sequence.

In one embodiment, the peptide is $R_1$—X. Alternatively, the peptide is X—$R_2$.

Preferably, $R_1$ is H, $C_{1-4}$ alkyl, acetyl, benzoyl or trifluoroacetyl;
X is the peptide of the invention;
$R_2$ is OH or $NH_2$.

In an embodiment, $R_1$ is selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl, Tert-butyloxycarbonyl, 9-fluorenylmethyloxycarbonyl (Fmoc) and $R_5$—CO—, wherein $R_5$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group formed by —$NR_3R_4$, —$OR_3$ and —$SR_3$, wherein $R_3$ and $R_4$ are independently selected from the group formed by H, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and with the condition that $R_1$ and $R_2$ are not α-amino acids.

In accordance with another preferred embodiment, $R_2$ is —$NR_3R_4$, —$OR_3$ or —$SR_3$ wherein $R_3$ and $R_4$ are independently selected from the group formed by H, substituted or unsubstituted $C_1$-$C_{24}$ alkyl, substituted or unsubstituted $C_2$-$C_{24}$ alkenyl, Tert-butyloxycarbonyl, 9-fluorenylmethyloxycarbonyl (Fmoc), substituted or unsubstituted $C_2$-$C_{24}$ alkynyl, substituted or unsubstituted $C_3$-$C_{24}$ cycloalkyl, substituted or unsubstituted $C_5$-$C_{24}$ cycloalkenyl, substituted or unsubstituted $C_8$-$C_{24}$ cycloalkynyl, substituted or unsubstituted $C_6$-$C_{30}$ aryl, substituted or unsubstituted $C_7$-$C_{24}$ aralkyl, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$, wherein $R_3$ and $R_4$ are independently selected from the group formed by H, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_{10}$ cycloalkyl, substituted or unsubstituted $C_6$-$C_{15}$ aryl and substituted or unsubstituted heterocyclyl of 3-10 members, substituted or unsubstituted heteroarylalkyl with a ring of 3 to 10 members and an alkyl chain of 1 to 6 carbon atoms. More preferably $R_3$ and $R_4$ are selected from the group formed by H, methyl, ethyl, hexyl, dodecyl, or hexadecyl. Even more preferably $R_3$ is H and $R_4$ is selected from the group formed by H, methyl, ethyl, hexyl, dodecyl, or hexadecyl. In accordance with an even more preferred embodiment, $R_2$ is selected from —OH and —$NH_2$.

In accordance with another embodiment of this invention $R_1$ is selected from the group formed by H, acetyl, lauroyl, myristoyl or palmitoyl, and $R_2$ is —$NR_3R_4$ or —$OR_3$ wherein $R_3$ and $R_4$ are independently selected from H, methyl, ethyl, hexyl, dodecyl and hexadecyl, preferably $R_2$ is —OH or —$NH_2$. More preferably, $R_1$ is acetyl or palmitoyl and $R_2$ is —$NH_2$.

In a preferred embodiment, the acyl (or acetyl) group is bound to the N-terminal end of at least one amino acid of the peptide.

In an embodiment of the invention, the peptide is modified to comprise a side chain protecting group. The side chain protecting group may be one or more of the group comprising benzyl or benzyl based groups, t-butyl-based groups, benzyloxy-carbonyl (Z) group, and allyloxycarbonyl (alloc) protecting group. The side chain protecting group may be derived from an achiral amino acid such as achiral glycine. The use of an achiral amino acid helps to stabilise the resultant peptide and also facilitate the facile synthesis route of the present invention. Preferably, the peptide further comprises a modified C-terminus, preferably an amidated C-terminus. The achiral residue may be alpha-aminoisobutyric acid (methylalaine). It will be appreciated that the specific side chain protecting groups used will depend on the sequence of the peptide and the type of N-terminal protecting group used.

In one embodiment of the invention the peptide is conjugated, linked or fused to one or more polyethylene glycol polymers or other compounds, such as molecular weight increasing compounds. The molecular weight increasing compound is any compound that will increase the molecular weight, typically by 10% to 90%, or 20% to 50% of the resulting conjugate and may have a molecular weight of between 200 and 20,000, preferably between 500 and 10,000. The molecular weight increasing compound may be PEG, any water-soluble (amphiphilic or hydrophilic) polymer moiety, homo or co-polymers of PEG, a monomethyl-substituted polymer of PEG (mPEG) and polyoxyethylene glycerol (POG), polyamino acids such as poly-lysine, poly-glutamic acid, poly-aspartic acid, particular those of L conformation, pharmacologically inactive proteins such as albumin, gelatin, a fatty acid, polysaccharide, a lipid amino acid and dextran. The polymer moiety may be straight chained or branched and it may have a molecular weight of 500 to 40000 Da, 5000 to 10000 Da, 10000 to 5000, Da. The compound may be any suitable cell penetrating compound, such as tat peptide, penetratin, pep-1. The compound may be an antibody molecule. The compound may be a lipophilic moiety or a polymeric moiety.

The lipophilic substituent and polymeric substituents are known in the art. The lipophilic substituent includes an acyl group, a sulphonyl group, an N atom, an O atom or an S atom which forms part of the ester, sulphonyl ester, thioester, amide or sulphonamide. The lipophilic moiety may include a hydrocarbon chain having 4 to 30 C atoms, preferably between 8 and 12 C atoms. It may be linear or branched, saturated or unsaturated. The hydrocarbon chain may be further substituted. It may be cycloalkane or heterocycloalkane. The peptide may be modified at the N-terminal, C-terminal or both. The polymer or compound is preferably linked to an amino, carboxyl or thio group and may be linked by N-termini or C-termini of side chains of any amino acid residue. The polymer or compound may be conjugated to the side chain of any suitable residue.

The polymer or compound may be conjugated via a spacer. The spacer may be a natural or unnatural amino acid, succinic acid, lysyl, glutamyl, asparagyl, glycyl, beta-alanyl, gamma-amino butanoyl.

The polymer or compound may be conjugated via an ester, a sulphonyl ester, a thioester, an amide, a carbamate, a urea, a sulphonamide.

A person skilled in the art is aware of suitable means to prepare the described conjugate.

Peptides can be chemically modified by covalent conjugation to a polymer to increase their circulating half-life, for example. Exemplary polymers and methods to attach such polymers to peptides are illustrated in, e.g., U.S. Pat. Nos. 4,766,106; 4,179,337; 4,495,285; and 4,609,546. Additional illustrative polymers include polyoxyethylated polyols and polyethylene glycol (PEG) moieties.

The peptides of the invention may be subjected to one or more modifications for manipulating storage stability, pharmacokinetics, and/or any aspect of the bioactivity of the peptide, such as, e.g., potency, selectivity, and drug interaction. Chemical modification to which the peptides may be subjected includes, without limitation, the conjugation to a peptide of one or more of polyethylene glycol (PEG), monomethoxy-polyethylene glycol, dextran, poly-(N-vinyl pyrrolidone) polyethylene glycol, propylene glycol homopolymers, a polypropylene oxide/ethylene oxide co-polymer, polypropylene glycol, polyoxyethylated polyols (e.g., glycerol) and polyvinyl alcohol, colominic acids or other carbohydrate based polymers, polymers of amino acids, and biotin derivatives. PEG conjugation of proteins at Cys residues is disclosed, e.g., in Goodson, R. J. & Katre, N. V. (1990) Bio/Technology 8, 343 and Kogan, T. P. (1992) Synthetic Comm. 22, 2417.

Modified peptides also can include sequences in which one or more residues are modified (i.e., by phosphorylation, sulfation, acylation, amindation, PEGylation, etc.), and mutants comprising one or more modified residues with respect to a parent sequence. Amino acid sequences may also be modified with a label capable of providing a detectable signal, either directly or indirectly, including, but not limited to, radioisotope, fluorescent, and enzyme labels. Fluorescent labels include, for example, Cy3, Cy5, Alexa, BODIPY, fluorescein (e.g., FluorX, DTAF, and FITC), rhodamine (e.g., TRITC), auramine, Texas Red, AMCA blue, and Lucifer Yellow. Preferred isotope labels include $^{3}$H, $^{14}$C, 32P, $^{35}$S, $^{36}$Cl, $^{51}$Cr, $^{57}$Co, $^{58}$Co, $^{59}$Fe, $^{90}$Y, $^{125}$I, $^{131}$I, and $^{286}$Re. Preferred enzyme labels include peroxidase, β-glucuronidase, β-D-glucosidase, β-D-galactosidase, urease, glucose oxidase plus peroxidase, and alkaline phosphatase (see, e.g., U.S. Pat. Nos. 3,654,090; 3,850,752 and 4,016, 043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), are known in the art, and are commercially available (see, e.g., ABC kit, Vector Laboratories, Inc., Burlingame, Calif.; NEN® Life Science Products, Inc., Boston, Mass.).

In an embodiment, the peptide, variant and/or composition is modified to increase drug performance ability. In an embodiment, the peptide, variant and/or composition is modified to increase stability, permeability, maintain potency, avoid toxicity and/or to increase half-life. The modification may be as described above. For example, the modification may be to protect the N and C-terminus, it may be a modified amino acid, cyclisation, replacement of an amino acid, and/or conjugation to macromolecules or large polymers or long life plasma proteins. Strategies to extend a half-life may be as described by Strohl, et al (BioDrugs, 2015), Schlapschy, et al (Protein Eng Des Sel. 2013), Podust, V N, et al (Protein Eng Des Sel. 2013), Zhang, L et al (Curr Med Chem. 2012), Gaberc-Porekar, V, et al (Curr Opin Drug Discov Devel. 2008). Examples include using PEGylation, lipidation (covalent binding of fatty acids to peptide side chains), fusion to Fc domains and human serum albumin, fusion with a hydrophilic amino acid polymer, e.g. XTEN or PAS, and/or fusion with half-life extension proteins.

Peptides or proteins can comprise weak sites in their sequence which are prone to undergoing proteolytic breakage when in a proteolytic enriched environment, e.g. in the blood or gastrointestinal tract. In an embodiment, the peptide, variant and/or composition comprises a modification of one or more weak sites such that the peptide, variant and/or composition does not undergo proteolytic breakdown/cleavage or undergoes a decreased amount of proteolytic breakdown/cleavage compared to an unmodified peptide or protein. Thus, the peptide may modified to increase the resistance of the modified peptide to proteolytic degradation to mammalian gastrointertinal proteases. Suitable modifications are described in Diao et al (Clinical pharmacokinetics 52.10 (2013): 855-868).

Modification of peptides to extend the in-vivo half-life of the peptide is described in the literature, for example:

*Strategies to improve plasma half life time of peptide and protein drugs.* Werle M, Bernkop-Schnürch A. Amino Acids. 2006 June; 30(4):351-67.

Due to the obvious advantages of long-acting peptide and protein drugs, strategies to prolong plasma half life time of such compounds are highly on demand. Short plasma half life times are commonly due to fast renal clearance as well as to enzymatic degradation occurring during systemic circulation. Modifications of the peptide/protein can lead to prolonged plasma half life times. By shortening the overall amino acid amount of somatostatin and replacing L:-analogue amino acids with D:-amino acids, plasma half life time of the derivate octreotide was 1.5 hours in comparison to only few minutes of somatostatin. A PEG(2,40 K) conjugate of INF-alpha-2b exhibited a 330-fold prolonged plasma half life time compared to the native protein. It was the aim of this review to provide an overview of possible strategies to prolong plasma half life time such as modification of N- and C-terminus or PEGylation as well as methods to evaluate the effectiveness of drug modifications. Furthermore, fundamental data about most important proteolytic enzymes of human blood, liver and kidney as well as their cleavage specificity and inhibitors for them are provided in order to predict enzymatic cleavage of peptide and protein drugs during systemic circulation.

*Strategic Approaches to Optimizing Peptide* ADME Properties. Li Di AAPS J. 2015 January; 17(1): 134-143.

Strategies to Stabilize Peptides from Proteolysis

Many approaches are available to enhance stability of peptides through structure modification. Some approaches not only improve stability, but also enhance other ADME properties, e.g., cyclization can increase stability and permeability; conjugation to macromolecules can improve stability and reduce renal clearance. It is important to maintain potency and avoid toxicity while improving stability and ADME properties of peptides.

Protecting N- and C-terminus

A number of proteolytic enzymes in blood/plasma, liver or kidney are exopeptidases, aminopeptidases and carboxypeptidases and they break down peptide sequences from the N- and C-termini. Modification of the N- or/and C-termini can often improve peptide stability. Many examples have reported that N-acetylation, and C-amidation increase resistance to proteolysis.

Replacing L-amino acids with D-amino acids

Substituting natural L-amino acids with nonnatural D-amino acids decreases the substrate recognition and binding affinity of proteolytic enzymes and increases stability. One example is vasopressin, which contains an L-Arg and has a half-life of 10-35 min in humans. The D-Arg analog, desmopressin, has a half-life of 3.7 h in healthy human volunteers. In the study of a bicyclic peptide inhibitor of the cancer-related protease urokinase-type plasminogen activator (uPA), replacement of a specific glycine with a D-serine not only improves potency by 1.8-fold but also increases stability by 4-fold in mouse plasma.

Modification of amino acids

Modification of natural amino acids can improve the stability of peptides by introducing steric hindrance or disrupting enzyme recognition. For example, gonadotropin-releasing hormone has a very short half-life (minutes), while buserelin, in which one Gly is replaced with a t-butyl-D-Ser and another Gly is substituted by ethylamide, has a much longer half-life in humans.

Cyclization

Cyclization introduces conformation constraint, reduces the flexibility of peptides, and increases stability and permeability. Depending on the functional groups, peptides can be cyclized head-to-tail, head/tail-to-side-chain, or side-chain-to-side-chain. Cyclization is commonly accomplished through lactamization, lactonization, and sulfide-based bridges. Disulfide bridges create folding and conformational constraints that can improve potency, selectivity, and stability. A number of disulfide bond-rich peptides are on the market or in preclinical or clinical development, e.g., linaclotide, lepirudin, and ziconotide.

Conjugation to Macromolecules

Conjugation to macromolecules (e.g., polyethylene glycol (PEG), albumin) is an effective strategy to improve stability of peptides and reduce renal clearance.

Renal Clearance

Many peptides exhibit promising in vitro pharmacological activity but fail to demonstrate in vivo efficacy due to very short in vivo half-life (minutes). The rapid clearance and short half-life of peptides hamper their development into successful drugs. The main causes of rapid clearance of peptides from systemic circulation are enzymatic proteolysis or/and renal clearance. The glomeruli have a pore size of ~8 nm, and hydrophilic peptides with MW<2-kDa are susceptible to rapid filtration through the glomeruli of the kidney. Since peptides are not easily reabsorbed through the renal tubule, they frequently have high renal clearance and short half-life. Other minor routes of peptide clearance are endocytosis and degradation by proteasome and the liver. Comparison between systemic and renal clearance in animal models provides useful information on whether renal clearance is likely to be a major elimination pathway.

For renal-impaired patients, dose adjustment may be needed for peptide drugs to avoid accumulation and higher drug exposure, as inappropriate dosing in patients with renal dysfunction can cause toxicity or ineffective therapy. Several strategies have been developed to reduce peptide renal clearance and prolong half-life. These will be reviewed next.

Increase plasma protein binding

Renal clearance of peptides is reduced when they are bound to membrane proteins or serum proteins. An example is the cyclic peptide drug octreotide, a treatment for endocrine tumors, which has about 100 min half-life in humans due to binding to lipoproteins (fraction unbound 0.65)

Covalent Linkage to Albumin-Binding Small Molecules

Covalently attaching albumin-binding small molecules to peptides can reduce glomerular filtration, improve proteolytic stability, and prolong half-life by indirectly interacting with albumin through the highly bound small molecules.

Conjugation to Large Polymers

Conjugation of peptides to large synthetic or natural polymers or carbohydrates can increase their molecular weight and hydrodynamic volume, thus reducing their renal clearance. The common polymers used for peptide conjugation are PEG, polysialic acid (PSA), and hydroxyethyl starch (HES).

Fusion to Long-Live Plasma Proteins

Plasma proteins, such as albumin and immunoglobulin (IgG) fragments, have long half-lives of 19-21 days in humans. Because of the high MW (67-150 kDa), these proteins have low renal clearance, and their binding to neonatal Fc receptor (FcRn) reduces the elimination through pinocytosis by the vascular epithelium. Covalent linkage of peptides to albumin or IgG fragments can reduce renal clearance and prolong half-life.

Fusion Proteins for Half-Life Extension of Biologics as a Strategy to Make Biobetters William R. Strohl BioDrugs. 2015; 29(4): 215-239.

Schlapschy, M, Binder, U, Borger, C et al. PASYlation: a biological alternative to PEGylation for extending the plasma half-life of pharmaceutically active proteins. Protein Eng Des Sel. 2013; 26(8):489-501.

Podust, V N, Sim, B C, Kothari, D et al. Extension of in vivo half-life of biologically active peptides via chemical conjugation to XTEN protein polymer. Protein Eng Des Sel. 2013; 26(11):743-53.

Zhang, L, Bulaj, G. Converting Peptides into Drug Leads by Lipidation. Curr Med Chem. 2012; 19(11):1602-18.

Gaberc-Porekar, V, Zore, I, Podobnik, B et al. Obstacles and pitfalls in the PEGylation of therapeutic proteins. Curr Opin Drug Discov Devel. 2008; 11(2):242-50.

By Dr Ronald V. Swanson—Long live peptides evolution of peptide half-life extension technologies and emerging hybrid approaches. From Drug Discovery World on line. Spring 2014

PEGylation

The attachment of long chains of the hydrophilic polymer polyethylene glycol to molecules of interest, PEGylation was originally conceived as a modification to prevent the recognition of foreign proteins by the immune system and, thereby, enable their utility as therapeutics. Once formed, antibodies against unmodified drugs can rapidly neutralise and clear protein drugs. Unexpectedly, PEGylation improved the pharmacokinetics of the proteins even in the absence of anti-drug antibodies). Simply by making drug molecules larger, PEGylation led to the drug being filtered more slowly by the kidneys. The empirical observation that increasing size or hydrodynamic radius led to reduced renal clearance and increased half-life then became the dominant rationale for the PEGylation of protein and peptide drugs. PEGylation can have a variety of effects on the molecule including making proteins or peptides more water-soluble and protecting them from degradation by proteolytic enzymes. PEGylation can also impact the binding of therapeutic proteins to their cognate cellular receptors, usually reducing the affinity. Changes in the size, structure and attachment mode of PEG polymers can affect the biological activity of the attached drug.

The first-generation PEGylation methods were filled with challenges. However, the chemistry of PEGylation is quite simple. The process involves the covalent attachment of polyethylene glycol chains to reactive side chains of a protein or peptide. For example, PEG is easily attached to the -amino groups of lysine on the surface of proteins or peptides2. The reaction is pH-dependent. At high pH (8.0 or higher), lysine side chain amino groups are covalently attached to PEG through N-hydroxy succinimides. This method typically results in a family of products containing different numbers of PEG chains attached at different sites on a protein rather than a single discrete product3. The first approved PEGylated pharmaceuticals were Pegademase bovine (PEGylated bovine adenosine deamidase) as enzyme replacement therapy for severe combined immunodeficiency and Pegaspargase (PEGylated asparaginase) for treatment of acute lymphoblastic leukaemia1. These drugs were complex mixtures of various PEGylated species, but with improved properties for therapy over native enzymes, including increased serum half-life and decreased immunogenicity of the proteins. Due to the inherent polydispersity of the PEG, quality and batch-to-batch reproducibility was difficult. Despite this limitation, two PEGylated interferons, (Peginterferon alfa-2b and Peginterferon alfa-2a) that are heterogeneous populations of numerous mono-PEGylated positional isomers, have been FDA-approved for the treatment of hepatitis C. These drugs were brought to market in 2001 and 2002, respectively.

A variety of enhancements and variations have been made to the fundamental PEGylation technology. Second-generation PEGylation processes introduced the use of branched structures as well as alternative chemistries for PEG attachment. In particular, PEGs with cysteine reactive groups such as maleimide or iodoacetamide allow the targeting of the PEGylation to a single residue within a peptide or protein reducing the heterogeneity of the final product but not eliminating it due to the polydispersity of the PEG itself.

While the original rationale for PEGylation was to reduce immunogenicity; nevertheless, there have been a few examples of immunogenic PEGylated proteins. One example is PEGylated urate oxidase, an enzyme that lowers the plasma urate level in patients with gout. In clinical trials, a relatively high percentage of patients with gout did not respond to the therapy and developed antibodies that were specific for PEG, but not for the uricase protein2. PEGylated liposomes, also generally thought to be non-immunogenic, have been found to be immunogenic in some studies. PEGylated liposomes elicit a strong anti-PEG immunoglobulin M (IgM) response. In addition, multiple injections of PEG-glucuronidase were shown to elicit the generation of specific anti-PEG IgM antibodies, thus accelerating the clearance of PEG-modified proteins from the body.

A major potential drawback of using PEG as a modifier is that it is non-biodegradable. The US Food and Drug Administration (FDA) has approved PEG for use as a vehicle in pharmaceuticals, including injectable, topical, rectal and nasal formulations. PEG shows little toxicity and is eliminated from the body intact by either the kidneys (for PEGs<30 kDa) or in the feces (for PEGs>20 kDa)1. Repeated administration of some PEGylated proteins to animals has resulted in observations of renal tubular cellular vacuolation. Recently, vacuolation of choroid plexus epithelial cells has also been seen in toxicity studies with proteins conjugated with large (≥40 kDa) PEGs. The choroid plexus epithelial cells produce cerebrospinal fluid and form the blood CSF barrier. The long-term negative consequences of cellular vacuolation are unclear, but it does represent an undesirable consequence for some potential therapeutics. One possible alternative would be substitution of a biodegradable polymer in place of PEG. Polymers, such as hydroxyethyl starch (HES) are a possible alternative. HES is non-toxic and biodegradable and used as a blood expander. A process of HESylation would function similarly to PEGylation in reducing renal clearance through increasing a peptide's hydrodynamic radius but may confer a lower propensity for accumulation due to biodegradability. However, HES and other proposed biodegradable polymer PEG alternatives are, like PEG, polydisperse making characterisation of the final product and metabolites difficult. One emerging solution which mitigates both concerns is to use defined polypeptides as the polymer component; this approach will be discussed later in the article.

Lipidation

A second major chemical modification method to increase peptide half-life is lipidation which involves the covalent binding of fatty acids to peptide side chains4. Originally conceived of and developed as a method for extending the half-life of insulin, lipidation shares the same basic mechanism of half-life extension as PEGylation, namely increasing the hydrodynamic radius to reduce renal filtration. However, the lipid moiety is itself relatively small and the effect is mediated indirectly through the non-covalent binding of the lipid moiety to circulating albumin. A large (67 KDa) and highly abundant protein in human serum (35-50 g/L), albumin naturally functions to transport molecules, including lipids, throughout the body. Binding to plasma proteins can also protect the peptide from attacks by peptidases through steric hindrance, again akin to what is seen with PEGylation.

One consequence of lipidation is that it reduces the water-solubility of the peptide but engineering of the linker between the peptide and the fatty acid can modulate this, for example by the use of glutamate or mini PEGs within the linker. Linker engineering and variation of the lipid moeity can affect self-aggregation which can contribute to increased half-life by slowing down biodistribution, independent of albumin5.

Following the pioneering work with insulin6, lipidation of a variety of peptides has been explored, particularly peptides within the diabetes space including human glucagon-like peptide-1 (GLP-1) analogues, glucose-dependent insulinotropic polypeptide and GLP-1R/Glucagon receptor coagonists among others. Two lipidated peptide drugs are currently FDA-approved for use in humans. These are both long-acting anti-diabetics, the GLP-1 analogue liraglutide and insulin detemir.

A potentially pharmacologically-relevant difference between PEGylation and lipidation is that the therapeutically active peptide is covalently linked to the much larger PEG, whereas the smaller fatty acyl-peptide conjugate is non-covalently associated with the larger albumin, bound and unbound forms existing in equilibrium. This can result in differences in biodistribution that may result in different pharmacology as access to receptors localised in different tissues may elicit differential effects. In some cases, more restricted biodistribution may be desirable, while in others, greater tissue penetration may be important. An interesting variation of the PEG approach which addresses this issue has been developed by Santi et al in which releasable PEG conjugates with predictable cleavage rates are utilised7.

PEGylation and lipidation both confer protection against proteases and peptidases by shielding through steric hindrance and extend circulating half-life through increased hydrodynamic radius, directly or indirectly. Both methods utilise chemical conjugation and are flexible in that they are agnostic to the means used to generate the peptide they are modifying, whether biologically or synthetically produced. An advantage of using synthetic peptides is that they can incorporate non-natural amino acids designed to address a number of specific issues including instability due to known proteolytic cleavage liabilities. They can also be more flexible in terms of the choice of attachment site which is critical if activity or potency is highly dependent on the free termini or a modified residue such as a Cterminal amide.

Classical Genetic Fusions: Fc and HSA

Figure 2:
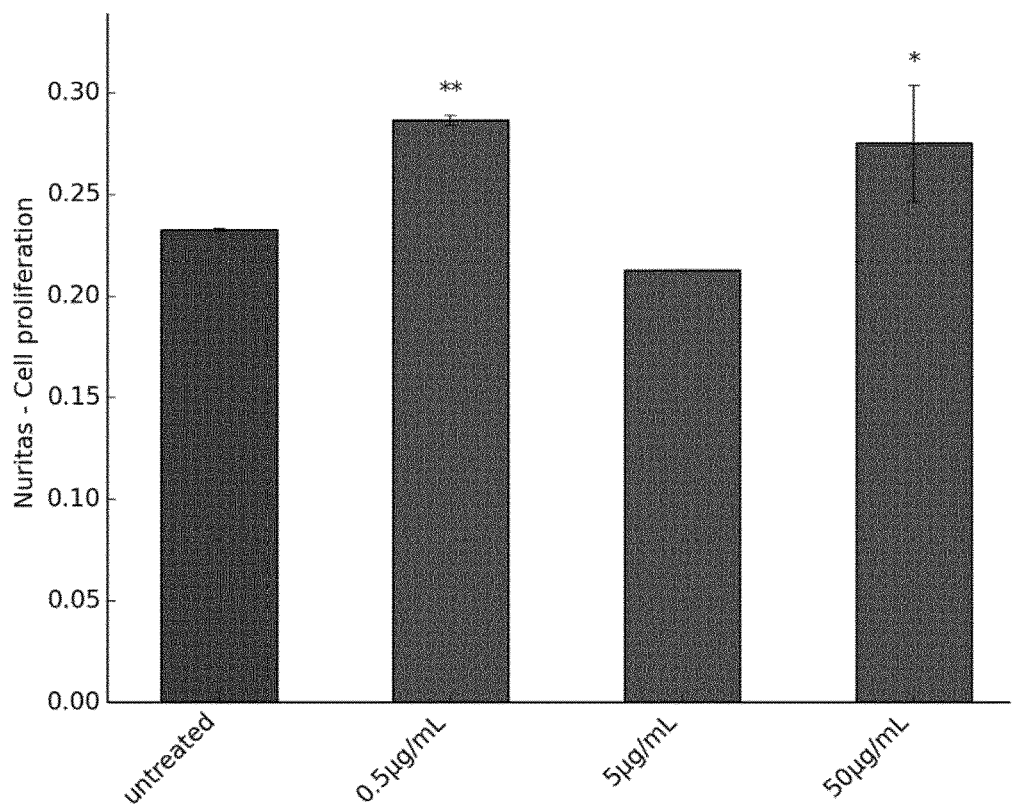
FIG. 2 illustrates the results of a cell proliferation assay using untreated and peptide-treated HACAT cells.

Classical genetic fusions to long-lived serum proteins offer an alternative method of half-life extension distinct from chemical conjugation to PEG or lipids. Two major proteins have traditionally been used as fusion partners: antibody Fc domains and human serum albumin (HAS) (FIG. 2). Fc fusions involve the fusion of peptides, proteins or receptor exodomains to the Fc portion of an antibody. Both Fc and albumin fusions achieve extended half-lives not only by increasing the size of the peptide drug, but both also take advantage of the body's natural recycling mechanism: the neonatal Fc receptor, FcRn. The pH-dependent binding of these proteins to FcRn prevents degradation of the fusion protein in the endosome. Fusions based on these proteins can have half-lives in the range of 3-16 days, much longer than typical PEGylated or lipidated peptides. Fusion to antibody Fc can improve the solubility and stability of the peptide or protein drug. An example of a peptide Fc fusion is dulaglutide, a GLP-1 receptor agonist currently in late-stage clinical trials. Human serum albumin, the same protein exploited by the fatty acylated peptides is the other popular fusion partner. Albiglutide is a GLP-1 receptor agonist based on this platform. A major difference between Fc and albumin is the dimeric nature of Fc versus the monomeric structure of HAS leading to presentation of a fused peptide as a dimer or a monomer depending on the choice of fusion partner. The dimeric nature of a peptide Fc fusion can produce an avidity effect if the target receptors are spaced closely enough together or are themselves dimers. This may be desirable or not depending on the target.

Designed Polypeptide Fusions: XTEN and PAS

An intriguing variation of the recombinant fusion concept has been the development of designed low complexity sequences as fusion partners, basically unstructured, hydrophilic amino acid polymers that are functional analogs of PEG (FIG. 1). The inherent biodegradability of the polypeptide platform makes it attractive as a potentially more benign alternative to PEG. Another advantage is the precise molecular structure of the recombinant molecule in contrast to the polydispersity of PEG. Unlike HSA and Fc peptide fusions, in which the three-dimensional folding of the fusion partner needs to be maintained, the recombinant fusions to unstructured partners can, in many cases, be subjected to higher temperatures or harsh conditions such as HPLC purification.

The most advanced of this class of polypeptides is termed XTEN (Amunix) and is 864 amino acids long and comprised of six amino acids (A, E, G, P, S and T) (FIG. 1)8. Enabled by the biodegradable nature of the polymer, this is much larger than the 40 KDa PEGS typically used and confers a concomitantly greater half-life extension. The fusion of XTEN to peptide drugs results in half-life extension by 60- to 130-fold over native molecules. Two fully recombinantly produced XTENylated products have entered the clinic, namely VRS-859 (Exenatide-XTEN) and VRS-317 (human growth hormone-XTEN). In Phase Ia studies, VRS-859 was found to be well-tolerated and efficacious in patients with Type 2 diabetes. VRS-317 reported superior pharmacokinetic and pharmacodynamic properties compared with previously studied rhGH products and has the potential for once-monthly dosing.

A second polymer based on similar conceptual considerations is PAS (XL-Protein GmbH)9. A random coil polymer comprised of an even more restricted set of only three small uncharged amino acids, proline, alanine and serine (FIG. 1). Whether differences in the biophysical properties of PAS and the highly negatively charged XTEN may contribute to differences in biodistribution and/or in vivo activity is yet unknown but will be revealed as these polypeptides are incorporated into more therapeutics and the behaviour of the fusions characterised.

All the peptide protein fusions, whether the partner is Fc, HSA, XTEN or PAS, are genetically encoded and consequently suffer from similar constraints. One limitation is that only naturally occurring amino acids are incorporated, unlike the methods employing chemical conjugation which allow the use of synthetic peptides incorporating non-natural amino acids. Although methods to overcome this by expanding the genetic code are being developed by companies such as Ambrx or Sutro, they are not yet in wide use. A second limitation is that either the N- or C-terminus of the peptide needs to be fused to the partner. Oftentimes, the peptide termini are involved in receptor interactions and genetic fusion to one or both termini can greatly impair activity. Since the site of PEG or lipid conjugation can be anywhere on the peptide, it can be optimised to maximise biological activity of the resulting therapeutic.

Hybrid Methods Merging Synthetic Peptides with Half-Life Extension Proteins

While genetic fusions have historically offered the potential for greater half-life extension, they lack the advantages afforded by the methods utilising chemical conjugation, PEGylation and lipidation, in terms of flexibility of attachment sites and incorporation of unnatural amino acids or modifications to the peptide backbone. One of the first efforts to merge the advantages of the genetic fusions with chemical conjugation for half-life extension was carried out by researchers at the Scripps Research Institute in La Jolla with the technology which later formed the basis for the biotech company CovX10,11. Using a catalytic aldolase antibody, these researchers developed a platform through which the active site lysine of the antibody forms a reversible covalent enamine bond with a beta-diketone incorporated into a peptide or small molecule. The resulting complex is termed a CovXBody™. This approach combines the functional qualities of a peptide drug or small molecule with the long serum half-life of an antibody, not through a genetic fusion but rather through a chemical linkage. Following the initial demonstration of the technology, researchers expanded upon the use of CovX-Body™ prototype that is based on an integrin targeting peptidomimetic pharmacophore. At least three molecules based on this architecture have entered clinical development: CVX-096, a Glp-1R agonist; CVX-060, an Angiopoietin-2 binding peptide; and CVX-045, a thrombospondin mimetic.

Recently, the XTEN polypeptide has also been used in a chemical conjugation mode12 making it even more directly analogous to PEG. The first example of an XTENylated peptide that was created using this method is GLP2-2G-XTEN in which the peptide is chemically conjugated to the XTEN protein polymer using maleimide-thiol chemistry. The chemically conjugated GLP2-2GXTEN molecules exhibited comparable in vitro activity, in vitro plasma stability and pharmacokinetics in rats comparable to recombinantly-fused GLP2-2G-XTEN.

The number and spacing of reactive groups such as lysine or cysteine side chains in the completely designed sequences of XTEN or PAS polypeptides can be precisely controlled through site-directed changes due to the restricted amino acid sets from which they are composed. This provides an additional degree of flexibility over methods which might utilise Fc or albumin whose sequences naturally contain many reactive groups and stands in contrast to the CovX technology which relies on a reactive residue in a highly specialised active site. In addition, the lack of tertiary structure of XTEN or PAS should provide more flexibility over the conditions and chemistries used in coupling and in the purification of conjugates.

In summary, hybrid peptide half-life extension methods are emerging that combine the advantages and overcome the individual limitations of chemical conjugation and genetic fusions methods. These methods enable the creation of molecules based on recombinant polypeptide-based partners that impart longer half-life but free the therapeutic peptide moieties from the limitations of being composed solely of natural L-amino acids or configured solely as linear, unidirectional polypeptides fused at either the N- or C-terminus, thus opening the door to a wide range of longer acting peptide based drugs.

Pharmaceutical Compositions

A peptide of the invention (including variants and modified peptides) can be combined with one or more carriers (diluents, excipients, and the like) appropriate for one or more intended routes of administration to provide compositions that are pharmaceutically acceptable in the context of preparing a pharmaceutically acceptable composition comprising one or more peptides of the invention.

A peptide of the invention may be, for example, admixed with lactose, sucrose, powders (e.g., starch powder), cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and optionally further tabletted or encapsulated for conventional administration. Alternatively, a peptide of the invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other carriers, adjuvants, and modes of administration are well known in the pharmaceutical arts. A carrier or diluent may include time delay material, such as glyceryl monostearate or glyceryl distearate alone or with a wax, or other functionally similar materials.

Pharmaceutically acceptable carriers generally also include any and all suitable solvents, dispersion media, coatings, antibacterial and antifungal agents, isotonic and absorption delaying agents, and the like that are physiologically compatible with an insulin analog. Examples of pharmaceutically acceptable carriers include water, saline, phosphate buffered saline (PBS), dextrose, glycerol, ethanol, and the like, as well as combinations of any thereof. In many cases, it can be desirable to include isotonic agents, for example, sugars, polyalcohols such as mannitol, sorbitol, or sodium chloride in such a composition. Pharmaceutically acceptable substances such as wetting agents or minor amounts of auxiliary substances such as wetting agents or emulsifying agents, preservatives or buffers, which desirably can enhance the shelf life or effectiveness of the insulin analog, related composition, or combination. Suitability for carriers and other components of pharmaceutical compositions can be determined based on the lack of significant negative impact on the desired biological properties of the insulin analog, related composition, or combination (e.g., less than an about 20%, 15%, 10%, 5%, or 1% reduction in IR binding and/or activation; or ability to reduce blood glucose in a target host).

Compositions, related compositions, and combinations according to the invention may be presented, prepared, and/or administered in a variety of suitable forms. Such forms include, for example, liquid, semi-solid and solid dosage forms, such as liquid solutions (e.g., injectable and infusible solutions), dispersions or suspensions, emulsions, microemulsions, tablets, pills, powders, liposomes, dendrimers and other nanoparticles (see, e.g., Baek et al., Methods Enzymol. 2003; 362:240-9; Nigavekar et al., Pharm Res. 2004 March; 21(3):476-83), microparticles, and suppositories. The optimal form for any peptide of the invention-associated composition depends on the intended mode of administration, the nature of the composition or combination, and therapeutic application or other intended use. Formulations also can include, for example, powders, pastes, ointments, jellies, waxes, oils, lipids, lipid (cationic or anionic) containing vesicles, DNA conjugates, anhydrous absorption pastes, oil-in-water and water-in-oil emulsions, emulsions, carbowax (polyethylene glycols of various molecular weights), semi-solid gels, and semi-solid mixtures containing carbowax. Any of the foregoing mixtures may be appropriate in treatments and therapies in accordance with the present invention, provided that the binding of the peptide to cognate IRs is not significantly inhibited by the formulation and the formulation is physiologically compatible and tolerable with the route of administration. See also, e.g., Powell et al. "Compendium of excipients for parenteral formulations" PDA J Pharm Sci Technol. 52:238-311 (1998) and the citations therein for additional information related to excipients and carriers well known to pharmaceutical chemists.

In a particular aspect, a peptide of the invention is administered in liposomes. In another aspect, a peptide of the invention administered in liposomes with one or more secondary agents, such as one or more anti-diabetes drugs.

Compositions of the invention also include compositions comprising any suitable combination of a peptide of the invention and a suitable salt therefor. Any suitable salt, such as an alkaline earth metal salt in any suitable form (e.g., a buffer salt), can be used in the stabilization of the peptide of the invention (preferably the amount of salt is such that oxidation and/or precipitation of the peptide is avoided). Suitable salts typically include sodium chloride, sodium succinate, sodium sulfate, potassium chloride, magnesium chloride, magnesium sulfate, and calcium chloride. Compositions comprising a base and one or more peptides of the invention also are provided.

A typical mode for delivery of compositions of the invention is by parenteral administration (e.g., intravenous, subcutaneous, intraperitoneal, and/or intramuscular administration). In one aspect, a composition or peptide of the invention is administered to a human patient by intravenous infusion or injection. In another aspect, a composition or peptide of the invention is administered by intramuscular or subcutaneous injection. As indicated above, intratumor administration also may be useful in certain therapeutic regimens.

Thus, peptides of the invention may be formulated in, for example, solid formulations (including, e.g., granules, powders, projectile particles, or suppositories), semisolid forms (gels, creams, etc.), or in liquid forms (e.g., solutions, suspension, or emulsions). A composition or peptide of the invention may be applied in a variety of solutions. Suitable solutions for use in accordance with the invention typically are sterile, dissolve sufficient amounts of the peptide of the invention and other components of the composition, stable under conditions for manufacture and storage, and not harmful to the subject for the proposed application. A peptide of the invention may be subjected to conventional pharmaceutical operations such as sterilization and/or may contain conventional adjuvants, such as preservatives, stabilizers, wetting agents, emulsifiers, buffers etc. A composition also can be formulated as a solution, microemulsion, dispersion, powder, macroemulsion, liposome, or other ordered structure suitable to high drug concentration. Desirable fluidity properties of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. These and other components of a pharmaceutically acceptable composition of the invention can impart advantageous properties such as improved transfer, delivery, tolerance, and the like.

A composition for pharmaceutical use can include various diluents, fillers, salts, buffers, detergents (e.g., a nonionic detergent, such as Tween-80), stabilizers (e.g., sugars or protein-free amino acids), preservatives, tissue fixatives, solubilizers, and/or other materials suitable for inclusion in a composition for pharmaceutical use. Examples of suitable components also are described in, e.g., Berge et al., J. Pharm. Sci., 6661), 1-19 (1977); Wang and Hanson, J. Parenteral. Sci. Tech: 42, S4-S6 (1988); U.S. Pat. Nos. 6,165,779 and 6,225,289; and other documents cited herein. Such a pharmaceutical composition also can include preservatives, antioxidants, or other additives known to those of skill in the art. Additional pharmaceutically acceptable carriers are known in the art and described in, e.g., Urquhart et al., Lancet, 16, 367 (1980), Lieberman et al., Pharmaceutical Dosage Forms—Disperse Systems (2nd ed., vol. 3, 1998); Ansel et al., Pharmaceutical Dosage Forms & Drug Delivery Systems (7th ed. 2000); Martindale, The Extra Pharmacopeia (31st edition), Remington's Pharmaceutical Sciences (16th-20th editions); The Pharmacological Basis Of Therapeutics, Goodman and Gilman, Eds. (9th ed.—1996); Wilson and Gisvolds' TEXTBOOK OF ORGANIC MEDICINAL AND PHARMACEUTICAL CHEMISTRY, Delgado and Remers, Eds. (10th ed.—1998), and U.S. Pat. Nos. 5,708,025 and 5,994,106. Principles of formulating pharmaceutically acceptable compositions also are described in, e.g., Platt, Clin. Lab Med., 7:289-99 (1987), Aulton, Pharmaceutics: The Science Of Dosage Form Design, Churchill Livingstone (New York) (1988), EXTEMPORANEOUS ORAL LIQUID DOSAGE PREPARATIONS, CSHP (1998), and "Drug Dosage," J. Kans. Med. Soc., 70 (I), 30-32 (1969). Additional pharmaceutically acceptable carriers particularly suitable for administration of peptide or compositions of the invention and related compositions (e.g., compositions comprising peptides of the invention-encoding nucleic acids or peptide of the invention-encoding nucleic acid comprising vectors) are described in, for example, International Patent Application WO 98/32859.

Peptides or compositions of the invention can be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid, and combinations of any thereof, so as to provide such a composition. Methods for the preparation of such compositions are known. See, e.g., Sustained and Controlled Release Drug Delivery Systems, J. R. Robinson, ed., Marcel Dekker, Inc., New York, 1978

In another aspect, compositions of the invention orally administered, for example, with an inert diluent or an assimilable edible carrier (specific oral administration formulations and methods are also separately described elsewhere herein). The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

The preparation of pharmaceutical compositions that contain peptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically (i.e., physiologically) acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH-buffering agents, which enhance the effectiveness of the active ingredient.

A peptide of the invention can be formulated into a pharmaceutical composition as neutralized physiologically acceptable salt forms. Suitable salts include the acid addition salts (i.e., formed with the free amino groups of the peptide molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In the case of combination compositions (discussed further herein), a peptide of the invention can be co-formulated with and/or coadministered with one or more additional therapeutic agents (e.g., an anti-diabetic agent such as an insulin, an insulin analogue, metformin or other anti-diabetic biguanide, a glucagon receptor antagonist, sulfonylurea, a thiazolidinedione, an alpha-glucosidase inhibitor, a meglitinide, a glucagon-like peptide-1 (GLP-1), a GLP-1 analog, etc.). Such combination therapies may require lower dosages of the peptide of the invention and/or the co-administered agents, so as to avoid possible toxicities or complications associated with the various monotherapies.

Therapeutic Applications

As indicated above, a peptide or composition of the invention can be administered individually or in combination with other pharmacologically active agents. It will be understood that such combination therapy encompasses different therapeutic regimens, including, without limitation, administration of multiple agents together in a single dosage form or in distinct, individual dosage forms. If the agents are present in different dosage forms, administration may be simultaneous or near-simultaneous or may follow any predetermined regimen that encompasses administration of the different agents.

For example, when used to treat diabetes or other diseases or syndromes associated with a decreased response or production of insulin, hyperlipidemia, obesity, appetite-related syndromes, and the like, the peptides of the invention may be advantageously administered in a combination treatment regimen with one or more agents, including, without limitation, insulin, insulin analogues, insulin derivatives, glucagon-like peptide-1 or -2 (GLP-1, GLP-2), derivatives or analogues of GLP-1 or GLP-2 (such as are disclosed, e.g., in WO 00/55119). It will be understood that an "analogue" of insulin, GLP-1, or GLP-2 as used herein refers to a peptide containing one or more amino acid substitutions relative to the native sequence of insulin, GLP-1, or GLP-2, as applicable; and "derivative" of insulin, GLP-1, or GLP-2 as used herein refers to a native or analogue insulin, GLP-1, or GLP-2 peptide that has undergone one or more additional chemical modifications of the amino acid sequence, in particular relative to the natural sequence. Insulin derivatives and analogues are disclosed, e.g., in U.S. Pat. Nos. 5,656,722, 5,750,497, 6,251,856, and 6,268,335. In some embodiments, the combination agent is one of LysB29(ε-myristoyl)des(B30) human insulin, LysB29(ε-tetradecanoyl)des(B30) human insulin and B29-Nε-(N-lithocolyl-γ-glutamyl)-des(B30) human insulin. Also suitable for combination therapy are non-peptide antihyperglycemic agents, antihyperlipidemic agents, and the like such as those well-known in the art.

In one embodiment, the invention encompasses methods of treating diabetes or related syndromes or associated conditions (e.g., reducing the rate of glucose level-related and/or diabetes-related stroke, heart disease, kidney disease, blindness, and/or loss of sensation in the limbs) comprising delivering an effective amount of at least one peptide of the invention (by gene expression, by delivery of a homogenous peptide, or typically by administration of a pharmaceutically acceptable composition comprising one or more peptides and one or more pharmaceutically acceptable carriers as described above. In another aspect, the invention provides the use of a peptide or composition of the invention (such as a combination composition) in the manufacture of a medicament used in the treatment of type 1 or type 2 diabetes.

A peptide of the invention can generally be used in the treatment of both Type 1 and Type 2, i.e., insulin dependent diabetes mellitus (IDDM) and non-insulin dependent diabetes mellitus (NIDDM).

In an exemplary combination therapy aspect, the invention provides a method of treating diabetes (e.g., reducing one or more symptoms associated therewith in a host and/or providing to a host an amount of a composition that has been demonstrated to be therapeutically effective in at least a substantial proportion of a population of similar hosts) comprising delivering a first amount of a peptide or composition of the invention and a second amount of a long-acting insulin analogue, such as, e.g., LysB29(ε-myristoyl)des(B30) human insulin, LysB29(ε-tetradecanoyl)des(B30) human insulin or B29-Nε-(N-lithocolyl-γ-glutamyl)-des(B30) human insulin, wherein the first and second amounts together are effective for treating the syndrome. As used herein, a long-acting insulin analogue is one that exhibits a protracted profile of action relative to native human insulin, as disclosed, e.g., in U.S. Pat. No. 6,451,970. In another aspect, the invention provides the use of a combination composition comprising a therapeutically effective combination of at least one peptide or composition of the invention and at least one insulin or insulin analog in the manufacture of a medicament used in the treatment of disease, such as in the treatment of type 1 or type 2 diabetes. Similar compositions comprising combinations of one or more peptides or compositions of the invention and one or more long and/or short-acting insulin analogs also can be suitable for therapeutic methods, such as the treatment of diabetes.

In one aspect, the invention provides a method provides a method of treating symptoms and/or underlying conditions associated with Type 2 diabetes in a patient in need thereof (due to diagnosis of the disease and/or substantial risk of development thereof) comprising delivering to the patient a therapeutically and/or prophylactically effective amount of a peptide or composition of the invention so as to treat such symptoms and/or conditions. In a particular aspect, the invention provides a method of treating a patient having Type 2 diabetes and high insulin blood levels (hyperinsulinemia). In one such aspect, the patient is obese. In another aspect, the patient also or alternatively comprises an insulin resistant genotype/mutation.

In another aspect, the invention provides a method of reducing blood pressure in a patient having insulin/IR-associated high blood pressure comprising administering or otherwise delivering a therapeutically effective amount of a peptide or composition of the invention so as to reduce blood pressure in the patient.

In another aspect, the invention provides a method of treating the symptoms and/or underlying conditions of Syndrome X or an aspect thereof in a patient (e.g., hyperlipdemia, hypertension, and/or obesity) comprising administering or otherwise delivering a therapeutically and/or prophylactically effective amount of a peptide or composition of the invention to the patient so as to treat Syndrome X or a Syndrome X condition.

In still another aspect, the invention provides a method of treating a non-diabetes IR-mediated condition, disorder, or disease in a patient, such as an IR-associated neurodegenerative disease; an IR-associated non-diabetes autoimmune disease; etc., comprising administering a therapeutically or prophylactically effective amount of a peptide or composition of the invention to the patient to treat such conditions/symptoms.

In another aspect, the invention provides a method of preventing weight gain in a patient in need thereof comprising administering a therapeutically or prophylactically effective amount of a peptide or composition of the invention to the patient so as to prevent IR-associated weight gain.

In a related aspect, the invention provides a method of treating obesity comprising administering a therapeutically or prophylactically effective amount of a peptide or composition of the invention to the patient to treat obesity (by stabilizing and/or reducing the weight of the patient) or a condition related thereto.

In another aspect, the invention provides a method of treating a patient suffering from a disease condition associated with or caused by hyperinsulinaemia, hypoglycaemia, hypokalaemia, and/or hypophosphataemia comprising administering (or otherwise delivering—as is the case throughout) a therapeutically or prophylactically effective amount of a peptide or composition of the invention to the patient to treat such conditions/symptoms. The present invention further relates to method for treating glycaemic-related diseases or disorders, comprising the administration of insulin derivatives or insulin conjugates. Glycaemic-related diseases or disorders include diabetes of Type I and II, and gestational diabetes. Also, cystic fibrosis, polycystic ovary syndrome, pancreatitis and other pancreas-related diseases may also be treated by the administration of insulin derivatives or insulin conjugates of the present invention. Insulin is also known as a growth factor and therefore, the insulin derivatives or insulin conjugates of the present invention can be useful in topical administration for wound healing and other related indications.

In another aspect, the invention provides the use of a peptide or composition of the invention (such as a combination composition) in the manufacture of a medicament used in the treatment of any of the foregoing conditions.

In one general aspect, the invention provides a method of modulating glucose levels in an individual comprising administering a physiologically effective amount of a peptide or composition of the invention so as to detectably modulate glucose levels in the patient. In another aspect, the invention provides the use of a peptide or composition of the invention (such as a combination composition) in the manufacture of a medicament used in the reducing of blood glucose levels.

In another general aspect, the invention provides a method of mediating IR activity comprising administering a physiologically effective amount of a peptide or composition of the invention such that responsive IR on IR-presenting cells is bound in an amount and under conditions sufficient to induce, promote, enhance, and/or otherwise modulate an IR-mediated activity or response. For example, a peptide of the invention can be delivered to a host to bind to Site 1 or Site 2, so as to direct insulin or insulin analog molecules to the other site so as to modify the profile of an insulin or insulin analog treatment.

In yet a further facet, the invention provides a method of modulating nitric oxide production levels in a patient, such as in the endothelial cells of a patient; mediating RAS, RAF, MEK, and/or mitogen-activated protein (MAP) kinase pathways; modulating vascular tissue growth and/or smooth muscle cell, monocyte, macrophage, and/or endothelial cell growth and/or migration; stimulate production of plasminogen activator inhibitor type 1 (PAI-1); modulate endothelin production; modulate IR-associated proatherosclerotic pathway biological events; modulate IR-associated inflammation; treat and/or reduce the risk of arterial injury; treat and/or prevent atherosclerosis; and/or reduce IR-associated inflammation molecules, such as LDL cholesterol in blood vessel walls of a patient by delivering or otherwise administering a therapeutically or prophylactically effective amount of a peptide or composition of the invention to the patient to induce, promote, and/or enhance such physiological responses.

The peptides and compositions of the invention may also be employed to treat catabolic wasting (for example cachexia and sarcopenia), and for non-therapeutic use in increasing muscle mass, for example in an athlete, sportsperson or bodybuilder. Peptides are also used for their anabolic effect on an athlete's muscle mass. (GHRP means growth hormone releasing hexapeptide, a type of growth hormone releasing hormone).

This can be useful in a couple of ways. Obviously an athlete will need to heal quickly and be productive soon after an injury. Peptides will help the muscle or soft tissue in this rebuilding healing process. Supplements that provide an anabolic effect could also be used during pre-season and other periods where building muscle mass is important. Muscle mass can be built quickly because the athlete can make small tears in a muscle and have it heal on a rapid schedule to continuously repeat the process—the end effect being increased muscle mass and reduced body fat in a shorter timeframe. The bodybuilding community use peptides that are most effective in this second way as newer peptides don't come with the side-effects of anabolic steroids.

Exemplary Dosages and Administration Strategies

As described above, compositions of the invention may include a "therapeutically effective amount" or a "prophylactically effective amount" of a peptide of the invention (or first and second amounts in the case of a combination composition comprising a peptide of the invention and a second component; first, second, and third amounts in the case of a combination composition comprising two peptides of invention and a secondary agent or a peptide of the invention and two secondary agents; etc.). To better illustrate particular aspects, a detailed discussion of dosage principles is further provided here.

In practicing the invention, the amount or dosage range of the peptide of the invention employed typically is one that effectively induces, promotes, or enhances a physiological response associated with peptide of the invention binding of a cognate IR. In one aspect, the dosage range is selected such that the peptide of the invention employed induces, promotes, or enhances a medially significant effect in a patient suffering from or being at substantial risk of developing a condition associated that is at least in part modulated by IR activity, such as, e.g., a form of diabetes, which effect is associated with the activation, signaling, and/or biological modification (e.g., phosphorylation) of the cognate IR.

In still another aspect, a daily dosage of active ingredient (e.g., peptide of the invention) of about 0.01 to 100 milligrams per kilogram of body weight is provided to a patient. Ordinarily, about 1 to about 5 or about 1 to about 10 milligrams per kilogram per day given in divided doses of about 1 to about 6 times a day or in sustained release form may be effective to obtain desired results.

As a non-limiting example, treatment of IR-associated pathologies in humans or animals can be provided by administration of a daily dosage of peptide of the invention in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every about 24, 12, 8, 6, 4, or 2 hours, or any combination thereof.

In one aspect, the inventive methods comprise administering or otherwise delivering two different peptides of the invention over a period of one month, the beginning of the therapy involving the second peptide of the invention peptide of the invention or at any time when a significant immune response to the first peptide of the invention develops in the host, such that the continued use of the first peptide of the invention has become detrimental to the patient.

EXAMPLES

The peptide referred to in the Examples is a peptide having a sequence of SEQ ID NO.1.

Example 1

Cell Proliferation Assay
Study Description
BrDu is incorporated into newly synthesised DNA strands of actively proliferating cells. Following partial denaturation of double stranded DNA, BrDu is detected immunochemically allowing the assessment of the population of cells which are synthesizing DNA.

Methodology
Human Dermal Fibroblasts (HDF—Sigma 10605a) were seeded in a 96 well plate at 10,000 cells per well in DMEM containing 10% fetal calf serum (FCS), 1% Pen/strep, 1% L-glutamine and allowed to adhere for 24 h.

Following the initial 24 h incubation the cells were incubated with 5 µg/ml, 0.5 µg/ml or 0.05 µg/ml synthetic peptide for 24 h respectively.

After 18 h incubation with synthetic peptides 20 µl BrDu reagent was added to each well. At 24 h incubation the cells were fixed and the amount of 2-DG6P was measured using the BrdU Cell Proliferation Assay, all steps were carried out according to the manufacturer's instructions.

This experiment was then repeated using HACAT cells.
Results
The results were calculated as a percentage of the untreated control. An increase in optical density reading indicates greater incorporation of BrDu and increase cell proliferation as illustrated by FIGS. 1 (HDF cells) and 2 (HACAT cells). As illustrated by FIGS. 1 and 2, samples stimulated with the peptide of the invention showed an increase in cell proliferation compared with untreated control.
Conclusion
These results demonstrate the efficacy of the peptide to facilitate cell proliferation.

Example 2

Collagen Production Assay
Study Description Hydroxyproline in tissue preparations is a direct measure of the amount of collagen present. FIRE-LISA Human Hydroxyproline ELISA kit assay is designed to measure hydroxyproline in tissue or peptide compositions.
Methodology
Human Dermal Fibroblasts (HDF Sigma 10605a) were seeded in 24 well plates at 50,000 cells per well in DMEM containing 10% fetal calf serum (FCS), 1% Pen/strep, 1% L-glutamine and allowed to adhere for 24 h.

Following the initial 24 h incubation the cells were incubated with 5 µg/ml, 1 µg/ml or 0.1 µg/ml synthetic peptide for 96 h respectively.

Figure 3:
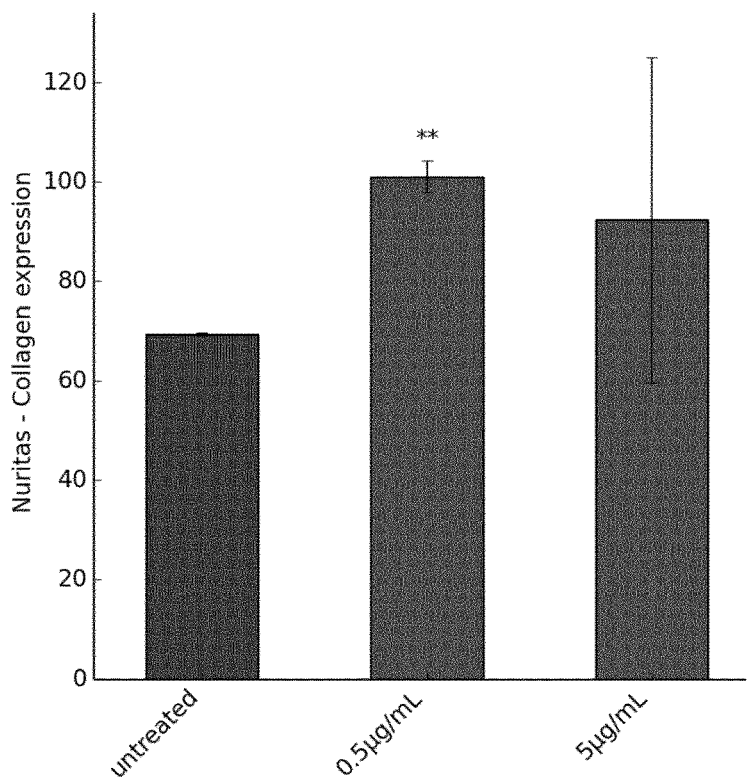
FIG. 3 illustrates the results of a collagen expression assay using untreated and peptide-treated Human Dermal Fibroblasts (HDF).

After treatment, the cell supernatant was removed and centrifuged. 50 µl of each supernatant was assayed using the FIRELISA Human Hydroxyproline ELISA kit. All steps were carried out according to the manufacturer's instructions.
Results
Results were calculated as a percentage of the untreated control. An increase in optical density reading indicates an increase collagen content. An increase in collagen production compared with untreated control was seen as illustrated by FIG. 3.
Conclusion
These results demonstrate the efficacy of the peptide to facilitate collagen production.

Example 3

Elastin Production Assay
Study Description
Elastin is a highly elastic protein in connective tissue and allows many tissues in the body to resume their shape after stretching or contracting. FIRELISA Human Elastin ELISA kit assay is designed to measure Elastin in tissue or protein/peptide compositions.

Methodology

Human Dermal Fibroblasts (HDF) were seeded in 24 well plates at 50,000 cells per well in DMEM containing 10% fetal calf serum (FCS), 1% Pen/strep, 1% L-glutamine and allowed to adhere for 24 h.

Following the initial 24 h incubation the cells were incubated with 5 µg/ml, 1 µg/ml or 0.1 µg/ml synthetic peptide for 96 h respectively.

After treatment, the cells were lysed using cell lysis buffer and sonicated for 10 seconds. The lysed cells were centrifuged and the supernatant was removed from each sample. Total protein concentration was determined using a BCA assay. Each sample was diluted in assay buffer to contain 10 µg total protein. 50 µl of each sample was then assayed using the FIRELISA Human Elastin ELISA kit. All steps were carried out according to the manufacturer's instructions.

Results

Figure 4:
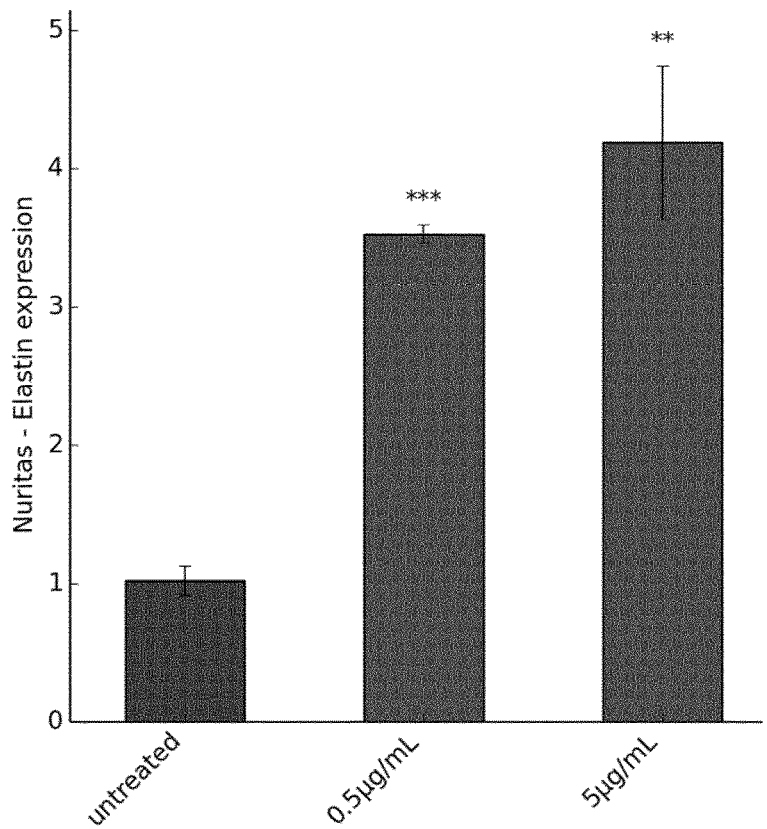
FIG. 4 illustrates the results of an elastin expression assay using untreated and peptide-treated Human Dermal Fibroblasts (HDF).

The results were calculated as a percentage of the untreated control. An increase in optical density reading indicates an increase elastin content. As illustrated by FIG. 4, samples stimulated with the peptide of the invention showed an increase in elastin production compared with untreated control.

Conclusion

These results demonstrate the efficacy of the peptide to facilitate elastin production.

Example 4

Glucose Uptake
Study Description

Glucose uptake in skeletal muscle cells was measured using 2-deoxyglucose (2-DG). 2-DG is taken up by glucose transporters and metabolized to 2-DG-6-phosphate (2-DG6P). The amount of accumulated non-metabolized 2-DG6P is proportional to glucose uptake by cells.

Methodology

Human skeletal myoblasts (Sigma 150-05a) were seeded in a 96 well plate at 10,000 cells per well in Skeletal Muscle Differentiation medium and allowed to differentiated for 72 h prior to experimentation.

The differentiated cells were serum starved for 24 h prior to stimulation with insulin or synthetic peptides. After starvation, the serum free media was removed, cells rinsed with Phosphate Buffered Saline (PBS) and media replaced with 100 µl of Krebs-Ringer-Phosphate-HEPES (KRPH) and incubated for 1 h.

The cells were then stimulated with 100 nM insulin for 30 minutes or 5 µg/ml, 0.5 µg/ml or 0.05 µg/ml synthetic peptide for 3 h respectively.

Following stimulation, the cells were incubated with 10 µl/well of 2-DG solution for 40 min and glucose uptake was measured using the 'PrismColor Glucose Uptake Assay Kit' (Molecutools), all steps were carried out according to the manufacturer's instructions. The experiment was repeated using HACAT cells.

Results

Figure 5:
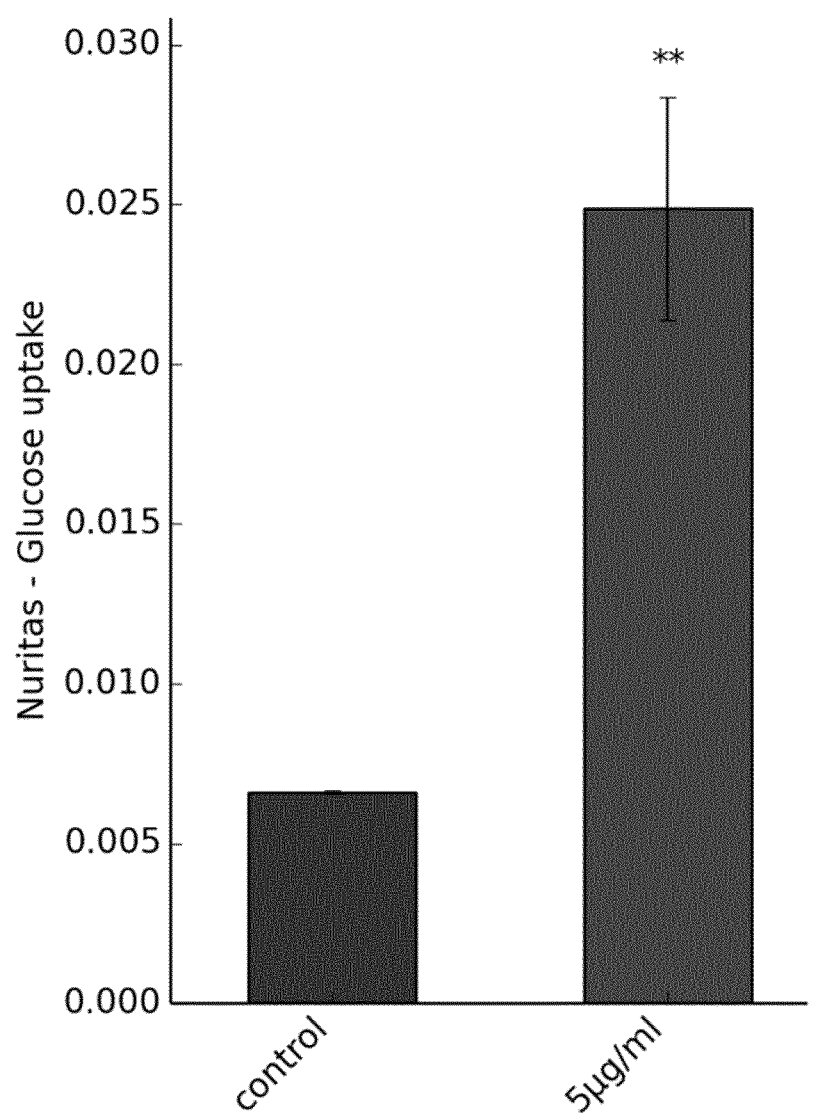
FIG. 5 illustrates the results of a glucose uptake assay using untreated and peptide-treated Human skeletal myoblasts.
Figure 6:
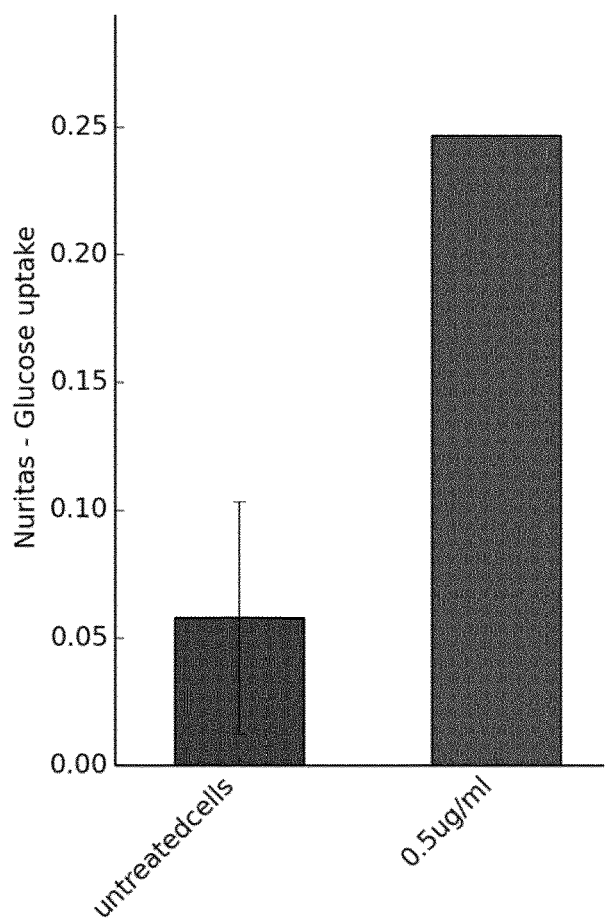
FIG. 6 illustrates the results of a glucose uptake assay using untreated and peptide-treated Human skeletal myoblasts.
Figure 7:
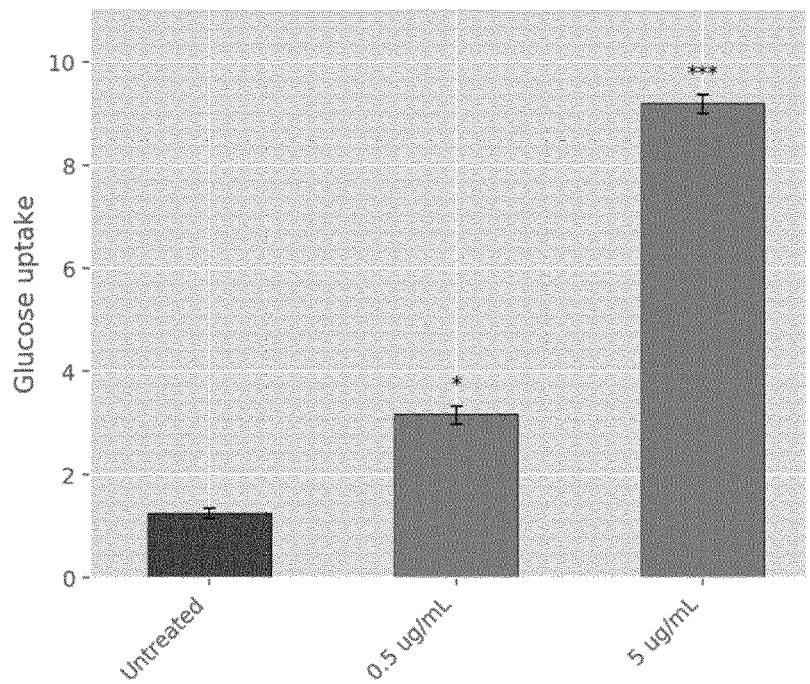
FIG. 7 illustrates the results of a glucose uptake assay using untreated and peptide-treated Human skeletal myoblasts.

The results were calculated as a percentage of the untreated control. An increase in optical density reading indicates greater incorporation of 2-DG6P and increase in glucose uptake. All experiments were carried out in duplicate on three plates (6 wells/condition). Significance was determined using the Students t-test (*$p<0.05$ compared to control, $p<0.01$ compared to control, * $p<0.001$ compared to control). FIG. 6 illustrates the results for 0.5 µg/ml synthetic peptide and FIG. 7 illustrates results for 5 µg/ml synthetic peptide. FIG. 5 displays the results for HACAT cells. As illustrated by these Figures, samples stimulated with the peptide of the invention showed an increase in glucose uptake compared with untreated control.

Conclusion

These results demonstrate the efficacy of the peptide to facilitate glucose uptake in skeletal muscle.

Example 5

GLUT-4 Translocation
Methodology

HSKMC cells sere cultured in 6-well plates and then treated with peptides/hydrolysates for 2 hrs, at concentrations of 0.5 ug/ml and 5 ug/ml. Upon completion of treatment, cell membrane proteins were collected. Briefly, cells were harvested from the wells with a cell scraper and centrifuged at 300×g for 5 min. The cell pellet was washed with 300 ul of cell wash solution and then re centrifuged at 300×g for 5 min. The supernatant was discarded and the cells resuspended in 1.5 ml of cell wash solution and transferred to a 2 ml centrifuge tube. The cells were then centrifuged at 300×g for 5 min and the supernatant discarded. 150 ul of permeabilization buffer was added to the cell pellet and vortexed briefly to obtain a homogenous cell suspension. The suspension was then incubated at 4° C. for 10 min with constant mixing. Permeabilized cells were then centrifuged at 16000×g for 15 min and the supernatant containing the cytosolic proteins was transferred to a new tube. 100 ul of solubilisation buffer was added to the pellet and resuspended by gentle pipetting. The samples were then incubated at 4° C. for 10 min with constant mixing. The samples were then centrifuged at 16000×g for 15 min at 4° C. for 10 min. The supernatant containing solubilized membrane and membrane associated proteins fractions was transferred to a new tube and stored at −80° C. until ready for assessment.

GLUT-4 was assessed in the cell membrane fractions using a sandwich ELISA from LSBio. 10 ug of protein from each sample was loaded into an individual well on a 96-well plate to a final volume of 100 ul. GLUT-4 standards (0.3 ng/ml-20 ng/ml) were also added to the plates at an identical volume. Plates were then sealed and incubated at 37° C. for 1 hour. The liquid was aspirated from each well and then 100 ul of detection reagent A was added to each well, at which point the plates were sealed, gently agitated to ensure mixing and then incubated for 1 hour at 37° C. The liquid was aspirated from each well and wells were washed 3 times using 350 ul of wash buffer. 100 ul of detection reagent B was added to each well, at which point the plates were sealed and incubated at 37° C. for 30 min. The wells were washed 5 times, as outlined previously, and 90 ul of TMB substrate was added to each well. The plates were sealed, protected from light, and incubated at 37° C. for 10 minutes to ensure optimal colour development. 50 ul of stop solution was added to each well and the optical density of the sample was determined using a microplate reader set to 450 nm. GLUT-4 concentration in the samples was calculated off the standard curve after generating a four-parameter logistic (4-PL) curve fit. Sample concentration read of the curve was then adjusted by multiplying the results by the dilution factor.

Results

Figure 8:
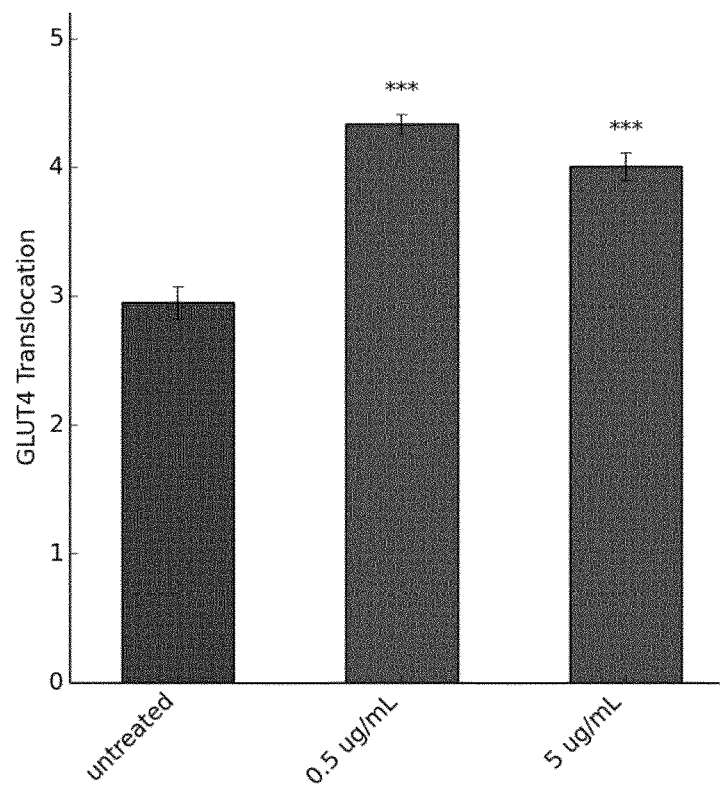
FIG. 8 illustrates the results of a GLUT4 translocation assay assay using untreated and peptide-treated Human skeletal myoblasts.

As illustrated by FIG. 8, there was an increase in GLUT4 translocation in samples stimulated with both 0.05 ug/ml and 5 ug/ml peptide.

Conclusion

The peptide displayed a trend for stimulatory effect on skeletal muscle GLUT4 translocation and its ability to facilitate glucose transport in skeletal muscle.

Example 6

Muscle Protein Synthesis (Phospho-mTOR Assay)
Study Description

The mammalian target of rapamycin (mTOR) is a Ser/Thr protein kinase that functions as an ATP and amino acid sensor to balance nutrient availability and cell growth. The activity of mTOR is regulated by insulin, amino acids, exercise, oxidative stress and growth factors which throughout its phosphorylation promote protein synthesis pathways. However, dysregulated mTOR cause accelerated ageing among many other pathologies. In muscle, when mTOR is activated (phosphorylated) leads skeletal muscle hypertrophy. This fact has been widely reported, in both rodents and humans, in the literature. Amino acids such as leucine enhances the phosphorylation of mTOR, and its activation up-regulates protein translation through the phosphorylation of the eukaryotic initiation factor 4E binding protein 1 (4E-BP1) and the ribosomal protein S6 kinase (S6K), leading to cell growth and proliferation.

Phospho-mTOR sandwich ELISA detects endogenous levels of phosphorylated mTOR at Ser2448.

Methodology

Day 1: Seed HSkMC cells in 500 uL/well of HSkMC Growth Medium and let them adhere to the wells for 16-24 h.

Day 2: Remove growth medium and add 500 uL/well of HSkMC Differentiation Medium to let them differentiate for 5-7 days.

Day 7: Treat cells for 2 hours. Collect cell lysates in lysis buffer.

Day 8: Perform BCA (protein determination) and run the assay. In a first incubation step, a mTOR antibody coated onto the ELISA microwells is used to capture mTOR (phospho and non-phospho) from the cell lysates. Then, following extensive washing, a specific phospho-mTOR detection antibody is added to detect only the phospho-mTOR protein captured before. Finally, a HRP-linked antibody is used to recognise the detection antibody and through the addition of TMB (HRP substrate) develop color proportionally to the quantity of mTOR phosphorylated at Ser2448.

Results

Figure 9:
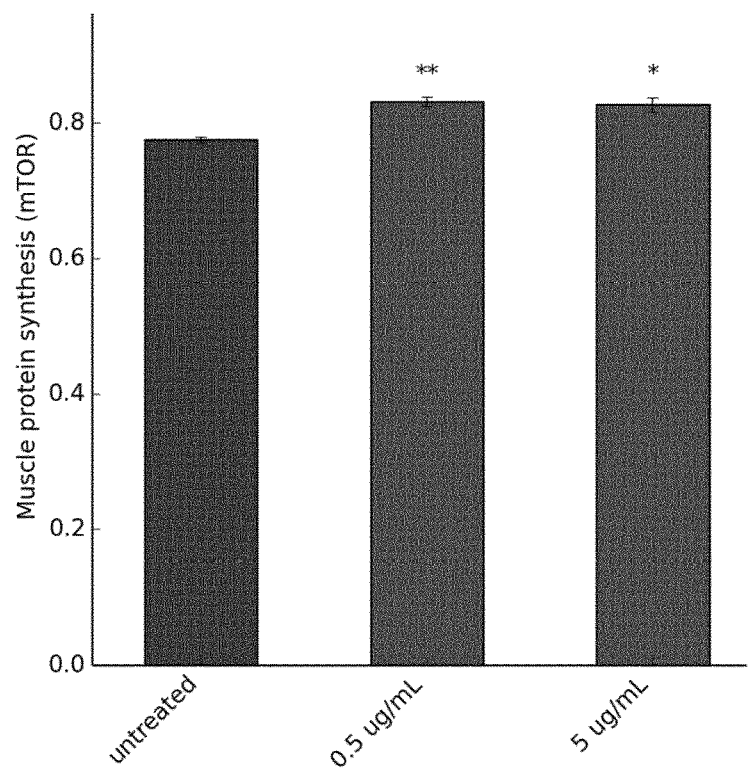
FIG. 9 illustrates the results of a muscle protein synthesis (mTOR) assay.

The results are illustrated by FIG. 9. Samples stimulated with 0.5 µg/ml and 5 µg/ml displayed in increase in mTOR.

Conclusion

These results demonstrate the efficacy of the peptide to facilitate muscle protein synthesis and muscle growth.

Example 7 to 15: Formulations

In an embodiment, the composition is formulated as a topical composition. In one embodiment, it may be an emulsion or cream or a rub, such as a muscle rub.

In an embodiment, the cream comprises an excipient or diluent, a suspending agent, a preservative and an amount of at least one peptide of the invention.

In an embodiment, the cream comprises an alcohol, a carbomer, a sorbate, water and at least one peptide of the invention.

Preferably the alcohol is butylene glycol (1,3-butanediol). The alcohol may be present in an amount of between 1 and 10% of the composition, preferably between 2 and 6%, preferably 4%. The sorbate may be polysorbate-20. The sorbate may be present in an amount of between 0.01 to 1% of the composition, preferably between 0.05 and 0.5%, preferably 0.10%. Water is present in an amount of between 10% and 90%, preferably 30% to 75%. The carbomer may be present in an amount of from 0.05% to 1%, preferably, 0.1% to 0.5%, preferably, 0.15%. The carbomer may be Ultrez 10.

The peptide of the invention may be present in an amount of from 0.5% to 10%, preferably, 1% to 5%, preferably 3%.

The composition may further comprise one or more of sugar alcohol such as glycerine, parabens, silicon, such as cyclohexasiloxane, a fatty alcohol or phosphoric acid or a mixture of fatty alcohol and phosphoric acid, such as cetearyl alcohol, dicetyl phosphate and Cereth phosphate or combinations thereof, a polyoxyethylene stearyl ethers, such as Steareth 2 and 10, and a fragrance.

An exemplary rub or emulsion is follows in Example 7.

| Ingredient | Exemplary (w/w) % |
|---|---|
| Phase A | |
| Water | 70.95 |
| Carbomer | 0.15 |
| Phase B | |
| Glycerin | 3.5 |
| Phase C | |
| Steareth 2 | 0.40 |
| Cetearyl alcohol dicetyl phosphate and Ceteth 10 phosphate | 4 |
| Cyclohexsiloxane | 2 |
| Dioctyl succinate | 7 |
| Steareth 10 | 1.2 |
| Mixed parabens | 0.30 |
| Phase D | |
| Sorbate | 0.10 |
| Phase E | |
| Water | 2.50 |
| Sodium hydroxide | 0.30 |
| Phase F | |
| Fragrance | 0.10 |
| Phase G | |
| Peptide(s) of the invention | 3 |

The resulting emulsion is suited as a rub. In addition, the rub is suitable for fragile aged skin. The emulsion is suitable for improving fine lines, wrinkles, dryness reducing redness and irritation.

Percentages are examples only and it will be appreciated that any suitable percentage may be used depending on the use.

The emulsion is prepared in the following way: Phase A: disperse Ultrez 10 (carbomer) in water and let is swell for 20 minutes, then add phase B; heat to 75° C. Heat Phase C separately to 75° C. Mix the two phases under stirring, homogenise, add Phase D, neutralise with Phase E, cool until reaching 30° C., then add Phase F and Phase G; adjust to pH to 6 with ~NaOH. It will be understood that this is an example only and any suitable method known in the art may be used.

In a further embodiment, the composition may comprise one or more of water, a carbomer, a sorbate such as potassium sorbate, a sugar alcohol, such as glycerine, an alcohol such as 2-(2-Ethoxyethoxy)ethanol, a polyoxyethylene stearyl ethers, such as Steareth 2, a fatty alcohol or phosphoric acid or a mixture of fatty alcohol and phosphoric acid, such as cetearyl alcohol, dicetyl phosphate and Cereth 10 phosphate or combinations thereof, a siloxane, such as cyclomethicone, a Caprylic Capric Triglycerides, a sorbitan Stearate, Parabens, Sodium hydroxide, an active agent such as a skin lightening agent, such as a mixture of lycerin (and) Butylene Glycol (and) Arcostaphylus Uva Ursi Leaf Extract (and) Mitracarpus Scaber Extract (ETIOLINE®), or a muscle health agent and peptide of the invention.

The following composition in Example 8 is an example of an emulsion or cream or a rub.

| Ingredient | Exemplary (w/w) % |
| --- | --- |
| Water Deionised | qs 100 |
| Carbomer | 0.10 |
| Potassium Sorbate | 0.10 |
| Transcutol | 3.00 |
| Glycerin | 8.00 |
| Volpo S2 [Steareth 2] | 0.60 |
| Crodafos CES [Cetearyl Alcohol (and) Dicetyl Phosphate (and) Ceteth 10 Phosphate] | 4.00 |
| DC 344 [Cyclomethicone] | 2.00 |
| Crodamol GTCC [Caprylic/Capric triglyceride] | 10.00 |
| Crill 3 [Sorbitan Stearate] | 1.60 |
| Mixed Parabens | 0.30 |
| Sodium Hydroxide 30% | 0.35 |
| Water Deionised | 3.50 |
| Peptide | 3.00 |
| Active | 3.00 |

The active can be ETIOLINE® [Glycerine (and) Etylene Glycol (and) Arcostaphylus uva leaf extract and Mitracarpus Scaber extract] ETIOLINE® is a skin lightening ingredient sold by SEDERMA (WO 98/05299 of Nov. 19, 1996).

It will be understood that ETIOLINE can be replaced with any active agent, such as an agent that aids muscle health, development or recovery.

This formulation can be made according to the procedures generally outlined in Example 7. The composition may be an emulsion or cream or rub comprising one or more of water, a carbomer, such as Ultrez 10, a sugar alcohol, such as glycerine, an alcohol such as phenova (phenoxyethanol and mixed parabens), a fatty acid ester such as ethylhexyl palmitate, a fatty alcohol such as cetearyl alcohol, a lactic acid ester such as myristyl lactate, a sorbate such as polysorbate 20 and/or potassium sorbate, a polymeric emulsifier such as Acrylate (C10-30 alkyl acrylate) and a cross polymer, a siloxane, such as cyclomethicone, sodium hydroxide, at least one active agent, such as a muscle health agent or an agent for the treatment of stretch marks, such as siegesbeckia Orientalis extract (Darutoside) and a peptide.

The following composition in Example 9 is an example of an emulsion or cream. In an embodiment, the emulsion or cream is an anti-stretch mark cream.

| Ingredient | Exemplary (w/w) % |
| --- | --- |
| Part A | |
| Water Deionised | qs 100 |
| Ultrez 10 [Carbomer] | 0.40 |
| Part B | |
| Glycerin | 5.00 |
| Phenova [Phenoxyethanol (and) Mixed Parabens] | 0.80 |

| Ingredient | Exemplary (w/w) % |
| --- | --- |
| Part C | |
| Crodamol OP [Ethylhexyl Palmitate] | 4.00 |
| Crodacol CS90 [Cetearyl alcohol] | 0.50 |
| Crodamol ML [Myristyl Lactate] | 0.30 |
| Crillet 1 [Polysorbate 20] | 1.00 |
| Part D | |
| Pemulen TR2 [Acrylates/C 10-30 Alkyl Acrylate (and) Crosspolymer] | 0.20 |
| DC 345 [Cyclomethicone] | 2.00 |
| Part E | |
| Potassium Sorbate | 0.10 |
| Part F | |
| Water | 6.00 |
| Sodium Hydroxide 38% | 0.60 |
| Part G | |
| peptide | 3.00 |
| Active | 2.00 |

The active can be Darutoside (Siegesbeckia Orientalis Extract). Darutoside is a molecule sold by SEDERMA for the treatment of stretch marks. It will be understood Darutoside can be replaced with any active agent, such as any agent that aids muscle health, development or recovery.

This emulsion or rub is prepared in the following way: Phase A disperse Ultrez 10 (carbomer) in water and let it swell for 20 minutes, then add phase B; heat to 75° C. Heat Phase C separately to 75° C. Mix the two phases under stirring, homogenise, add Phase D, neutralise with Phase E, cool until reaching 30° C., then add Phase F and Phase G, adjust pH to ~6 with NaOH.

In an embodiment of the invention the composition may be an emulsion, cream or a gel, preferably a gel, comprising one or more of water, a carbomer, such as Ultrez 10, a sugar alcohol, such as glycerine, an alcohol such as phenova (phenoxyethanol and mixed parabens), a sorbate such as polysorbate 20 and/or potassium sorbate, a polymeric emulsifier such as Acrylate (C10-30 alkyl acrylate), a siloxane, such as cyclomethicone, sodium hydroxide, a peptide and at least one agent such as an agent for muscle health, recovery or development, or a suitable moisturising agent, such as an agent comprising *Imperata Cylindrica* (root) extract, water, glycerine, PEG-8, and carbomer (MOIST 24). In an embodiment, the gel is a moisturising gel.

The following composition in Example 10 is an example of a gel. In an embodiment, the gel is a moisturising gel

| Ingredient | Exemplary (w/w) % |
| --- | --- |
| Part A | |
| Ultrez 10 [Carbomer] | 0.20 |
| Water Deionised | qs 100 |
| Part B | |
| Glycerin | 3.00 |
| Phenova [Phenoxyethanol (and) Mixed Parabens] | 0.80 |
| Part C | |
| Crillet 1 [Polysorbate 20] | 0.50 |
| Part D | |
| Potassium Sorbate | 0.10 |

-continued

| Ingredient | Exemplary (w/w) % |
|---|---|
| Part E | |
| Pemulen TR1 [Acrylates/C10-30 Alkyl Acrylate Crosspolymer] | 0.20 |
| DC 345 [Cyclomethicone] | 3.00 |
| | 2.00 |
| Part F | |
| Water | 4.00 |
| Sodium Hydroxide 38% | 0.40 |
| Part G | |
| Peptide | 3.00 |
| Active | 5.00 |
| MOIST-24 is a moisturising plant extract sold by SEDERMA (WO 01/62218 of Aug. 30, 2001). | |

This formulation can be made according to the procedures generally outlined in Example 11.

The active can be MOIST-24 (R) [Imperata Cylindrica (root) Extract (and) water (and) Glycerin (and) PEG-8 (and) Carbomer]. It will be understood that any agent can be used to replace MOIST-24. For example, any agent that aids muscle health, development or recovery.

In an embodiment of the invention the composition may be an emulsion, cream or rub comprising one or more of water, a carbomer, such as Ultrez 10, a sorbate such as polysorbate 20, polysorbate 60 and/or potassium sorbate, an alcohol such as phenova (phenoxyethanol and mixed parabens), butylene glycol (1,3-butanediol), lanolin alcohol, and/or cetearyl alcohol, sorbitan stearate, Polydimethylsiloxane such as dimethicone, an isotridetyl isononanoate, a caprylic/capric triglyceride, a cetyl ester, sodium hydroxide, water, an agent for muscle health, recovery and/or development, or an anti-aging agent, such as an agent comprising butylene glycol, water, laureth-3, hydroxyethylcellulose and acetyl-dipeptide-1-cetylester (CALMOSENSINE®).

The following composition in Example 11 is an example of a cream or a rub.

| Ingredient | Exemplary (w/w) % |
|---|---|
| Part A | |
| Water Deionised | qs 100 |
| Ultrez 10 [Carbomer] | 0.20 |
| Part B | |
| Potassium Sorbate | 0.10 |
| Part C | |
| Butylene Glycol | 2.00 |
| Phenova [Phenoxyethanol (and) Mixed Parabens] | 0.80 |
| Part D | |
| Crill 3 [Sorbitan Stearate] | 1.00 |
| Crillet 3 [Polysorbate 60] | 2.50 |
| DC 200 [Dimethicone | 2.50 |
| Crodamol TN [Isotridetyl Isononanoate] | 5.00 |
| Crodamol GTCC [Caprylic/Capric Triglyceride] | 5.00 |
| Crodamol SS [Cetyl Esters] | 1.00 |
| Super Hartolan [Lanolin Alcohol] | 0.50 |
| Super Sterol Ester [C10-C30 Cholesterol/Lanosterol esters] | 0.30 |
| Crodacol CS90 [Cetearyl Alcohol] | 3.00 |
| Part E | |
| Water Deionised | 2.50 |
| Sodium Hydroxide 38% | 0.25 |

-continued

| Ingredient | Exemplary (w/w) % |
|---|---|
| Part F | |
| peptide | 3.00 |
| Active agent | 4.00 |

This formulation can be made according to the procedures generally outlined in Example 9. The active can be CALMOSENSINE® [Butylene Glycol (and) water (and) Laureth-3 (and) Hydroxyethylcellulose (and) Acetyl-Dipeptide-1-cetylester] Calmosensine® is an analgesic peptide offered by SEDERMA (WO 98/07744 of Feb. 26, 1998). It will be understood that any agent can be used to replace CALMOSENSINE. For example, any agent that aids muscle health, development or recovery.

In an embodiment of the invention the composition may be an emulsion, cream or rub comprising one or more of water, a carbomer, such as Ultrez 10, a sugar alcohol, such as glycerine, a sorbate such as potassium sorbate, a steareth such as Steareth 10, a fatty alcohol or phosphoric acid or a mixture of fatty alcohol and phosphoric acid, such as cetearyl alcohol, dicetyl phosphate and Cereth 10 phosphate or combinations thereof, diethylhexyl succinate, mixed parabens, Sorbitan Stearate, Sodium Hydroxide, water, a peptide, and an active agent, such as an agent for muscle health, recovery and/or development or an agent for mature skin, such as one comprising Trifolium Pratense (Clover) Flower Extract (and) Glycerin (and) Butylene Glycol (and) Lecithin (TEROCARE®).

The following composition in Example 12 is an example of a cream or a rub.

| Ingredient | Exemplary (w/w) % |
|---|---|
| Part A | |
| Ultrez 10 [Carbomer] | 0.20 |
| Water | qs 100 |
| Part B | |
| Glycerin | 3.50 |
| Part C | |
| Potassium Sorbate | 0.10 |
| Part D | |
| Volpo S10 [Steareth 10] | 1.50 |
| Crodafos CES [Ceterayl Alcohol] | 3.50 |
| Dicetyl Phosphate(and) Ceteth-10 Phosphate] DC 200 [Dimethicone] | 2.00 |
| Diethylhexyl Succinate | 7.00 |
| Mixed Parabens | 0.30 |
| Crill 3 [Sorbitan Stearate] | 0.40 |
| Part E | |
| Sodium Hydroxide 38% | 0.20 |
| Water | 4.00 |
| Part F | |
| Active agent | 3.00 |
| Peptide | 3.00 |

This formulation can be made according to the procedures generally outlined in Example 9. The active agent can be STEROCARE™ [Trifolium Pratense (Clover) Flower Extract (and) Glycerin (and) Butylene Glycol (and) Lecithin Sterocare® is offered by SEDERMA as an active ingredient for mature skin (FR 2769502 of Apr. 14, 2000, WO 99/18927 of Apr. 22, 1999). It will be understood that any agent can be used to replace STEROCARE®. For example, any agent that aids muscle health, development or recovery.

The following composition in Example 13 is an example of a rub or a tonic.

| Ingredient | Exemplary (w/w) % |
|---|---|
| Part A | |
| Water deionised | qs 100 |
| Part B | |
| Mixed Parabens | 0.14 |
| Butylene Glycol | 2.00 |
| Part C | |
| Peptide | 0.0008 |
| Ethanol | 10.00 |
| Part D | |
| Crillet 1 (Polysorbate 20) | 1.50 |
| Fragrance | 0.10 |

The following composition in Example 14 is an example of a cream or a rub.

| Ingredient | Exemplary (w/w) % |
|---|---|
| Part A | |
| Ultrez 10 [Carbomer] | 0.20 |
| Water Deionised | qs 100 |
| Part B | |
| Glycerin | 3.00 |
| Part C | |
| Potassium Sorbate | 0.10 |
| Part D | |
| Volpo S10 [Steareth 10] | 1.50 |
| Crodafos CES [Ceteralyl Alcohol Dicetyl Phosphate (and) Ceteth-10 Phosphate] | 3.00 |
| DC 200 [Dimethicone] | 2.00 |
| Crodamol OSU [Diethylhexyl Succinate] | 5.00 |
| Mixed Parabens | 0.30 |
| Crill 3 [Sorbitan Stearate] | 0.40 |
| Part E | |
| Sodium Hydroxide 38% | 0.20 |
| Water Deionised | 4.00 |
| Part F | |
| Water | 10.0 |
| Peptide | 0.00075 |
| Agent | 0.001 |
| Agent | 0.002 |

The agent can be Deferoxamine and/or Berberine. These are used as skin thickeners. Deferoxamine and Berberine can be replaced with another active agent, such as an agent for muscle health, recovery and development.

The following composition in Example 15 is an example of a gel or rub.

| Ingredient | Exemplary (w/w) % |
|---|---|
| Part A | |
| Water Deionised | qs 100 |
| Part B | |
| Butylene Glycol | 5.00 |
| Phenova [Phenoxyethanol (and) Mixed Parabens] | 0.80 |
| Part C | |
| Crill 3 [Sorbitan Stearate] | 1.20 |
| Crillet 3 [Polysorbate 60] | 3.00 |
| DC 200 [Dimethicone] | 2.00 |
| Crodamol IPM [Isopropyl Myristate] | 5.00 |
| Crodamol W [Stearyl Heptanoate] | 0.30 |
| Crodamol GTCC [Caprylic/Capric Triglyceride] | 5.00 |
| Crodacol CS90 [Cetearyl Alcohol] | 2.00 |
| Part D | |
| Carbopol 980 at 2% [Carbomer] | 10.00 |
| Part E | |
| Potassium Sorbate | 0.10 |
| Part F | |
| Water | 2.00 |
| Sodium Hydroxide | 0.20 |
| Part G | |
| Water | 10.0 |
| Peptide | 0.00045 |
| Active agent | 0.1 |
| Active agent | 0.0001 |

This gel can be prepared in the following way: Homogenize Part B and pour it into Part A. Heat Part (A+B) to 75° C. Heat Part C and Part D to 75° C. Pour Part C into Part (A+B) with helix stirring; then, pour Part D into Part (A+B+C). Add Part F and Part E. Pour Part G at about 35° C.

The active can be Rutin and or Bowman Birk Inhibitor. These agents are used for tissue regeneration. Rutin and Bowman Birk Inhibitor can be replaced with another active agent, such as an agent for muscle health, recovery and development.

Example 16

Puromycin ELISA

Study Description

Puromycin is an aminonucleoside antibiotic produced by the bacterium *Streptomyces alboniger*. It is a structural analogue of aminoacyl-transfer RNA and, as such, can be incorporated into elongating peptide chains via the formation of a peptide bond. However, whereas aminoacyl-tRNAs contain a hydrolyzable ester bond, puromycin hasn't it in the equivalent position. Thus, the binding of puromycin to a growing peptide chain prevents a new peptide bond from being formed with the next aminoacyl-tRNA. As a consequence, puromycin binding results in the termination of peptide elongation, and leads to the release of the truncated puromycin bound peptide from the ribosome. At very high concentrations, puromycin effectively shuts down the elongation phase of translation and thus inhibit protein synthesis; however, at very low concentrations, that do not inhibit the overall rate of translation, the rate at which puromycin-labelled peptides are formed reflects the overall rate of protein synthesis. This later property makes puromycin a potential tool for the measurement of changes in protein synthesis rates.

Methodology

1. Dispense 100 nl Coating Buffer per well in the required number of wells in a 96 well ELISA plate. Dilute and mix the Protein extract (in the same buffer the sample is in) to 5 ug/nl. Immediately dispense 1 µl/well into plate.

2. Incubate the plate at 4° C. for 16-24 h.
3. Vigorously shake out contents. Wash 1× with 200 ul PBS.
4. Add 200 μl Blocking Solution (5% BSA in PBS). Incubate over the day 4-6 h at RT.
5. Dilute Puromycin antibody in Blocking solution and incubate overnight at 4° C.
8. Wash 2× with 200 ul PBS
9. Add 100 μl Secondary Antibody diluted 1:1000 in Blocking Soln. Incubate 1 h at RT.
10. Wash 4×200 μl PBS. Shake out contents vigorously.
11. Add 100 μl TMB Substrate and incubate for 15-20 min
12. Add Stop solution and read the plate at 450 nm.

Results

Figure 10:
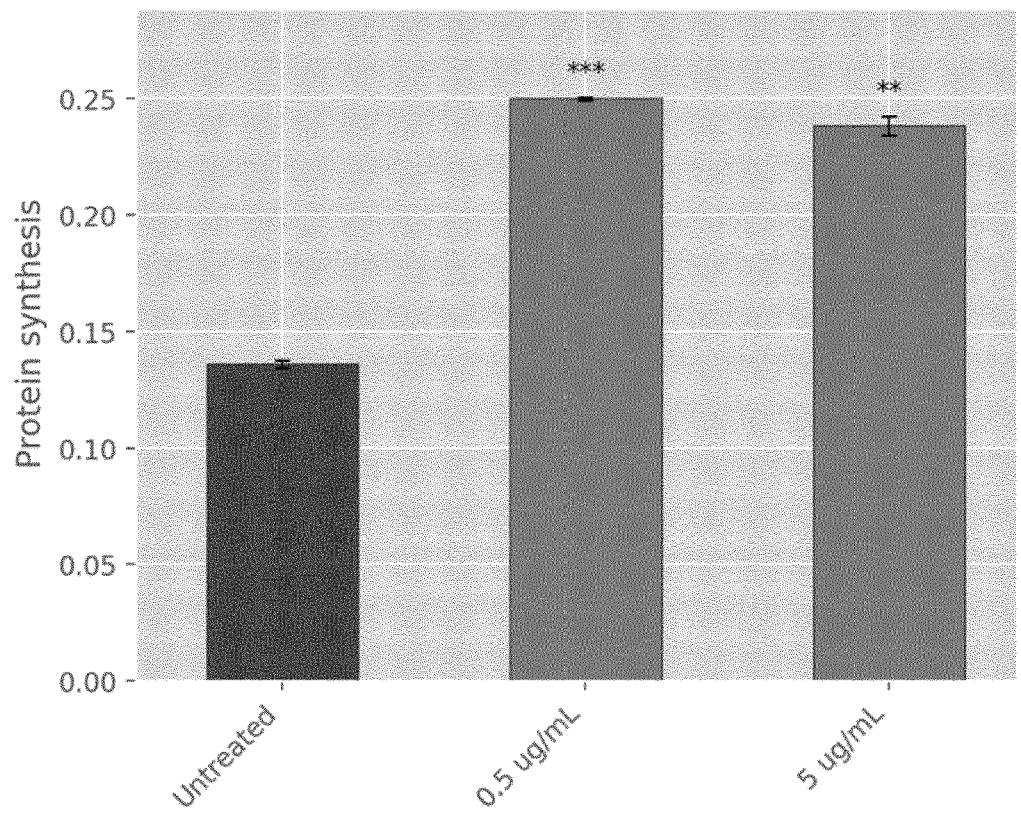
FIG. 10 illustrates the results of a muscle protein synthesis (puromycin) assay.

FIG. 10 illustrates an increase in protein synthesis.

Example 17

Toxicity
Methodology

100 μl of HSkMC cells were seeded in a 96 well plate, pre-coated with collagen, at a concentration of 1×10^4 cells/well. Cells were allowed to adhere overnight at 37° C. 5% CO2 and the following day the growth media was replaced with 100 μl of cell differentiation media and returned to the incubator at 37° C. 5% CO2. The cell differentiation media was changed every 2 days for a period of 6 days, until the HSkMC cells were fully differentiated into myotubes. On day 7, the cell differentiation media was replaced with 100 μl of basal media and starved overnight at 37° C. 5% CO2.

Figure 11:
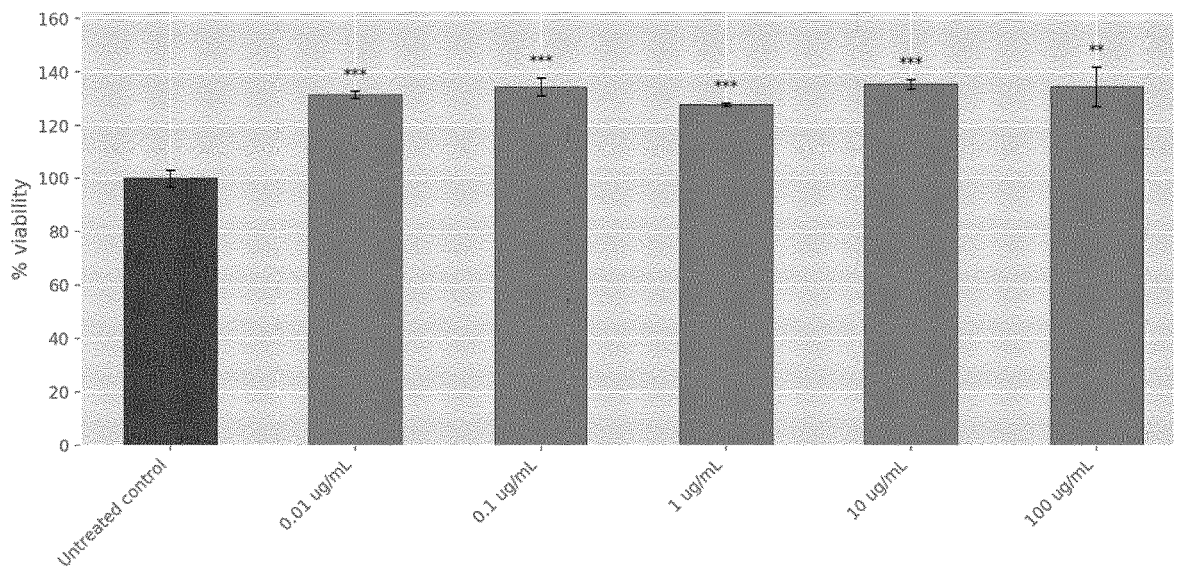
FIG. 11 illustrates the results of cell toxicity study in HSKMC cells using a peptide of SEQ ID NO. 1.

On the day of the MTT assay, the starvation media was removed and replaced with 100 μl of basal media containing the peptide of SEQ ID NO. 1. The cells were incubated in this treatment for a period of 20 min at 37° C. 5% CO2, at which point the treatment media was removed and replaced with 110 μl of MTT solution, and incubated for 2 h at 37° C. 5% CO2. After this incubation step the MTT solution was removed and replaced with 110 μl of DMSO. The plate was covered in tinfoil and placed in a shaker at RT for 5 min. The plate was read using a spectrophotometer (SpectraMax M3, Molecular devices, Sunnyvale, Calif. 94089 USA) set to 570 nm, and cytotoxicity of the peptide of SEQ ID NO. 1 was assessed based on the optical density of the samples. The results are illustrated by FIG. 11.

Example 18

Figure 12:
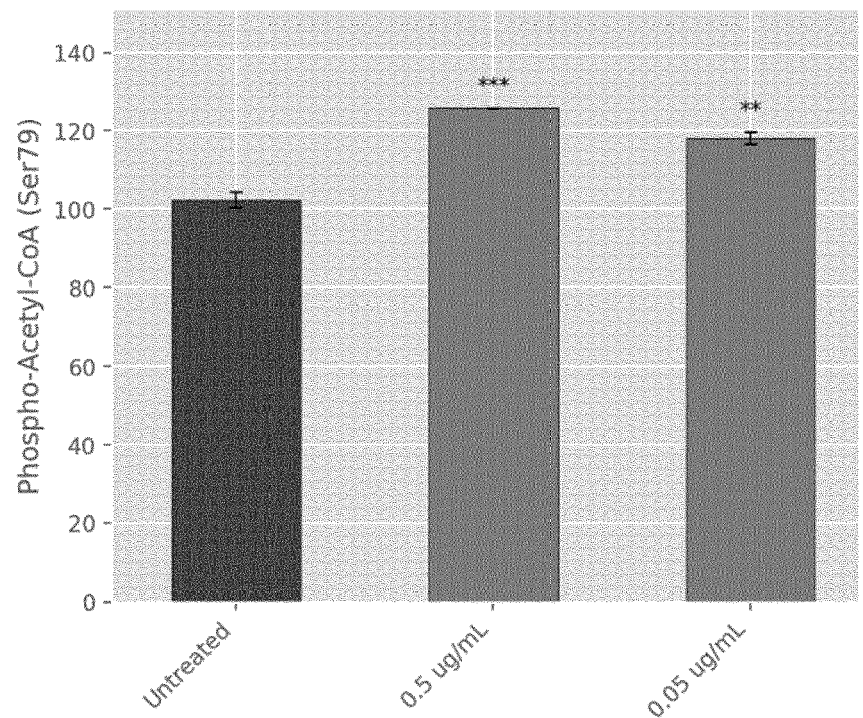
FIG. 12 illustrates the results of Phospho-Acetyl-CoA Carboxylate (Ser 79) ELISA (peptide of SEQ ID NO. 1).

This set of experiments was undertaken to understand the mechanism of action of a peptide of SEQ ID NO. 1.
Phospho-Acetyl CoA
Methodology Phospho-Acetyl-CoA Carboxylase (Ser79) Sandwich ELISA Kit is a solid phase sandwich enzyme-linked immunosorbent assay (ELISA) that detects endogenous levels of acetyl-CoA carboxylase (ACC) when phosphorylated at Ser79. A phospho-ACC (Ser79) rabbit antibody was coated onto the microwells. After incubation with cell lysates, phospho-ACC protein was captured by the coated antibody. Following extensive washing, an ACC mouse detection mAb was added to detect the captured ACC protein. Anti-mouse IgG, HRP-linked antibody was then used to recognize the bound detection antibody. HRP substrate, TMB, was added to develop color. The magnitude of the absorbance for the developed color was proportional to the quantity of ACC phosphorylated at Ser79. These results are illustrated by FIG. 12.

Acetyl-CoA carboxylase (ACC) catalyzes the carboxylation of acetyl-CoA to malonyl-CoA. It is the key enzyme in the biosynthesis and oxidation of fatty acids. In rodents, the 265 kDa ACC1 (ACCα) form is primarily expressed in lipogenic tissues, while 280 kDa ACC2 (ACCβ) is the main isoform in oxidative tissues. However, in humans, ACC2 is the predominant isoform in both lipogenic and oxidative tissues. Phosphorylation by AMPK at Ser79 or by PKA at Ser1200 inhibits the enzymatic activity of ACC. ACC is a potential target of anti-obesity drugs.

Phospho-Akt1
Methodology

Phospho-Akt1 (Ser473) Sandwich ELISA Kit is a solid phase sandwich enzyme-linked immunosorbent assay (ELISA) that detects endogenous levels of phospho-Akt1 (Ser473) protein. Phospho-Akt (Ser473) Rabbit mAb was been coated on the microwells. After incubation with cell lysates, phospho-Akt (Ser473) protein was captured by the coated antibody. Following extensive washing, Akt1 Mouse Antibody was added to detect the captured phospho-Akt1 (Ser473) protein. Anti-Mouse IgG, HRP-linked Antibody was then used to recognize the bound detection antibody. HRP substrate, TMB, was added to develop colour. The magnitude of absorbance for this developed colour is proportional to the quantity of phospho-Akt1 (Ser473) protein.

Figure 13:
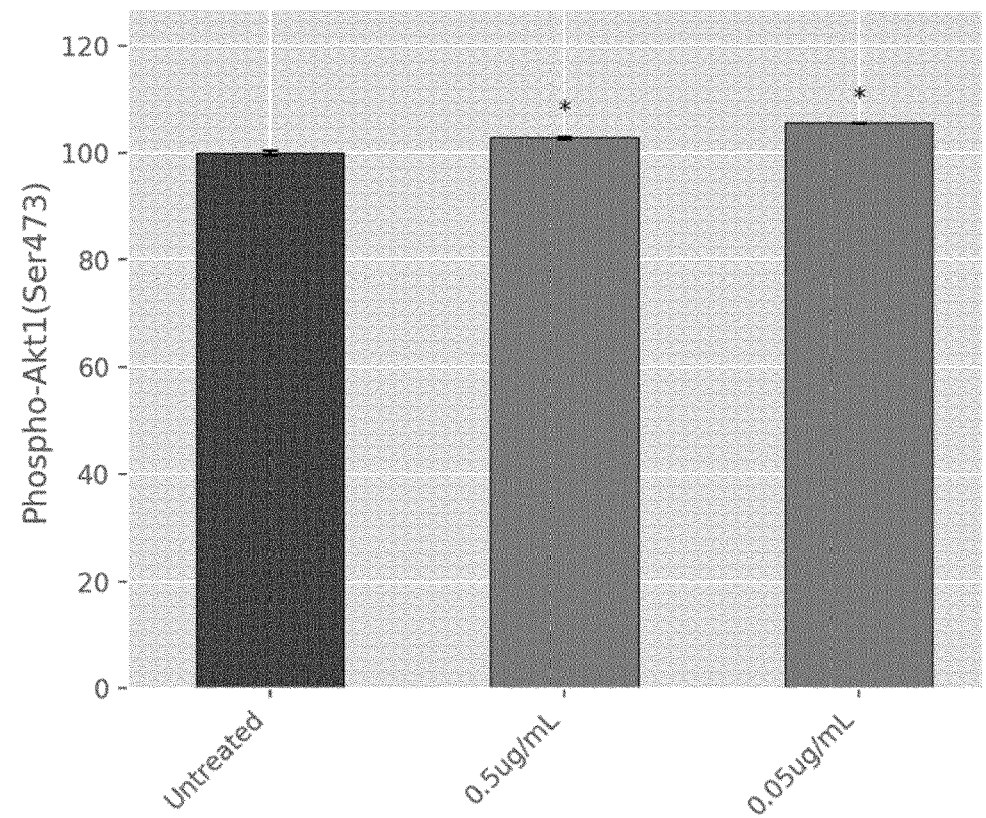
FIG. 13 illustrates the results of Phospho-Akt1 ELISA (peptide of SEQ ID NO. 1).

The results are illustrated by FIG. 13.

Akt, also referred to as PKB or Rac, plays a critical role in controlling survival and apoptosis. This protein kinase is activated by insulin and various growth and survival factors to function in a wortmannin-sensitive pathway involving PI3 kinase. Akt is activated by phospholipid binding and activation loop phosphorylation at Thr308 by PDK1 and by phosphorylation within the carboxy terminus at Ser473. The previously elusive PDK2 responsible for phosphorylation of Akt at Ser473 has been identified as mammalian target of rapamycin (mTOR) in a rapamycin-insensitive complex with rictor and Sin1. Akt promotes cell survival by inhibiting apoptosis through phosphorylation and inactivation of several targets, including Bad, forkhead transcription factors, c-Raf, and caspase-9. PTEN phosphatase is a major negative regulator of the PI3 kinase/Akt signaling pathway. LY294002 is a specific PI3 kinase inhibitor. Another essential Akt function is the regulation of glycogen synthesis through in phosphorylation and inactivation of GSK-3α and β. Akt may also play a role in insulin stimulation of glucose transport. In addition to its role in survival and glycogen synthesis, Akt is involved in cell cycle regulation by preventing GSK-3β-mediated phosphorylation and degradation of cyclin D1 and by negatively regulating the cyclin dependent kinase inhibitors p27 Kip1 and p21 Waf1/Cip1. Akt also plays a critical role in cell growth by directly phosphorylating mTOR in a rapamycin-sensitive complex containing raptor. More importantly, Akt phosphorylates and inactivates tuberin (TSC2), an inhibitor of mTOR within the mTOR-raptor complex.

Phospho-AMPK Alpha
Methodology

Figure 14:
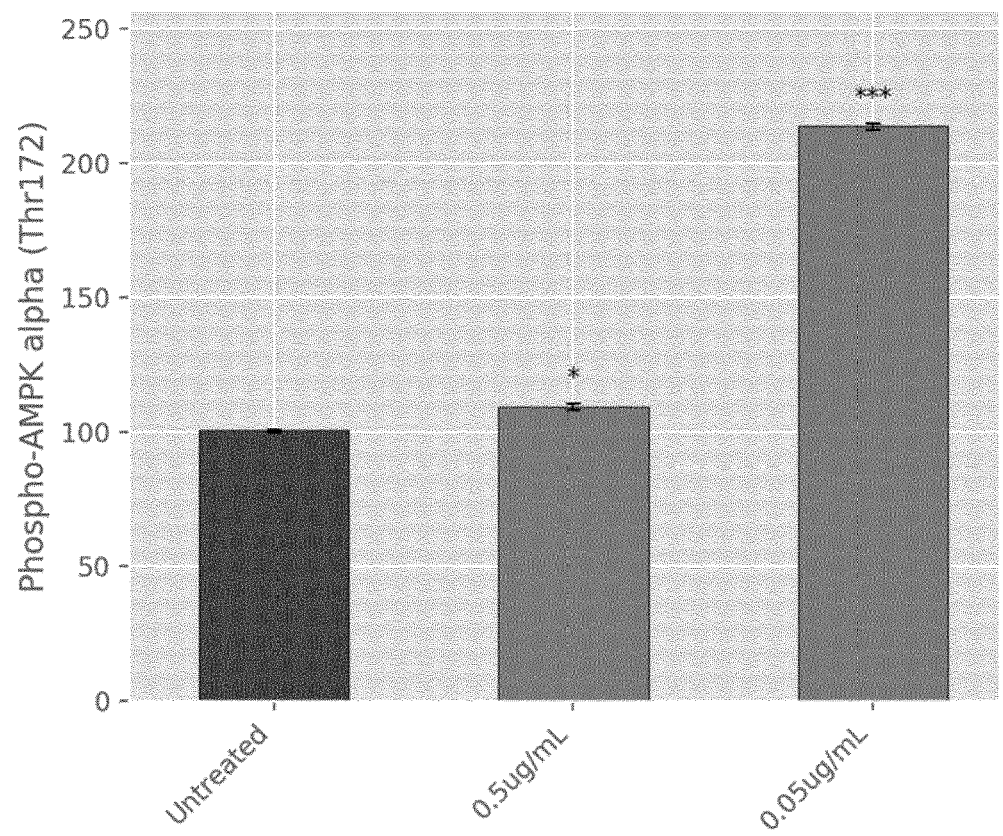
FIG. 14 illustrates the results of Phospho-AMPK alpha ELISA (peptide of SEQ ID NO. 1).
Figure 15:
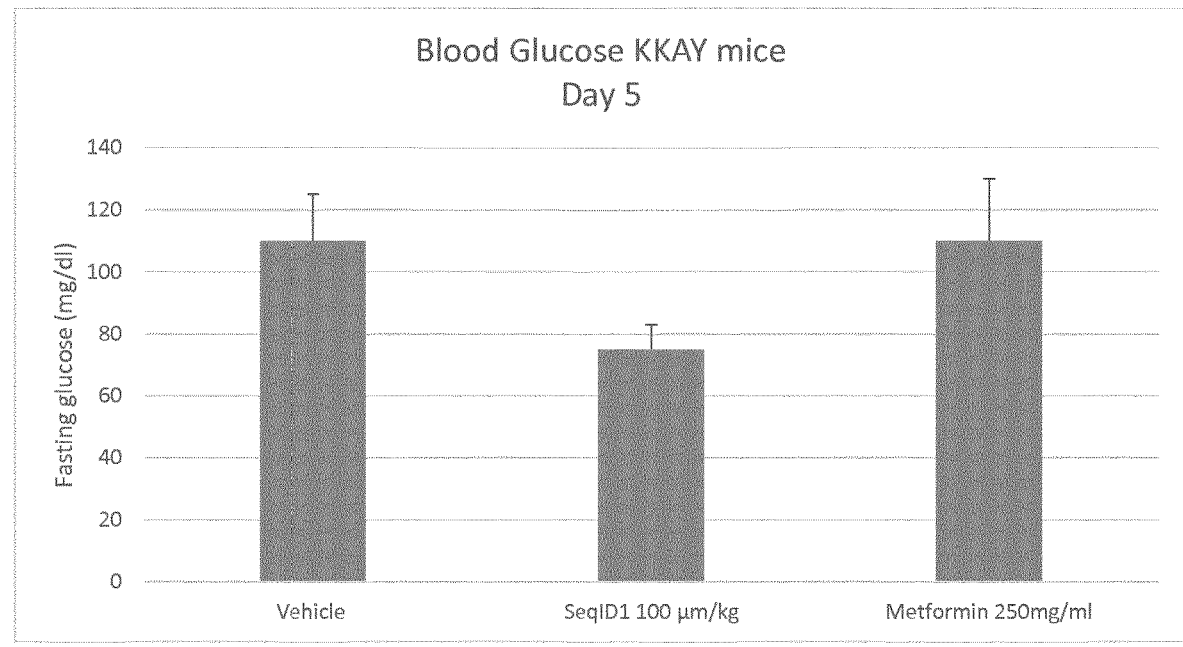
FIG. 15 illustrates blood glucose levels after 5 days of treatment with a peptide of SEQ ID NO. 1 in KKAY mice.
Figure 16:
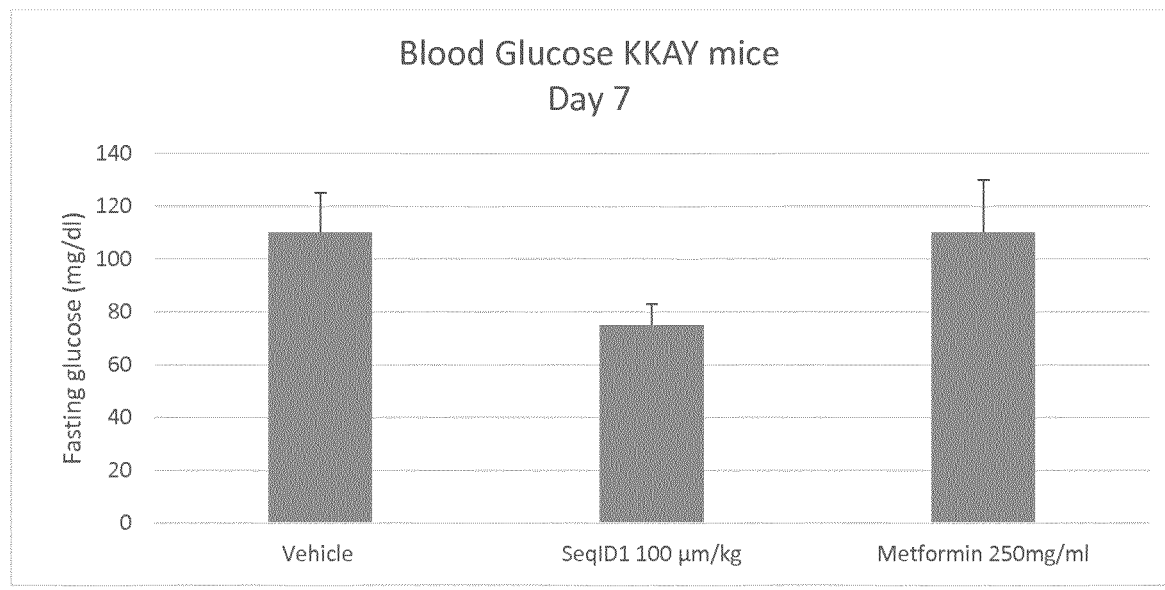
FIG. 16 illustrates blood glucose levels after 7 days of treatment with a peptide of SEQ ID NO. 1 in KKAY mice.
Figure 17:
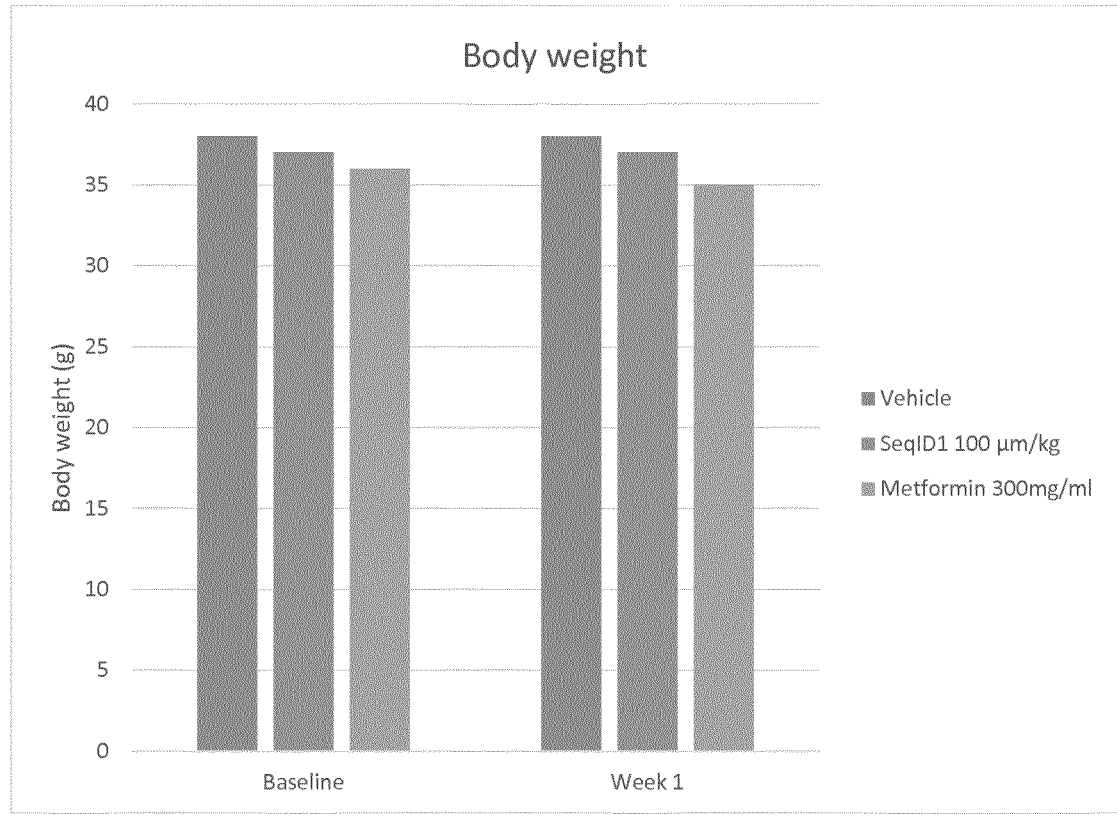
FIG. 17 illustrates body weight of KKAY mice after 13 days of treatment with a peptide of SEQ ID NO. 1.

Phospho-AMPKα (Thr172) Sandwich ELISA Kit is a solid phase sandwich enzyme-linked immunosorbent assay (ELISA) that detects endogenous levels of AMPKα when phosphorylated at Thr172. An AMPKα rabbit antibody has been coated onto the microwells. After incubation with cell lysates, AMPKα (phospho and nonphospho) was captured by the coated antibody. Following extensive washing, a phospho-AMPKα (Thr172) mouse detection antibody was added to detect phosphorylation of Thr172 on the captured AMPKα protein. Anti-mouse IgG, HRP-linked antibody was then used to recognize the bound detection antibody. HRP substrate, TMB, was added to develop colour. The magnitude of the absorbance for this developed colour was proportional to the quantity of AMPKα phosphorylated at Thr172. The results are illustrated by FIG. 14.

AMP-activated protein kinase (AMPK) is highly conserved from yeast to plants and animals and plays a key role in the regulation of energy homeostasis. AMPK is a heterotrimeric complex composed of a catalytic a subunit and regulatory β and γ subunits, each of which is encoded by two or three distinct genes (α1, 2; β1, 2; γ1, 2, 3). The kinase is activated by an elevated AMP/ATP ratio due to cellular and environmental stress, such as heat shock, hypoxia, and ischemia. The tumor suppressor LKB1, in association with accessory proteins STRAD and MO25, phosphorylates AMPKα at Thr172 in the activation loop, and this phosphorylation is required for AMPK activation. AMPKα is also phosphorylated at Thr258 and Ser485 (for α1; Ser491 for α2). The upstream kinase and the biological significance of these phosphorylation events have yet to be elucidated. The β1 subunit is post-translationally modified by myristoylation and multi-site phosphorylation including Ser24/25, Ser96, Ser101, Ser108, and Ser182. Phosphorylation at Ser108 of the β1 subunit seems to be required for the activation of AMPK enzyme, while phosphorylation at Ser24/25 and Ser182 affects AMPK localization. Several mutations in AMPKγ subunits have been identified, most of which are located in the putative AMP/ATP binding sites (CBS or Bateman domains). Mutations at these sites lead to reduction of AMPK activity and cause glycogen accumulation in heart or skeletal muscle. Accumulating evidence indicates that AMPK not only regulates the metabolism of fatty acids and glycogen, but also modulates protein synthesis and cell growth through EF2 and TSC2/mTOR pathways, as well as blood flow via eNOS/nNOS.

Conclusion

The peptide with a sequence of SEQ ID NO. 1 is working through the AMPK pathway. In skeletal muscle activation (phosphorylation) of AMPK leads to phosphorylate ACC which promotes fatty acid oxidation. This is a very different pathway to that of Insulin, as shown in the gene expression profile in skeletal muscle cells described below.

Example 19

Gene Expression Study
Methodology

Over- and under-gene expression to negative control of the top 50 genes for insulin and the peptide of SEQ ID NO. 1 was investigated.

A volume of 2 ml of HSkMC cells were seeded in a 6 cm plate, pre-coated with collagen, at a concentration of 2×10^5 cells. Cells were allowed to adhere overnight at 37° C. 5% CO2 and the following day the growth media was replaced with 2 ml of cell differentiation media and returned to the incubator at 37° C. 5% CO2. The cell differentiation media was changed every 2 days for a period of 6 days, until the HSkMC cells were fully differentiated into myotubes. On day 7, the cell differentiation media was replaced with 2 ml of basal media and starved overnight at 37° C. 5% CO2.

On the day of the experiment, the starvation media was removed and replaced with 2 ml of basal media containing 0.5 ug/ml of SEQUENCE ID NO: 1. Untreated cells were run in parallel. The cells were incubated in this treatment for a period of 20 min at 37° C. 5% CO2, at which point the treatment media was removed and the cells were scraped in 1 ml of PBS. The cell suspension was pelleted in a microcentrifuge at 1500 rpm for 5 min, and the supernatant was removed. The cells were immediately flash frozen in liquid nitrogen and transferred to a −80° C. freezer for storage until dispatched to CROs.

To determine gene expression, Agilent Single Color experiment was performed by Elda Biotech using a Agilent G2565CA microarray scanner system. RNA were extracted from cells and then hybridized to Agilent Human Gene Expression Microarray. The following kits were used: Qiagen Rneasy, Agilent RNA 6000 Nano, LowInput QuickAmp labeling, RNA Spike In (one color), Hi RPM GE Hybridisation Kit Large, Gene Expression Wash Pack. The experiment used a SurePrint G3 Human Gene Expression v3 8×60K microarray. Each sample had three replicates. Samples passed RNA quality and quantity checks. Subsequent data analysis was performed using the Bioconductor package limma.

Raw intensity data was background corrected with the normexp method and an offset of 50 and quantile normalised, which resulted in expression measures in log 2. Using ComBat, batch-effect correction was applied to adjust for a separation by replicate number revealed by principal component analysis. Then, empirical Bayesian analysis was applied. Differential expression was computed based on comparison to untreated samples, and assessed using a moderated t-statistic. To correct for multiple testing, the resulting p-value was adjusted using the Benjamini and Hochberg's method. No differential expression was detected under an adjusted p-value threshold of 0.05. Instead, a raw p-value threshold of 0.001 was used. Genes having an absolute fold change value superior to 1.3 are shown in the following lists.

List of Significantly Up and Down Regulated Genes and their Fold Changes (Microarray Gene Expression)

Up-Regulated Genes for Insulin Treatment:
ABCA9,ACIN1,ADAP2,AKIRIN2,ALG3,AMN,ANKS3,
ANP32AIT1,ARGLU1,ARHGEF35,ARPC5L,ASAP1IT1,
ATP5H,ATP8,AURKAPS1,BMS1P6,BOD1L1,BRD3,
BROX,C12orf65,C14orf169,C20orf96,C21orf59, C4orf33,
C5orf24,C5orf58,C6orf47,CACNA1A,CASC15,
CATSPER2P1,CBX5,CCDC102B,CCNL1,CCNT2-AS1,
CD86,CDK11B,CENPC,CFAP36,CHD3,CIAO1,CLASRP,
CMTM8,COPG2IT1,CRHR1IT1,CWC22,
DKFZP586B0319,DKFZp686M1136,DPP9AS1,DRAP1,
DRD4,DYX1C1,EIF4G3,EIF5,EPSTI1,EXOC1,
FAM127C,FAM155AIT1,FAM173A,FAM212A,
FAM71F1,FASTKD1,FIP1L1,FLJ11292,FLJ13773,FTSJ3,
GABPB1AS1,GADD45B,GATA2,GBP2,GOLGA2P6,
GOLGA6L4,GPATCH11,GPR135,GRIN2D,GSK3A,
HEBP2, HMGB1,HMGB3P1,HNRNPA1L2,HOXBAS1,
HOXC9,HOXD8,ID1,IER2,IFI44,IFT172,IGF1R,
IGF2BP2,KANK3,KCTD3,KIAA1654,KIZ,KLF17,
KRTAP19-2,KRTAP411,LDHAL6A,LINC00083,
LINC00504,LRRC37A2,MALAT1,MAP3K10,MAP3K3,
MBNL1,MIDN,MIR2 2HG,MIR612,MPV17L2,MRE11A,
MTA2,MYO1C,MZF1,NAMPT,NBPF8,ND4L,NF1P2,
NIPBL,NOL8,N OP58,NPIPB5,NR2C1,OLA1,PAK1IP1,
PCDHGA2,PDCD6IP,PDGFRB,PFDN4,PGBD2,PGF,
PGM5P2,P MAIP1,PNPLA8,POU2F1,PP12719,PPIG,
PPP6R1,PRKAG2,PRO2852,PRPF40A,PRR4,PSMA4,
PTMA,R ALBP1,RC3H2,RCC1,REP15,RHOB,RN7SL1,
ROM1,RPLP1,RPS6KC1,SAMD11,SFSWAP,SH3KBP1,S
LC25A34,SLFN5,SMARCC1,SMCR6,SMIM11,SNAI1,
SNAR-A3,SNAR-B2,SNAR-D,SNAR-F,SNARG2,
SNARH,SNHG9,SNORA10,SNORD97,SNORD99,
SOCS3,SOX8,SRP19,SRSF11,SSC5D,STAR,TAB2,TAF3,
TC EAL7,TCF7L1,TFPI2,THOC2,TINAGL1,TNFAIP8L1,
TOPORS,TRANK1,TRAPPC10,TXLNG,UBE2Q2P1,
UBN2,VASP,VHL,VPS37D,YBX3,ZBTB2,ZCCHC17,
ZMYND11,ZNF503-AS2,ZSWIM4,ZSWIM6

Down-Regulated Genes for Insulin Treatment:
ABHD2,ACTA2,ACVR1,ADAMTS9,ADCY6,ADD3,AD-
PRHL2,AGTRAP,ALAD,AMZ2P1,ANXA2P1,A P2B1,
ARMCX6,ATP5A1,ATP5B,ATP5G1,ATP6V0E1,ATRAID,
AXL,BFAR,BOD1,BRF2,C1orf43,C5orf 15,C9orf78,
CA12,CAV1,CD47,CD82,CD9,CDC123,CDC42BPA,
CDC42EP4,CHST14,CHST3,CHSY3,CL MP,CLPTM1L,
CLU,CNPPD1,COLGALT1,COPG1,COPZ2,CRISPLD2, CRTC3,CSRP1,CTSLP8,CYB5D2,CYB5R1,DAG1, DANCR,DEK,DENND4C,DFNA5,DHRS1,DLST, DNAJB9,DNASE1L1,DNASE2,DPA GT1,EBF2,EI24, EIF2B4,EIF3I,EIF3K,EIF3L,EMC3,ENDOD1,ENO2, ENPP4,EPRS,ESYT1,ESYT2,EXT1, EZH1,FAF1, FAM57A,FAM96A,FAS,FHOD1,FKBP14,FLII,FLNB, FN3KRP,G6PD,GABARAP,GALM,G ARS,GBA,GBAP1, GDE1,GJA1,GOLM1,GPRC5A,GPX3,GREM1,GSTM2, HDDC2,HEPH,HEXB,HLA-A,HLA-DMA,HLA-DPA1, HLA-DPB1,HLADRB4,HOOK2,HTRA2,IDH1,IDS, IFIT3,IGF2R,IGFBP6,IL10RB,IL11RA,ILK,ITGA3, ITGAE,JKAMP,KI F3B,KLHDC2,LAMA2,LAPTM4B, LASP1,LUM,MAGED1,MAN2A1,MAN2B2,MANBA, MANSC1,MA P2K1,MFSD5,MKNK1,MLEC,MMGT1, MPHOSPH8,MRPL17,MRPL37,MRPS18A,MTFR1L, MTHFD1L, MUL1,MYD88,NBAS,NDRG1,NDUFA9, NIF3L1,NLRP1,NME6,NPC1,NSMCE1,NUDT2,OAT, OLFML3,OXA1L,P4HA2,P4HTM,PAMR1,PARP6, PCYOX1,PDE6D,PDLIM1,PDXP,PEA15,PEAR1,PEF1, PELO, PGAM1,PGM1,PGRMC1,PHB2,PIGH,PLEKHG4, PLP2,PLS3,PPAP2B,PPIAL4B,PPL,PRKAB1,PRMT5, PRNP,PRPF8,PRPS1,PRRC1,PSAP,PSMB8,PSMD10, PTGS1,QSOX2,RAB11FIP5,RAF1,RARG,RBM23, RER1, RHBDD2,RP9,RPL29P2,RPL5,RPRD1B,RPUSD4,RTCB, SCAMP2,SCG2,SDC4,SDHB,SEC22C,S EC23A,SEC63, SENP3,SEP15,SERINCLSERINC3,SF3B2,SFXN3,SGCE, SIAE,SLBP,SLC12A4,SLC1A1, SLC35B1,SLC35E2, SLC35E3,SLC39A1,SLC39A7,SMPD1,SNORA70F, SNX11,SNX19,SPPL2A,SPRED 2,SRPR,STAU1, STEAP1B,STIM1,STK38,STX18,SYPL1,SYT11,TAF11, TAPBPL,TBC1D22B,TCN2,TC TA,TES,TFG,TFRC, TGFB3,TM7SF2,TM9SF1,TMBIM1,TMCO1,TMCO3, TMED10,TMEM138,TMEM1 79B,TMEM185A, TMEM216,TMEM50A,TNS1,TNS3,TPI1P2,TRAM2, TRIM16L,TSPAN9,TUB,TUBA1A,UBAC2,UBE2E3, UNC50,USO1,USP24,VCL,VOPP1,VPS25,VPS33B,WAS, WBP1,WNT5B,ZCCHC24, ZFP91,ZMAT3,ZMYM6NB, ZNF384,ZNF667-AS1

Up-Regulated Genes for SEQ ID 1 Treatment
ACAA2,ACSL1,ACVR1,ADAR,ADD3,ADIPOR2,AD- PRM,AGTR1,AKR1B10,AKR1B15,ALAD,ALG14, AMZ2,AMZ2P1,ANKHD1,APOL6,ASCC1,ASH2L,ATF5, ATG3,ATP5A1,ATP5C1,ATP5J2,ATP6V0E1, ATP6V1B2, ATXN7L3B,B2M,B4GALT5,BBS4,BIRC5,BLMH,BOD1, BRK1,BST1,BTF3,C11orf73,C16or f58,C17orf62, C19orf52,C1orf43,C4orf3,C5orf15,C5orf58,C7orf25, C8orf33,CALM1,CCNBIIP1,CCNG2,C D47,CDCA8, CFDP1,CHAMP1,CHCHD3,CHURC1,CISD3,CKAP5, CLMP,CLTA,C0A1,COG3,COG8,C OPS8,COX14,CPD, CSTF1,CSTF2T,CTCF,CYB5R3,CYCS,CYTB,DCTN6, DCTPP1,DDX21,DDX5,DDX 60,DECR1,DERL1, DFNA5,DHX15,DHX32,DRG1,DSTYK,EFNB3,EMCN, EMG1,ENDOD1,ENPP2,ERI CH1,ETFA,EZH1,F8A2, FAM96A,FH,FOS,FOSB,FUCA2,FUNDC2, GABARAPL2,GADD45B,GALNT15,GAS1,GATS,GBF1, GBP1,GDE1,GGA3,GJA1,GLB1,GLUL,GOLM1, GPR89B,GRAMD3,GSTA4,GTF2E 2,H2AFZ,HES1, HEXB,HIBADH,HIST1H4F,HIST2H2AA4,HMGN3, HMGN4,HNRNPM,HOOK2,HSPB8,IDH1,IER3,IFI44L, IFIT1,IFT88,IMMP2L,IMPA2,INTS12,KAT7,KCTD10, KDELR3,KIAA0196,KIF2C,K IFAP3,KLF10,KLHL18, LAP3,LAPTM4B,LDHA,LDLR,LETMD1,LMAN2L, LMO4,LOXL4,LRP10,LSM 1,LTBP2,LYPD6B,LYSMD2, MAD2L1BP,MANBA,MAT2A,MCL1,MEDAG,MFAP1, MIFAS1,MIOS,MKKS,MMGT1,MRFAP1,MROH5, MRPL20,MRPL33,MYD88,NDN,NDRG1,NDUFV2,NKA P,NOLC1,NT5C3B,NT5E,OAS1,OAT,OAZ2,ODF3L2, OLFML1,OLFML2B,OSBP,OSTC,OTUD1,OXCT 1,PAIP2,PARL,PARP9,PATL1,PCED1A,PDE1A,PEAR1, PELO,PFKL,PFKM,PGAM1,PGK1,PGM1,PIG H,PLE- KHJ1,POGK,POLD2,POLR2B,POLR3F,PPA2,PPAP2B, PPAPDC2,PPL,PPP2CB,PPP2R2A,PQLC2 L,PRC1, PRDM4,PSMA2,PSMA5,PSMD10,PSME4,PTGS1, PTP4A1,PTTG2,RAB31,RAB32,RAB9BP1,R ABEP1, RAC1,RASL11B,RCN1,RHOA,RIOK1,RNASEL, RNF121,RNF146,RNLS,RPA2,RPL15,RPL21P4 4,RPP38, RTCB,SEC22C,SEC23IP,SENP2,SEP15,SERP2, SERTAD4,SETX,SFRP1,SFT2D1,SGCE,SIAE,S LBP, SLC25A12,SLC25A25,SLC30A9,SLC35B1,SLC44A1, SLC9A3R1,SMAD7,SMIM19,SNAPC5,SNH G3,SNORD11619,SNORD96A,SNX19, SRRD,SRSF2, STARD7,STK16, STOM,STOML2,SUCLA2,SUCLG1, SYNGR4, SY T11,TASP1,TCP1,TFRC,TGFBR2, TIMM17A,TIMMDC1,TINF2,TMC01,TMEM173, TMEM203,TMEM2 30,TMEM50A,TMEM50B,TMEM60, TMX2,TNC,TNS3,TOMM22,TOR1A,TOR3A,TP53I3, TPBG,TPI1,T RIB1,TRIL,TUBB3,TUG1,TUSC3,UBE2C, UBE2E3,UBE2L3,UGCG,UNC119,UQCRFS1,USP18, USP24, USP34,VAMP7,VDAC3,VIMAS1,VOPP1,WARS, WDR36,WDR48,WDR61,WDYHV1,WLS,WRB, XPNPEP1,XRCC6BP1,YIPF6,ZFP9 1,ZMAT2,ZNF157, ZNF281,ZNF384,ZNF426,ZNF564,ZNF696,ZNF75D, ZSCAN32

Down-Regulated Genes for SEQ ID 1 Treatment
ABLIM1,ACTR2,ADAM20,AHSA2,ALDH1L2,AMN, APC,APOLD1,ARGLU1,ARPC5,ASAP1IT1,ATXN2, ATXN3,AURKAPS1,BCL2L11,BCLAF1,BRD1,BTG3, C14orf169,C1QTNF5,C20orf141,C20 orf96,C5orf28, C6orf203,CACNA2D1,CCDC102B,CCDC125,CCDC6, CCNG1,CCNL1,CD46,CEACAM19,CENPC,CHML, CIRBP,CNN2,COL1A1,COL4A1,CRYBG3,CWC22, DDX3X,DENND4B,DHRS3,DIAPH 2,DLG1,DNAJB4, DNAJC3,DOCK6,DPEP3,DSE,DST,DYNLT3,DZIP3, EDIL3,EGLN1,EIF4G3,ELF2,EL P2,EPC1,FAM111A, FAM177A1,FBXO32,FERMT2,FGF7,FNIP1,FOSL2, FOXN2,FRYL,GABPB1-AS1,GABRE,GLS,GOLGA6L4, GOLGA8R,GOLIM4,GPATCH11,GPR135,GTF2H5, HCG11,HCG18,HIF 1A,HNRNPA1,HOOK3,HOXC6, HSP9OAA1,HSP9OAA2P,HSPA1B,HSPA4,HSPH1,HTT, IGF2R,ITGB3,J MJD4,KCNMB2AS1,KCTD3,KDM2A, KIAA1143,KIZ,KRAS,KRT8P12,LCE1D,LINC01506, LOX,LPGAT1,LPP,LRP12,L RRC3C,MACF1,MAMDC2, MAP1B,MAP2K3,MAP3K10,MATR3,MBNL1,MBTPS2, MDM2,MDM4,ME D15,METTL15,MGC24103, MUSTN1,MYH3,MYH8,MYLPF,MYO6,MZF1,NAB1, NADK,NADK2,NBE AL1,NCKAP5,ND6,NEK7,NKTR, NR2C1,NRN1,OFD1,PAPOLA,PAWR,PAXBP1,PBRM1, PCDHGA2,P DE1C,PDZD8,PEAK1,PFDN2,PGBD2, PHF1,PJA2,PLOD3,POLR2J2,PPME1,PPP1R14A, PPP1R16B,PPP 1R2,PPP1R3B,PRO2852,PRPF40A, PRUNE2,PTPN11,PUM2,PXK,RAB12,RAB2A,RBM10, RCN2,REEP3,REST,RHOBTB3,RHOQ,RIOK3,RNF19B, RNF215,RNPC3,ROBO1,ROCK1,RPL26L1,SAMD14, SDPR,S EPT7P2,SERP1,SFSWAP,SGIP1,SH3KBP1,SKI, SLC35A5,SLC46A3,SLC7A5,SMARCC1,SMARCC2,S MN1,SNARH,SNORA16A,SNORD89,SOX6,SPHAR, SREK1,SRSF11,STT3B,STX2,TAB2,TFPI,THBS1, THOC2,TIN AGL1,TMA16,TMEM106C,TMEM26AS1, TNFAIP8,TOB1,TTC28,TXLNG,UBE2D1,UBE2Q2P1, UBL3,UCHL5,UPF2,UPF3A,USP15,USP33, UTRN, UVSSA,WHAMMP1,WNT3,YBX3,YWHAZ,ZBTB2, ZFC3H1,ZMYND11,ZNF22,ZNF37A,ZNF4 29,ZNF525, ZNF532,ZNF626,ZRANB2,ZSWIM8

Example 20

Proteomics
Methodology
Protein levels were obtained using LC/MS/MS. Statistical analysis of protein counts yielded under- and over-abundant proteins. Only absolute protein level fold change values over 0.379 were retained. For all these proteins, associated transcript fold changes from microarray analysis are presented.

Mass spectrometry was performed by MSBioworks. Cell pellets were lysed in 100 μL of modified RIPA buffer by sonication. Quantitation was performed using Qubit fluorometry. 20 μg of each sample was separated on a 4-12% bis tris gradient gel using the MOPS buffer. The gel was stained with coomassie and each lane was excised into 20 equally sized segments. Gel pieces were processed using a robot (ProGest, DigiLab) with the following protocol:

Washed with 25 mM ammonium bicarbonate followed by acetonitrile.
Reduced with 10 mM dithiothreitol at 60° C. followed by alkylation with 50 mM iodoacetamide at RT.
Digested with trypsin (Promega) at 37° C. for 4 h.
Quenched with formic acid and the supernatant was analyzed directly without further processing.

The digests were analyzed by nano LC/MS/MS with a Waters NanoAcquity HPLC system interfaced to a Thermo-Fisher Q Exactive. Peptides were loaded on a trapping column and eluted over a 75 μm analytical column at 350 nL/min; both columns were packed with Luna C18 resin (Phenomenex). A 30 min gradient was employed (10 h total per sample). The mass spectrometer was operated in data-dependent mode, with MS and MS/MS performed in the Orbitrap at 70,000 FWHM and 17,500 FWHM resolution, respectively. The fifteen most abundant ions were selected for MS/MS. Data were searched using a local copy of Mascot with the following parameters:

Enzyme: Trypsin; Database: Swissprot Human (forward and reverse appended with common contaminants); Fixed modification: Carbamidomethyl (C); Variable modifications: Oxidation (M), Acetyl (Protein N-term), Pyro-Glu (N-term Q), Deamidation (NQ); Mass values: Monoisotopic
Peptide Mass Tolerance: 10 ppm; Fragment Mass Tolerance: 0.02 Da; Max Missed Cleavages: 2
Mascot DAT files were parsed into the Scaffold software for validation, filtering and to create a non-redundant list per sample. Data were filtered 1% protein and peptide level false discovery rate (FDR) and requiring at least two unique peptides per protein. Up and down-regulated protein lists were then estimated.

Mass Spectrometry

The digests were analyzed by nano LC/MS/MS with a Waters NanoAcquity HPLC system interfaced to a Thermo-Fisher Q Exactive. Peptides were loaded on a trapping column and eluted over a 75 μm analytical column at 350 nL/min; both columns were packed with Luna C18 resin (Phenomenex). A 30 min gradient was employed (10 h total per sample). The mass spectrometer was operated in data-dependent mode, with MS and MS/MS performed in the Orbitrap at 70,000 FWHM and 17,500 FWHM resolution, respectively. The fifteen most abundant ions were selected for MS/MS.

Example 21

QPCR on Specific Genes of Interest and their Fold Change.
Experimental Procedure Quantitative PCR was performed using a TaqMan probe based method, where target mRNA expression was quantified relative to the expression of the B2M housekeeping gene. A master mix containing primer/probe and Taqman® Gene Expression Master Mix (ABI Biosystems, CA, USA) was added to 1 μl of cDNA template. A final volume of 10 μl was pipetted into a well of a 96-well Lightcycler plate (Sarstedt, Nümbrecht, Germany) in duplicate and real time PCR was performed on a Roche Lightcycler 96 (Roche Diagnostics, Basal, Switzerland) real time thermal cycler. The threshold cycle (Ct) for each well was calculated using the instrument software. Data analysis was based on the ΔΔCt method with raw data normalised by the B2M housekeeping gene included on the plate. Results are expressed as fold change over control.

QPCR results (methods of treatment remains the same; concentration of SEQ ID 1 remains 0.5 ug/ml)

Glut 4, LEPR, Adiponectin, Leptin are Related to Glucose Metabolism. Other Relate to Muscle Synthesis and Degradation

| Gene name | Fold change |
| --- | --- |
| Adiponectin | 1.07 |
| Leptin | 0.51 |
| PPARGC1A | 0.69 |
| PRKAG3 | 0.35 |
| COX4I1 | 0.85 |
| NRF1 | 0.54 |
| SIRT | 0.41 |
| UQCRB | 2.56 |
| FBXO32 | 1.00 |
| GLUT4 | 1.95 |
| HSPA2 | 0.67 |
| LEPR | 1.20 |
| MYOG | 0.70 |
| TRIM63 | 0.70 |
| ACVR2B | 0.48 |
| MSTN | 0.17 |

Example 22

Investigating the Effect of a Synthetic Peptide (SEQ ID NO 1) on Blood Glucose Management in a Mouse Model of Obesity and Diabetes Experimental Procedure Animal Description:
  Species—KK.Cg-Ay/J (KKAY mouse)
  Source—Jackson Laboratories
  Age—12 weeks of age
  Gender—Male
  Randomization—Based on baseline fasting glucose
Housing and Feeding:
  Acclimation—Not less than five days
  Housing
    Mice will be housed on a 12 hr light/dark cycle
    No more than 4 mice per cage depending on size
    Ventilated cage rack system
  Diet—Standard rodent chow and water ad libitum
Design:
  Route of administration:—Subcutaneous injection
  Dose Volume(s)—10 mL/kg
  Dose Levels—Test articles: 100 μM/kg, Metformin: 250 mg/kg
  Number per group—10
  Total number of animals—30

TABLE 1 study design

| Treatment | Group size | Dose | Days of dosing | Dose and route | Evaluations/endpoints |
|---|---|---|---|---|---|
| KKAY-vehicle | 10 | n/a | 14 | Subcutaneous injection | Bodyweight: (ONCE/Week); Food/water intake Daily Fasting glucose: (2/week) OGTT (Day 12 or13) HbA1C (ONCE/Week) Terminal Blood Serum Tissue collection Liver, muscle, pancreas |
| KKAY-metformin | 10 | 250 mg/kg | 14 | Subcutaneous injection | Bodyweight: (ONCE/Week); Food/water intake Daily Fasting glucose: (2/week) OGTT (Day 12 or13) HbA1C (ONCE/Week) Terminal Blood Serum Tissue collection Liver, muscle, pancreas |
| KKAY-SEQ ID 1 | 10 | 100 um/kg | 14 | Subcutaneous injection | Bodyweight: (ONCE/Week); Food/water intake Daily Fasting glucose: (2/week) OGTT (Day 12 or 13) HbA1C (ONCE/Week) Terminal Blood Serum Tissue collection Liver, muscle, pancreas |

Oral Glucose Tolerance Test in KKAY Mice

During OGTT, mice were bled for baseline glucose and insulin at −30 min (baseline). This was immediately followed by test articles administration. 30 min later, i.e. at 0 min, all mice were administered a glucose solution (2 g/kg) via oral gavage administration. After glucose challenge, blood glucose levels were measured according to the schedule below.

TABLE 2

OGTT Treatment Paradigm

| Time (minutes) | Treatment | Measurement |
|---|---|---|
| −30 | | Baseline Glucose/Insulin |
| 0 | Vehicle/Metformin/test compounds injection | |
| 20 | | Glucose/Insulin |
| 40 | | Glucose/Insulin |
| 60 | | Glucose/Insulin |
| 120 | | Glucose/Insulin |

The results are illustrated in FIGS. 18 to 20. FIG. 18 illustrates fasting blood glucose after 5 days of treatment with a peptide of SEQ ID NO. 1 in KKAY mice. FIG. 19 illustrates fasting blood glucose after 7 days of treatment with a peptide SEQ ID NO. 1 in KKAY mice. FIG. 20 illustrates Body weight of KKAY mice after 13 days of treatment with a peptide of SEQ ID NO. 1.

Conclusion

Treatment with a peptide of SEQ ID NO.1 significantly reduced blood glucose after 7 days of treatment. Treatment with a peptide of SEQ ID NO. 1 did not cause an increase in body weight as many anti-diabetic treatments do. SEQ ID NO. 1 reduced body weight in the treatment group relative to the untreated group.

Example 23

Anti-Oxidation Assay (DPPH Radical Scavenging Activity Assay)

The DPPH test was conducted using the method described in Lin et al. (Lin S Y, Wang J, Zhao P, Pang Y, Ye H Q, Yuan Y, Liu J B and Jones G, Optimized antioxidant peptides fractions preparation and secondary structure analysis by MIR. Int J BiolMacromol 59:151-157 (2013)).

DPPH radicals were dissolved in ethanol at a final concentration of 0.1 mM. The peptides and ascorbic acid (positive control) were dissolved in deionized water to obtain the concentration tested.

In a 96 well-plate, the samples were prepared as following: 100 µL DPPH solution 0.1 mM, 100 µL peptide solution and 100 µL ethanol were mixed per well.

Ascorbic acid was prepared as following: 100 µL DPPH solution 0.1 mM, 100 µL ascorbic acid solution and 100 µL ethanol were mixed per well.

Blank was prepared as following: 100 μL DPPH solution 0.1 mM, 200 μL ethanol were mixed per well.

Three wells were used per conditions tested.

The plate was incubated in the dark at 25° C. for 30 min. The absorbance at 517 nm was then measured using a plate reader.

The DPPH radical scavenging activity (%) was calculated as follow:

DPPH radical scavenging activity (%)=[1−(Absorbance sample/Absorbance blank)]×100

The data were presented as mean of percentage of DPPH radical scavenging activity+/−standard deviation.

Example 24

Inflammatory Response Assay

TNF-alpha is secreted by macrophages in response to stimulation by endotoxins such as lipopolysaccharides (LPS). TNF-alpha is thought to be involved in systemic inflammation and dysregulation of TNF-alpha production is thought to be involved in many diseases. The Bio legend assay is a sandwich ELISA kit that is designed for the accurate quantitation of human TNF-alpha from cell culture supernatant, serum or plasma.

THP-1 monocytes were seeded in a 96 well plate at 10,000 cells per well in RPMI containing 10% fetal calf serum (FCS), 1% Pen/strep, 1% L-glutamine, 100 nM PMA and allowed to differentiated for 72 h prior to experimentation. Following differentiation, the cells were incubated with 100 ng/ml, 10 ng/ml or 1 ng/ml synthetic peptide for 24 h respectively. Following treatment, the cells were stimulated with 10 ng/ml LPS for 5 h and the quantity of TNF-alpha in the supernatant determined using the Biolegend assay ELISA kit.

Results were calculated as a percentage of the untreated control. An increase in optical density reading indicates greater quantity of TNF-alpha release into cell culture supernatant. All experiments were prepared in duplicate on three plates (6 wells/conditions). Significance was calculated using Students t-test (*$p<0.05$ compared to control, $p<0.01$ compared to control, * $p<0.001$ compared to control).

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A composition comprising a peptide of up to 50 amino acids, the peptide comprising the amino acid sequence of SEQ ID NO: 1, or a variant thereof, the variant comprising no more than 3 amino acid alterations relative to SEQ ID NO: 1.

2. The composition of claim 1, wherein the peptide comprises the amino acid sequence of SEQ ID NO: 1, or a variant thereof, the variant comprising no more than 1 amino acid alteration relative to SEQ ID NO: 1.

3. The composition of claim 1, in which the peptide is modified by modifications of side chains, incorporation of a protecting group, incorporation of up to 5 unnatural amino acids, cyclisation, conjugation to a conjugation partner, covalent binding to a binding partner, fusion to a fusion partner, PEGylation, amidation, acylation lipidation, or the incorporation of a cross-linker.

4. The composition of claim 1, in which the peptide is modified with a modification group selected from polyethylene glycol (PEG), monomethoxy-polyethylene glycol, dextran, pyrrolidone) polyethylene glycol, propylene glycol homopolymers, a polypropylene oxide/ethylene oxide copolymer, polypropylene glycol, polyoxyethylated polyols, polyvinyl alcohol, colominic acids, carbohydrate based polymers, polymers of amino adds, or biotin derivatives; or that is modified with a N-terminal or C-terminal protecting group.

5. A pharmaceutical composition comprising a peptide of up to 50 amino acids, the peptide comprising the amino acid sequence of SEQ ID NO: 1, or a variant thereof, the variant comprising no more than 3 amino acid alterations relative to SEQ ID NO: 1, for use in a method of ameliorating diabetes or pre-diabetes, a method of lessening the symptoms of diabetes or pre-diabetes, a method of delaying the onset or progression of diabetes or pre-diabetes, and/or a method of reducing the incidence of diabetes or pre-diabetes in a treated population of diabetics or pre-diabetics.

6. The pharmaceutical composition of claim 5, wherein the peptide comprises the amino acid sequence of SEQ ID NO: 1, or a variant thereof, the variant comprising no more than 1 amino acid alteration relative to SEQ ID NO: 1.

7. The pharmaceutical composition of claim 5, further comprising a suitable pharmaceutical carrier.

8. The pharmaceutical composition of claim 5, wherein the diabetes is Type 2 diabetes.

9. The pharmaceutical composition of claim 5, in which the composition is to be administered with one or more agents selected from the group consisting of: insulin; insulin analogues; insulin derivatives; glucagon-like peptide 1; glucagon-like peptide 2; derivatives glucagon-like like peptide 1; derivatives of glucagon-like peptide 2; analogues of glucagon-like peptide 1; and analogue of glucagon-like peptide 2.

10. The pharmaceutical composition of claim 5, formulated for oral or parenteral administration to a patient.

11. The pharmaceutical composition of claim 5, in which the peptide is modified by modifications of side chains, incorporation of a protecting group, incorporation of up to 5 unnatural amino acids, cyclisation, conjugation to a conjugation partner, covalent binding to a binding partner, fusion to a fusion partner, PEGylation, amidation, acylation lipidation, or the incorporation of a cross-linker.

12. The pharmaceutical composition of claim 5, in which the peptide is modified with a modification group selected from polyethylene glycol (PEG), monomethoxy-polyethylene glycol, dextran, poly-(N-vinyl pyrrolidone) polyethylene glycol, propylene glycol homopolymers, a polypropylene oxide/ethylene oxide copolymer, polypropylene glycol, polyoxyethylated polyols, polyvinyl alcohol, colominic acids, carbohydrate based polymers, polymers of amino adds, or biotin derivatives; or is modified with a N-terminal or C-terminal protecting group.

* * * * *

UNITED STATES PATENT AND TRADEMARK OFFICE
CERTIFICATE OF CORRECTION

PATENT NO. : 10,729,636 B2
APPLICATION NO. : 16/466124
DATED : August 4, 2020
INVENTOR(S) : Nora Khaldi and Cyril Lopez Page 1 of 1

It is certified that error appears in the above-identified patent and that said Letters Patent is hereby corrected as shown below:

In the Claims

Column 100, Claim 4, Line 58:
"…dextran, pyrrolidone) polyethylene…" should be replaced with -- …dextran, poly-(N-vinyl pyrrolidone) polyethylene… --

Column 100, Claim 4, Lines 62-64:
"…; or that is modified with a N-terminal or C-terminal protecting group." should be replaced with -- …; or is modified with a N-terminal or C-terminal protecting group. --

Column 101, Claim 9, Lines 20-21:
"…; derivatives glucagon-like like peptide 1;…" should be replaced with -- …; derivatives of glucagon-like peptide 1;… --

Signed and Sealed this
Seventeenth Day of November, 2020

Andrei Iancu
*Director of the United States Patent and Trademark Office*

SEQUENCE LISTING

```
<160> NUMBER OF SEQ ID NOS: 85

<210> SEQ ID NO 1
<211> LENGTH: 11
<212> TYPE: PRT
<213> ORGANISM: Artificial Sequence
<220> FEATURE:
<223> OTHER INFORMATION: Peptide

<400> SEQUENCE: 1

Trp Lys Asp Glu Ala Gly Lys Pro Leu Val Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Peptide

<400> SEQUENCE: 2

Trp Lys Glu Glu Ala Gly Lys Pro Leu Val Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Peptide

<400> SEQUENCE: 3

Phe Lys Asp Glu Ala Gly Lys Pro Leu Val Lys
1               5                   10

<210> SEQ ID NO 4
<211> LENGTH: 11
<212> TYPE: PRT
```

```
<213> ORGANISM: Artificial Sequence
<220> FEATURE:
<223> OTHER INFORMATION: Peptide

<400> SEQUENCE: 4

Trp Lys Asp Glu Ala Gly Lys Pro Met Val Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Peptide

<400> SEQUENCE: 5

Trp Lys Asp Glu Ala Gly Arg Pro Leu Val Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Peptide

<400> SEQUENCE: 6

Trp Arg Asp Glu Ala Gly Lys Pro Leu Val Lys
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Peptide

<400> SEQUENCE: 7

Trp Lys Asp Glu Ala Gly Lys Pro Leu Met Lys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Peptide

<400> SEQUENCE: 8

Trp Lys Asp Gln Ala Gly Lys Pro Leu Val Lys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Peptide

<400> SEQUENCE: 9

Trp Lys Asp Glu Ala Thr Lys Pro Leu Val Lys
1               5                   10

<210> SEQ ID NO 10
<211> LENGTH: 11
<212> TYPE: PRT
<213> ORGANISM: Artificial Sequence
```

```
<220> FEATURE:
<223> OTHER INFORMATION: Peptide

<400> SEQUENCE: 10

Tyr Lys Asn Glu Ala Gly Lys Pro Leu Val Lys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Peptide

<400> SEQUENCE: 11

Trp Lys Asn Glu Ser Gly Lys Pro Leu Val Lys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Peptide

<400> SEQUENCE: 12

Trp Lys Asp Glu Ala Gly Lys Thr Leu Val Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Peptide

<400> SEQUENCE: 13

Phe Lys Asp Glu Ala Thr Lys Pro Leu Val Lys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Peptide

<400> SEQUENCE: 14

Phe Lys Asp Glu Ala Gly Lys Pro Leu Ile Lys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Peptide

<400> SEQUENCE: 15

Trp Lys Asp Glu Ala Gly Lys Thr Leu Leu Lys
1               5                   10

<210> SEQ ID NO 16
<211> LENGTH: 11
<212> TYPE: PRT
<213> ORGANISM: Artificial Sequence
<220> FEATURE:
```

<223> OTHER INFORMATION: Peptide

<400> SEQUENCE: 16

Trp Lys Asn Glu Ala Gly Lys Pro Val Val Lys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Peptide

<400> SEQUENCE: 17

Trp Lys Asp Glu Ala Gly Arg Thr Leu Val Lys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Peptide

<400> SEQUENCE: 18

Trp Glu Asp Glu Ser Gly Lys Pro Leu Leu Lys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Peptide

<400> SEQUENCE: 19

Trp Lys Glu Glu Ala Gly Lys Pro Ile Val Gln
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Peptide

<400> SEQUENCE: 20

Tyr Lys Asn Glu Ala Gly Lys Pro Leu Val Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Peptide

<400> SEQUENCE: 21

Trp Lys Asp Gln Ala Thr Arg Pro Leu Val Lys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Peptide

```
<400> SEQUENCE: 22

Trp Lys Asp Glu Ser Gly Lys Pro Val Leu Lys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Peptide

<400> SEQUENCE: 23

Trp Gln Asp Asp Ser Gly Lys Pro Leu Val Lys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Peptide

<400> SEQUENCE: 24

Trp Lys Asn Glu Ala Gly Lys Thr Leu Leu Lys
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Peptide

<400> SEQUENCE: 25

Trp Lys Asp Lys Ala Gly Glu Pro Leu Val Arg
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Peptide

<400> SEQUENCE: 26

Trp Lys Asp Glu Ala Gly Asn Pro Leu Val Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Peptide

<400> SEQUENCE: 27

Cys Lys Asp Glu Ala Gly Lys Pro Leu Val Lys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Peptide
```

```
<400> SEQUENCE: 28

Trp Lys Asp Glu Ala Gly Lys Pro Leu Gly Lys
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Peptide

<400> SEQUENCE: 29

Trp Lys Asp Glu Asn Gly Lys Pro Leu Val Lys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Peptide

<400> SEQUENCE: 30

Trp Lys Asp Glu Ala Arg Lys Pro Leu Val Lys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Peptide

<400> SEQUENCE: 31

Trp Lys Asp Glu Ala Gly Lys Pro Leu Val Thr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Peptide

<400> SEQUENCE: 32

Trp Lys Asp Glu Ala Gly Lys Arg Leu Val Lys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Peptide

<400> SEQUENCE: 33

Trp Lys Trp Glu Ala Gly Lys Pro Leu Val Lys
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Peptide

<400> SEQUENCE: 34
```

```
Trp Lys Asp Glu Ala Gly Phe Pro Thr Val Lys
 1               5                  10

<210> SEQ ID NO 35
<211> LENGTH: 11
<212> TYPE: PRT
<213> ORGANISM: Artificial Sequence
<220> FEATURE:
<223> OTHER INFORMATION: Peptide

<400> SEQUENCE: 35

Trp Tyr Asp Met Ala Gly Lys Pro Leu Val Lys
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: Peptide

<400> SEQUENCE: 36

Trp Lys Asp Tyr Glu Gly Lys Pro Leu Val Lys
 1               5                  10

<210> SEQ ID NO 37
<211> LENGTH: 11
<212> TYPE: PRT
<213> ORGANISM: Artificial Sequence
<220> FEATURE:
<223> OTHER INFORMATION: Peptide

<400> SEQUENCE: 37

Trp Lys Arg Glu Ala Gly Lys Pro Gly Val Lys
 1               5                  10

<210> SEQ ID NO 38
<211> LENGTH: 11
<212> TYPE: PRT
<213> ORGANISM: Artificial Sequence
<220> FEATURE:
<223> OTHER INFORMATION: Peptide

<400> SEQUENCE: 38

Trp Lys Leu Glu Lys Gly Lys Pro Leu Val Lys
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: Peptide

<400> SEQUENCE: 39

Trp Lys Asp Glu Ala Gly Lys Pro Cys Val Lys
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: Peptide

<400> SEQUENCE: 40
```

```
Trp Lys Lys Glu Ala Pro Lys Pro Leu Val Lys
1               5                   10
```

<210> SEQ ID NO 41
<211> LENGTH: 11
<212> TYPE: PRT
<213> ORGANISM: Artificial Sequence
<220> FEATURE:
<223> OTHER INFORMATION: Peptide

<400> SEQUENCE: 41

```
Ser Lys Asp Glu Ala Gly Pro Pro Leu Val Lys
1               5                   10
```

<210> SEQ ID NO 42
<211> LENGTH: 11
<212> TYPE: PRT
<213> ORGANISM: Artificial Sequence
<220> FEATURE:
<223> OTHER INFORMATION: Peptide

<400> SEQUENCE: 42

```
Trp Lys His Glu Pro Gly Lys Pro Leu Ala Lys
1               5                   10
```

<210> SEQ ID NO 43
<211> LENGTH: 11
<212> TYPE: PRT
<213> ORGANISM: Artificial Sequence
<220> FEATURE:
<223> OTHER INFORMATION: Peptide

<400> SEQUENCE: 43

```
Trp Lys Asp Glu Arg Glu Lys Pro Phe Val Lys
1               5                   10
```

<210> SEQ ID NO 44
<211> LENGTH: 11
<212> TYPE: PRT
<213> ORGANISM: Artificial Sequence
<220> FEATURE:
<223> OTHER INFORMATION: Peptide

<400> SEQUENCE: 44

```
Trp Lys Gln Glu Ala Gly Lys Pro Trp Arg Lys
1               5                   10
```

<210> SEQ ID NO 45
<211> LENGTH: 11
<212> TYPE: PRT
<213> ORGANISM: Artificial Sequence
<220> FEATURE:
<223> OTHER INFORMATION: Peptide

<400> SEQUENCE: 45

```
Val Lys Asp Glu Ala Lys Lys Pro Leu Val His
1               5                   10
```

<210> SEQ ID NO 46
<211> LENGTH: 11
<212> TYPE: PRT
<213> ORGANISM: Artificial Sequence
<220> FEATURE:
<223> OTHER INFORMATION: Peptide

<400> SEQUENCE: 46

```
Asn Trp Asp Glu Ala Gly Lys Met Leu Val Lys
```

```
<210> SEQ ID NO 47
<211> LENGTH: 11
<212> TYPE: PRT
<213> ORGANISM: Artificial Sequence
<220> FEATURE:
<223> OTHER INFORMATION: Peptide

<400> SEQUENCE: 47

Ile Lys Asp Glu Asp Gly Pro Pro Leu Val Lys
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Peptide

<400> SEQUENCE: 48

Leu Lys Asp Glu Tyr Gly Lys Pro Leu Val Asn
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Peptide

<400> SEQUENCE: 49

Trp Lys Asp Arg Ala Gly Lys Glu Leu Thr Lys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Peptide

<400> SEQUENCE: 50

Trp Lys Asp Glu Ala Gly Lys Pro Leu Pro Val Lys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Peptide

<400> SEQUENCE: 51

Trp Lys Gly Asp Glu Asn Tyr Ala Gly Lys Pro Leu Val Lys
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Peptide

<400> SEQUENCE: 52

Leu Trp Lys Asp Glu Ala Gly Arg Lys Tyr Pro Leu Val Lys
1               5                   10
```

```
<210> SEQ ID NO 53
<211> LENGTH: 12
<212> TYPE: PRT
<213> ORGANISM: Artificial Sequence
<220> FEATURE:
<223> OTHER INFORMATION: Peptide

<400> SEQUENCE: 53

Trp Lys Asp Cys Glu Gly Ala Gly Lys Pro Leu Val
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Peptide

<400> SEQUENCE: 54

Trp Lys Asp Glu Pro Ala Gly Lys Pro Leu Val Val Lys
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Peptide

<400> SEQUENCE: 55

Trp Lys Asp Glu Ala Gly Pro Lys Pro Leu Val Lys
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Peptide

<400> SEQUENCE: 56

Trp Lys Asp Glu Ala Gly Trp Ala Asp Lys Pro Leu Val Lys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Peptide

<400> SEQUENCE: 57

Trp Lys Asn Asp Glu Ala Gly Lys Pro Leu Val Lys
1               5                   10

<210> SEQ ID NO 58
<211> LENGTH: 9
<212> TYPE: PRT
<213> ORGANISM: Artificial Sequence
<220> FEATURE:
<223> OTHER INFORMATION: Peptide

<400> SEQUENCE: 58

Trp Lys Asp Ala Lys Pro Leu Val Lys
1               5
```

<210> SEQ ID NO 59
<211> LENGTH: 9
<212> TYPE: PRT
<213> ORGANISM: Artificial Sequence
<220> FEATURE:
<223> OTHER INFORMATION: Peptide

<400> SEQUENCE: 59

Trp Lys Glu Ala Gly Lys Pro Val Lys
1               5

<210> SEQ ID NO 60
<211> LENGTH: 10
<212> TYPE: PRT
<213> ORGANISM: Artificial Sequence
<220> FEATURE:
<223> OTHER INFORMATION: Peptide

<400> SEQUENCE: 60

Trp Lys Asp Glu Ala Lys Pro Leu Val Lys
1               5                   10

<210> SEQ ID NO 61
<211> LENGTH: 8
<212> TYPE: PRT
<213> ORGANISM: Artificial Sequence
<220> FEATURE:
<223> OTHER INFORMATION: Peptide

<400> SEQUENCE: 61

Trp Asp Glu Ala Gly Lys Pro Val
1               5

<210> SEQ ID NO 62
<211> LENGTH: 10
<212> TYPE: PRT
<213> ORGANISM: Artificial Sequence
<220> FEATURE:
<223> OTHER INFORMATION: Peptide

<400> SEQUENCE: 62

Trp Lys Asp Glu Ala Gly Lys Pro Val Lys
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Peptide

<400> SEQUENCE: 63

Trp Asp Ala Gly Lys Pro Leu Val Lys
1               5

<210> SEQ ID NO 64
<211> LENGTH: 10
<212> TYPE: PRT
<213> ORGANISM: Artificial Sequence
<220> FEATURE:
<223> OTHER INFORMATION: Peptide

<400> SEQUENCE: 64

Trp Lys Asp Glu Ala Gly Lys Pro Leu Val
1               5                   10

```
<210> SEQ ID NO 65
<211> LENGTH: 8
<212> TYPE: PRT
<213> ORGANISM: Artificial Sequence
<220> FEATURE:
<223> OTHER INFORMATION: Peptide

<400> SEQUENCE: 65

Trp Glu Ala Gly Lys Pro Leu Val
1               5

<210> SEQ ID NO 66
<211> LENGTH: 6
<212> TYPE: PRT
<213> ORGANISM: Artificial Sequence
<220> FEATURE:
<223> OTHER INFORMATION: Peptide

<400> SEQUENCE: 66

Trp Lys Asp Glu Ala Gly
1               5

<210> SEQ ID NO 67
<211> LENGTH: 5
<212> TYPE: PRT
<213> ORGANISM: Artificial Sequence
<220> FEATURE:
<223> OTHER INFORMATION: Peptide

<400> SEQUENCE: 67

Trp Lys Asp Glu Ala
1               5

<210> SEQ ID NO 68
<211> LENGTH: 8
<212> TYPE: PRT
<213> ORGANISM: Artificial Sequence
<220> FEATURE:
<223> OTHER INFORMATION: Peptide

<400> SEQUENCE: 68

Lys Asp Glu Ala Gly Lys Pro Leu
1               5

<210> SEQ ID NO 69
<211> LENGTH: 5
<212> TYPE: PRT
<213> ORGANISM: Artificial Sequence
<220> FEATURE:
<223> OTHER INFORMATION: Peptide

<400> SEQUENCE: 69

Lys Asp Glu Ala Gly
1               5

<210> SEQ ID NO 70
<211> LENGTH: 7
<212> TYPE: PRT
<213> ORGANISM: Artificial Sequence
<220> FEATURE:
<223> OTHER INFORMATION: Peptide

<400> SEQUENCE: 70

Asp Glu Ala Gly Lys Pro Leu
1               5

<210> SEQ ID NO 71
```

```
<211> LENGTH: 5
<212> TYPE: PRT
<213> ORGANISM: Artificial Sequence
<220> FEATURE:
<223> OTHER INFORMATION: Peptide

<400> SEQUENCE: 71

Gly Lys Pro Leu Val
1               5

<210> SEQ ID NO 72
<211> LENGTH: 5
<212> TYPE: PRT
<213> ORGANISM: Artificial Sequence
<220> FEATURE:
<223> OTHER INFORMATION: Peptide

<400> SEQUENCE: 72

Asp Glu Ala Gly Lys
1               5

<210> SEQ ID NO 73
<211> LENGTH: 9
<212> TYPE: PRT
<213> ORGANISM: Artificial Sequence
<220> FEATURE:
<223> OTHER INFORMATION: Peptide

<400> SEQUENCE: 73

Trp Lys Asp Glu Ala Gly Lys Pro Leu
1               5

<210> SEQ ID NO 74

<400> SEQUENCE: 74

000

<210> SEQ ID NO 75

<400> SEQUENCE: 75

000

<210> SEQ ID NO 76
<211> LENGTH: 5
<212> TYPE: PRT
<213> ORGANISM: Artificial Sequence
<220> FEATURE:
<223> OTHER INFORMATION: Peptide

<400> SEQUENCE: 76

Lys Pro Leu Val Lys
1               5

<210> SEQ ID NO 77
<211> LENGTH: 4
<212> TYPE: PRT
<213> ORGANISM: Artificial Sequence
<220> FEATURE:
<223> OTHER INFORMATION: Peptide

<400> SEQUENCE: 77

Trp Lys Asp Glu
1

<210> SEQ ID NO 78
```

```
<211> LENGTH: 5
<212> TYPE: PRT
<213> ORGANISM: Artificial Sequence
<220> FEATURE:
<223> OTHER INFORMATION: Peptide

<400> SEQUENCE: 78

Ala Gly Lys Pro Leu
1               5

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000
```